United States Patent
Nomoto et al.

(10) Patent No.: US 6,951,745 B2
(45) Date of Patent: Oct. 4, 2005

(54) POLYHYDROXYALKANOATE-CONTAINING STRUCTURE AND MANUFACTURING METHOD THEREOF

(75) Inventors: Tsuyoshi Nomoto, Tokyo (JP); Tetsuya Yano, Kanagawa (JP); Shinya Kozaki, Tokyo (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 453 days.

(21) Appl. No.: 10/191,540

(22) Filed: Jul. 10, 2002

(65) Prior Publication Data

US 2003/0224494 A1 Dec. 4, 2003

(30) Foreign Application Priority Data

Jul. 10, 2001 (JP) ........................................ 2001-210052
Jun. 13, 2002 (JP) ........................................ 2002-172978

(51) Int. Cl.$^7$ .............................. C12P 7/62; C12P 7/16; C12P 11/00
(52) U.S. Cl. ........................ 435/118; 435/123; 435/130; 435/131; 435/135; 435/176; 435/177; 435/178; 435/181; 435/182; 435/252.3; 424/450; 424/497; 428/402.24; 264/4.1; 536/23.1; 536/23.2
(58) Field of Search ................................. 435/118, 123, 435/130, 131, 135, 176, 177, 178, 181

(56) References Cited

U.S. PATENT DOCUMENTS 6,600,029 B1 * 7/2003 Sherman et al. ............ 536/135

FOREIGN PATENT DOCUMENTS

| JP | 2001-69968 | 3/2001 | ............ C12N/1/20 |
| JP | 2001-78753 | 3/2001 | ............ C12N/1/20 |

OTHER PUBLICATIONS

Speier, et al; "The Addition of Silicon Hydrides . . . Tribromosilane"; J. Am. Chem. Soc., vol. 78, 2278–2281 (1955).
Vogel, et al; "Acetylornithase of *Escherichia Coli*: . . . Properties"; published by the American Society of Biological Chemists, 97–106 (1956).
Ostle, et al; "Nile Blue A . . . Poly–β–Hydroxybutyrate"; Appl. & Environ. Microb., 44, 1, 238–241 (1982).
Charbit, et al; "Versatility of a vector . . . bacteria"; Gene, 70 (1988) 181–189.
Pistor, et al; "Expression of Viral . . . of *E. Coli*"; Klin. Wochenschr. (1988) 66:110–116.
Hedegaard, et al; "Type 1 fimbriae of . . . antigenic sequences"; Gene, 85 (1989) 115–124.
Klauser, et al; "Extracellular transport of . . . membrane translocation"; Embo. J. 9 (1990) 1991–1999.
Yamaguchi, et al; "Oxidation of . . . Oxoaminium Salt"; J. Org. Chem. (1990) 55, 1490–1492.

Cwirla, et al; "Peptides on phage: . . . ligands"; Proc. Natl. Acad. Sci. USA, 87, (1990) 6378–6382.
Scott, et al; "Searching for Peptide Ligands . . . Library"; Science, 249 (1990) 386–390.
Fodor, et al; "Light–Directed . . . Synthesis"; Science 251 (1991) 767–773.
Houghten, et al; "Generation and use of . . . drug discovery"; Nature; 354 (1991) 84–86.
Lam, et al; "A new type of synthetic peptide library . . . activity", Nature, 354 (1991) 82–84.
M. Hofnung; "Expression of Foreign Polypeptides . . . Cell Surface"; Methods in Cell Biology, 34, (1991) 77–105.
Fuchs, et al; "Targeting of Recombinant Antibodies . . . Lipoprotein"; Bio/Technology; 9 (1991) 1369–1372.
Sambrook, et al; "Molecular Cloning" $2^{nd}$ Ed., published by Cold Spring Harbor Laboratory Press, p. 5.72 (1989).
Francisco, et al; "Production and fluorescence– activated . . . external surface", Proc. Natl. Acad. Sci. USA, 90 (1993) 10444–10448.
Gerngross, et al; "Enzyme–catalyzed synthesis . . . in vitro"; Proc. Natl. Acad. Sci. USA, 92 (1995) 6279–6283.
Kraak, et al; "In vitro activities of granule–bound . . . *oleovorans*" Eur. J. Biochem. 250, 432–439 (1997).
Rehm, et al; "A New Metabolic Link . . . Acid Synthesis"; J. Biolog. Chem 273, 37, 24044–24051 (1998).
Lenz, et al; "Extracellular polymerization . . . *eutrophus*"; Int'l J. Biological Macrom. 25 (1999) 55–60.
Jossek, et al; "In vitro synthesis . . . recycling system"; FEMS Microbiology Letters, 168 (1998) 319–324.
Nobes, et al; "Growth and kinetics of . . . with coalescence"; Macromol. Rapid Commun. 21, 2, 77–84 (2000).
Pelletier, et al; "2–Hydroxycyclohexanecarboxyl . . . *palustris*"; J. Bact. 182, 10, 2753–2760 (2000).
Qi, et al; "In vitro synthesis . . . *aeruginosa*"; Appl. Microbiol. Biotechnol. 54, 37–43 (2000).

(Continued)

Primary Examiner—Herbert J. Lilling
(74) Attorney, Agent, or Firm—Fitzpatrick, Cella, Harper and Scinto

(57) ABSTRACT

A method for manufacturing polyhydroxyalkanoate-containing structure, at least a part of a base material surface of the structure being coated with polyhydroxyalkanoate, the method comprises the steps of immobilizing a polyhydroxyalkanoate synthase on the base material surface, synthesizing, on the base material surface, polyhydroxyalkanoate using a 3-hydroxyacyl coenzyme A to become the substrate of the synthase and the synthase and coating at least a part of the base material surface with the synthesized polyhydroxyalkanoate, wherein the synthase contains an amino acid sequence capable of binding to the base material. A polyhydroxyalkanoate-containing structure, at least a part of a base material surface of the structure being coated with a polyhydroxyalkanoate, comprises the base material, a polyhydroxyalkanoate synthase immobilized on the base material surface, and the polyhydroxyalkanoate with which at least a part of the base material surface is coated, wherein the synthase contains an amino acid sequence capable of binding to the base material.

38 Claims, 7 Drawing Sheets

OTHER PUBLICATIONS

Fritzsche et al.; "Production of Unsaturated Polyesters . . . Oleovorans"; Int. J. Biol. Macromol. 12, 85–91 (1990).

Bradbury et al.; "Use of Living Columns . . . Antibodies"; Bio/Technology 11 1565–1569 (1993).

Q. Qi, et al., "In vitro synthesis of poly (3–hydroxydecanoate): purification and enzymatic characterization of type II polyhydroxyalkanoate synthases PhaC1 and PhaC2 from *Pseudomonas aeruginosa*", Applied Microbiology and Biotechnology, vol. 54, No. 1, pp. 27–43 (2000).

T. U. Gerngross, et al., "Enzyme–catalyzed synthesis of poly((R)–(–)–3–hydroxybutyrate): Formation of macroscopic granules in vitro", Proceedings of the National Academy of Sciences of the United States, vol. 92, No. 14, pp. 6279–6283 (1995).

* cited by examiner

POLYHYDROXYALKANOATE-CONTAINING STRUCTURE AND MANUFACTURING METHOD THEREOF

BACKGROUND OF THE INVENTION

1. Field of the Invention

The present invention relates to a method for manufacturing polyhydroxyalkanoate-containing structure comprising the steps of immobilizing on a base material polyhydroxyalkanoate synthase involved in polyhydroxyalkanoate biosynthesis reaction and coating at least part of the base material with polyhydroxyalkanoate by polymerizing a 3-hydroxyacyl coenzyme A by use of the enzyme to synthesize the polyhydroxyalkanoate. More particularly, the invention relates to a method for manufacturing polyhydroxyalkanoate-containing structure by immobilizing to a base material polyhydroxyalkanoate synthase containing an amino acid sequence capable of binding to the base material.

The present invention relates to a structure that has polyhydroxyalkanoate, base material and polyhydroxyalkanoate synthase immobilized on the base material, the polyhydroxyalkanoate coating at least part of the base material. The structure of the present invention encompasses a granular structure (hereinafter called a "capsular structure") in which polyhydroxyalkanoate is coated on a granular base material, and a plate- or film-like structure (hereinafter called a "laminated structure") in which at least part of a plate- or film-like base material is coated with polyhydroxyalkanoate.

The structure of the present invention can find a wide range of applications as a functional structure. For example, the capsular structure can have a large number of applications as a variety of functional structures such as a pigment dispersant of excellent dispersion stability and a toner for electrophotography of excellent electrostatic property, and the laminated structure as various functional structures including an OHP film and an electronic device.

2. Related Background Art

Polymeric materials are essential to modern industries and our lives. The materials, which are inexpensive and lightweight and have good moldability, are widely utilized as packaging material and cushioning material, or fiber material, as well as boxes for household electrical appliances. On the other hand, diverse functional materials such as a liquid crystal material and a coat agent are also obtained by utilizing stable properties of these polymeric materials to thereby place substituents of exhibiting various functions on molecular chains of the polymers. These functional materials are higher in added values than polymers for structural materials and thus can be expected to have large market needs even in a small amount. These functional polymeric materials have been produced so far by organic, synthetic chemical methods in synthetic processes of polymers or by modifying synthesized polymers with substituents. Polymers of basic frameworks for functional polymeric materials have been obtained from petroleum based raw material by organic, synthetic chemical methods in most cases. Typical examples of these polymers include polyethylene, poly (ethylene terephthalate), polyesters, polystyrene, poly(vinyl chloride) and polyacrylamides.

Incidentally, the present inventors have focused on a multilayered structure, the base material of the structures being coated with a polymeric compound, as a basic element that imparts large added values to the polymeric compound. A composite structure of extremely useful functionality can be obtained by coating a specific base material with a polymeric compound.

While polymeric compounds used for coating base materials are conventionally synthesized and made to be structures by organic synthetic processes and then various functions are added to them, recently, the production of polymeric compounds by bioengineering approaches has been actively studied and part of it is operational. Known examples include as polymeric compounds derived from microbes polyhydroxyalkanoates (hereinafter sometimes abbreviated as PHAs) such as poly-3-hydroxy-n-butyric acid (hereinafter sometimes abbreviated as PHB), and a copolymer of 3-hydroxy-n-butyric acid and 3-hydroxy-n-valeric acid (hereinafter sometimes abbreviated as PHB/V), polysaccharides such as bacteria cellulose and pullulan, and polyamino acids such as poly-γ-glutamic acid and polylysine. In particular, PHAs can be utilized for various products by melt processing, or the like, like conventional plastics and also exhibit excellent biocompatibility, thus being expected to find applications including flexible materials for medical treatment.

Recently, an attempt has been started to synthesize PHAs in vitro by taking the aforementioned PHB synthase or PHA synthase out of the microbe.

For example, a PHB composed of a 3-hydroxy-n-butyric acid unit has been successfully synthesized by causing the action of 3-hydroxybutylyl CoA on a PHB synthase derived from Alcaligenes eutrophus (Proc. Natl. Acad. Sci. USA, 92, 6279–6283, 1995). In addition, PHBs composed of a 3-hydroxy-n-butyric acid unit or a 3-hydroxy-n-valeric acid unit has been successfully synthesized by causing the action of 3-hydroxybutyryl CoA or 3-hydroxyvaleryl CoA on a PHB synthase derived from Alcaligenes eutrophus (Int. J. Biol. Macromol., 25, 55–60, 1999). Furthermore, in this study, a PHB composed only of the R form of a 3-hydroxy-n-butyric acid unit was synthesized, due to stereo-selectivity of an enzyme, by the action of a racemic modification of 3-hydroxybutyryl CoA. A PHB has been synthesized in vitro using a PHB synthase derived from Alcaligenes eutrophus as well (Macromol. Rapid Commun., 21, 77–84, 2000).

In addition, a PHB composed of a 3-hydroxy-n-butyric acid unit has been successfully synthesized by causing the action of 3-hydroxybutyryl CoA on a PHB synthase derived from *Chromatium vinosum* (FEMS Microbiol. Lett., 168, 319–324, 1998).

A PHA composed of 3-hydroxydecoic acid unit has been synthesized by causing the action of 3-hydroxydecanoil CoA on *Pseudomonas aeruginosa* of PHA synthases (Appl. Microbiol. Biotechnol., 54, 37–43, 2000).

As discussed above, application of bioengineering approaches to polymeric compounds will be able to synthesize new polymeric compounds that are difficult to synthesize by conventional organic synthetic methods and provide new functions and structures. In addition, although conventional, organic, synthetic chemical methods requires a manufacturing step of many stages, the bioengineering method needs only a one-stage step in many cases and therefore is expected to simplify the manufacturing step, save costs and shorten the turnaround time. Further, the method makes it possible to decrease the use of organic solvents, acids and alkalis, surfactants, etc., set mild reaction conditions and synthesize a target material from nonpetroeum-based raw material and low purity raw material, thereby being able to realize a synthetic process of a lower environmental load and a resource recycling type.

Additionally, for more detailed description of the synthesis of the low purity raw material, the bioengineering synthetic process generally has a high substrate specificity of an enzyme, or a catalyst, which permits a target reaction to selectively proceed even though a material of a low purity is used, thus enabling the use of waste and recycling raw material.

On the other hand, as described previously, the present inventors have focused attention on a structure made by coating a base material with a polymeric compound as an element for imparting a large added value to the polymeric compound. Coating a specific base material with a polymeric compound like this can provide a composite structure having extremely useful functionality. In particular, if this type of structure can be produced by a bioengineering approach as previously mentioned, utilization of a novel polymeric compound that is difficult to produce by a conventional organic synthetic method or new additions of functions and structures will be made possible and thereby a manufacturing process of a lower environmental load and resource recycling type will be realized at a low cost. For example, use of extremely precise molecule recognition ability and stereo selectivity that are specific in catalytic action of living organisms can produce by a simple and easy process of a lower environmental load a novel polymeric compound of functionality that is difficult to produce by a conventional organic synthetic chemical method, or a capsular structure or laminated structure that is coated with an extremely high chirality polymeric compound.

Therefore, it is an object of the present invention to provide a polymeric compound structure of high functionality by means of a bioengineering approach and a manufacturing method thereof and more specifically to provide more effective utilization of an enzyme when a structure, the base material of which is coated with a PHA, is to be produced by taking a PHB synthase or PHA synthase out of the microbe to synthesize a PHA in vitro. In addition, it is another object of the present invention to provide a structure, the base material of which is coated with a polymeric compound, that can be widely utilized as a composite structure of functionality, and an effective manufacturing method thereof.

SUMMARY OF THE INVENTION

The present inventor have conducted a study that involves screening of an amino acid sequence of a peptide capable of binding to a base material from a peptide library, fusing the peptide of this amino acid sequence with a PHA synthase by means of a genetic engineering method and presenting it resulting in effective immobilization of the PHA synthase on the surface of a base material, performing a synthetic reaction by the addition of a 3-hydroxyacyl coenzyme A to the resulting material leading to a finding of effective coating of the base material surface with a desirable PHA, which has completed the present invention. In other words, the present invention relates to a method for manufacturing a structure containing polyhydroxyalkanoate, at least part of the base material of the structure being coated with the polyhydroxyalkanoate, and to the method for producing the structure that comprises immobilizing on the base material polyhydroxyalkanoate synthase containing an amino acid sequence capable of binding to the base material and adding a 3-hydroxyacyl coenzyme A to be the substrate of the enzyme.

The present invention can effectively immobilize a PHA synthase on the surface of a base material, and so when a synthesis reaction is conducted by the addition of a 3-hydroxyacyl coenzyme A, no isolated PHA granules are generated, which can effectively coat the base material surface with the PHA.

A structure relating to the present invention has a structure wherein at least part of the base material surface is coated with a PHA, and when the whole base material is coated with a PHA layer, a capsular structure, the base material of which is the nucleus, can be obtained.

DETAILED DESCRIPTION OF THE PREFERRED EMBODIMENTS

Figure 1A:
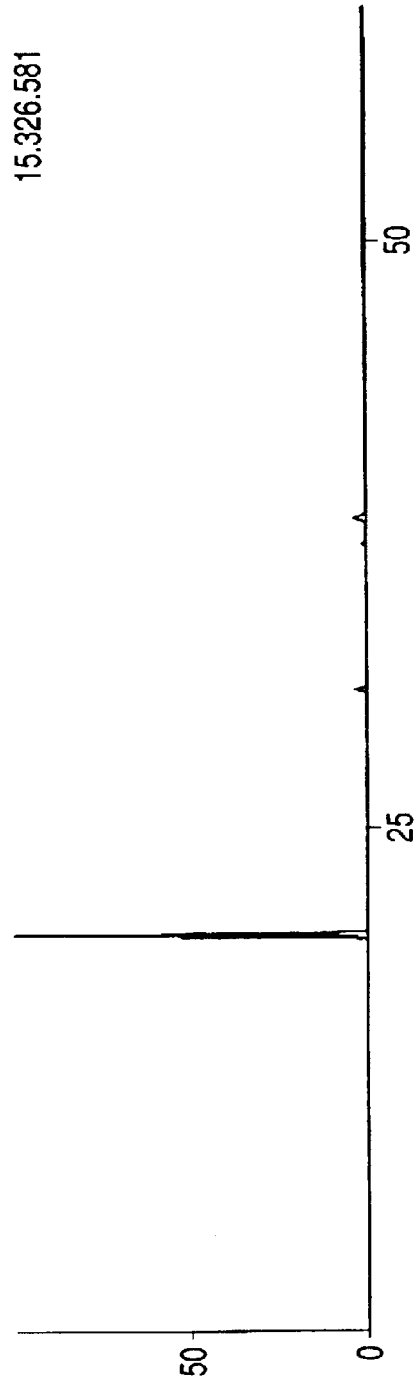
FIGS. 1A and 1B show GC-MS analysis results of the outer shell of a PHA capsular structure using copper phthalocyanine in Example 4.

In the present invention, for a base material to be coated with a PHA, if it can immobilize a PHA synthase, a general polymeric compound or inorganic solid material, e.g., resin, glass or a metal, can be selected, as required, and used. The kind or structure of a base material can be selected, as required, and used according to a method of immobilizing a PHA synthase, the form of application of a produced structure, etc.

Examples of the granular base material (core) include resin particulates produced by polymerizing polymerizable monomers selected from the group consisting of styrene base polymerizable monomers such as styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene, and p-phenylstyrene, acrylic polymerizable monomers such as methyl acrylate, ethyl acrylate, n-propyl acrylate, iso-propyl acrylate, n-butyl acrylate, iso-butyl acrylate, tert-butyl acrylate, n-amyl acrylate, n-hexyl acrylate, 2-ethylhexyl acrylate, n-octyl acrylate, n-nonyl acrylate, cyclohexyl acrylate, benzyl acrylate, dimethylphophate ethyl acrylate, diethylphosphate ethyl acrylate, dibutylphosphate ethyl acrylate, and 2-benzoyloxyethyl acrylate, methacrylic polymerizable monomers such as methyl methacrylate, ethyl methacrylate, n-propyl methacrylate, iso-propyl methacrylate, n-butyl methacrylate, iso-butyl methacrylate, tert-butyl methacrylate, n-amyl methacrylate, n-hexyl methacrylate, 2-ethylhexyl methacrylate, n-octyl methacrylate, n-nonyl methacrylate, diethylphosphate ethyl methacrylate, and dibutylphosphate ethyl methacrylate, vinyl base polymerizable monomers including methylene aliphatic monocarboxylates, vinyl ethers such as vinyl acetate, vinyl propionate, vinyl benzoete, vinyl butylate, vinyl benzoate, and vinyl formate, vinyl ethers such as vinylmethyl ether, vinylethyl ether, and vinylisobutyl ether, vinyl ketones such as vinyl methyl ketone, vinyl hexyl ketone, and vinyl isopropyl ketone; resin particulates produced by adding to the above described monomers a variety of additives such as polymers of polar groups and colorants; particulates including paraffin wax, polyolefin wax, Fischer Tropshch wax, amide wax, higher fatty acids, ester wax, derivatives thereof, graft compounds thereof, and block compounds thereof; clay minerals such as kaolinite, bentonite, talc, and mica; metal oxides such as alumina and titanium dioxide; insoluble inorganic salts such as silica gel, hydroxyapatite, and calcium phosphate gel; black pigments such as carbon black, copper oxide, manganese dioxide, aniline black, activated carbon, nonmagnetic ferrite, and magnetite; yellow pigments such as Chrome Yellow, Zinc Yellow, Iron Oxide Yellow, Cadmium Yellow, Mineral Fast Yellow, Nickel Titanium Yellow, Neburs Yellow, Naphthol Yellow S, Hanzar Yellow G, Hanza Yellow 10G, Benzidine Yellow G, Benzidine Yellow GR, Quinoline Yellow Lake, Permanent Yellow NCG, and Turtladine Lake; orange pigments such as Orange Chrome, Molybdenum Orange, Permanent Orange GTR, Pyrazolone Orange, Vulcan Orange, Benjidine Orange G, Indanthlene Brilliant Orange RK, and Indanthlene Brilliant Orange GK; red pigments such as Red Iron Oxide, Cadmium Red Lead, mercury sulfate, cadmium, Permanent Red 4R, Lithol Red, Pyrazolone Red, Watching Red, calcium salt, Lake Red C, Lake Red D, Brilliant Carmin 6B, Brilliant Carmin 3B, Eoxine Lake, Rhodamine Lake B, or Alizarin Lake; blue pigments such as Milori Blue, Cobalt Blue, Alkali Blue Lake, Victoria Blue Lake, Phthalocyanine Blue, Non-metal Phthalocyanine Blue, partly chloride Phthalocyanine Blue, Fast Sky Blue, and Indanthrene Blue BC; violet pigments such as Manganese Violet, Fast Violet B, or Methyl Violet Lake; green pigments such as chromium oxide, Chrome Green, Pigment Green B, Malachite Green Lake, and Final Yellow Green G; white pigments such as Zinc White, titanium oxide, Antimony White, zinc sulfate; and extender pigments such as baryta powder, barium carbonate, clay, silica, white carbon, talc, and Alumina White. Of course, the granular base material is not limited to these substances. These substances can be used in a combination of two substances or more, as necessary. The shape of the base material can be selected, as necessary, dependent on its application and, for example, it is good to use a particle with a particle size of 0.1 μm to 1.0 mm.

In addition, other forms of the base material include films made of plastics such as poly(ethylene terephthalate) (PET), diacetates, triacetates, cellophane, celluloid, polycarbonates, polyimides, polyvinyl chloride, poly(vinylidene chloride), polyacrylate, polyethylene, polypropylene, and polyesters; porous polymer membranes such as poly(vinyl chloride), poly(vinyl alcohol), acetyl cellulose, polycarbonate, nylon, polypropylene, polyethylene, and Teflon; clothes such as wooden plates, glass plates, silicon boards, cotton, rayon, acryl, silk, and polyesters; and paper such as high quality paper, medium quality paper, art paper, bond paper, recycled paper, baryta paper, cast coat paper, corrugated cardboard paper, and resin coat paper. Off course, the base material is not limited to these materials. Further, the aforementioned base material is acceptable even if its surface is even or uneven, or even if it is transparent, translucent, or opaque. Furthermore, a material made by binding two or more materials of the aforementioned base materials to one another is acceptable.

In order to obtain an amino acid sequence of a peptide having binding affinity to a base material of the present invention, an example of the phage display peptide library method described below is available. For forming a phage random peptide library, a random synthesis gene is, for example, connected to the N terminal side gene of the surface protein (e.g., the gene III protein) of a M13 base phage. Its methods have been reported by Scott, J K. and Smith (G P., Science Vol. 249, 386, 1990), Cwirla, S E et al. (Proc. Natl. Acad. Sci. USA Vol. 87, 6378, 1990), etc. The size of a gene to be inserted is not particularly limited if the peptide is stably expressed; however, the size corresponding to the number of amino acids of 6 to 40 (corresponding to a molecular weight of about 600 to 4000) is appropriate in order to cover all the random sequences of a formed library and for these sequences to have binding ability, and of them the size corresponding to 7 to 18 amino acids is preferable. In order to select a phage that bonds to a target base material, the base material is, for example, fixed on a column or a plate and the above mentioned library is contacted with the base material and then a binding phage is kept but a non-binding phage is washed away. The phage left after washing is eluted by means of an acid, etc. and the eluate is neutralized with a buffer and then the phage is incorporated into $E.$ $coli$ to amplify it. Repetition of this selection of a plurality of times concentrates a plurality of clones that are capable of binding to a target base material. At this time, to obtain a single clone, the phage is again allowed incorporated into the $E.$ $coli$ to make a colony on a culture plate. After each single colony is cultured in a liquid culture medium, the phage present in a supernatant of the medium is precipitation purified with polyethylene glycol, or the like. The structure of the peptide is determined by the analysis of this base sequence.

A peptide chemically synthesized can be used in addition to the aforementioned phage-using method for the forming of a peptide library possessing a random amino acid sequence. The method includes, for example, a method of using beads (Lam, K S et al., Nature, 354, 82, 1991), a liquid focusing method (Houghton, R A et al., Nature, 354, 84, 1991), and a microplate method (Fodor, SPA et al., Science, 251, 767, 1991), which can be applied to the present invention.

An amino acid sequence of a peptide having binding affinity to a base material obtained by the above mentioned method is utilized by fusing the sequence into polyhydroxyalkanoate synthase by means of a usual genetic engineering method. A peptide capable of binding to a base material can be expressed by being connected to the N terminal or C terminal of polyhydroxyalkanoate synthase. Alternatively, a suitable spacer sequence is inserted to express the peptide as well.

A spacer sequence preferably has a range of about 3 to about 400 amino acids, and the sequence may contain any amino acid. Most preferably, a spacer sequence is one that does not prevent the function of a PHA synthase or does not disturb the binding of a PHA synthase to a base material.

<PHA>

PHA capable of being used in the present invention is not particularly limited as long as such a PHA can be synthesized with a PHA synthesizing enzyme involved in a biosynthesis reaction of PHA.

Here, the biosynthesis of PHA is carried out through a polymerization reaction by an enzyme using as a substrate (R)-3-hydroxyacyl CoA produced from alkanoic acids as a substrate by way of various metabolic pathways in an organism (e.g. β-oxidation system and fatty acid synthesis pathway). It is a PHA synthesizing enzyme (also referred to as PHA polymerase, PHA synthase) that catalyses this polymerization reaction. The term "CoA" is an abbreviation of coenzyme A, of which chemical structure is as follows:

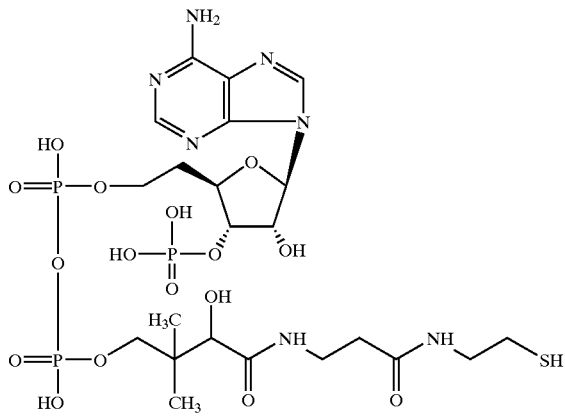

A reaction by which PHA is produced from alkanoic acid through a polymerization reaction by a β-oxidation system and a PHA synthesizing enzyme is shown in the following:

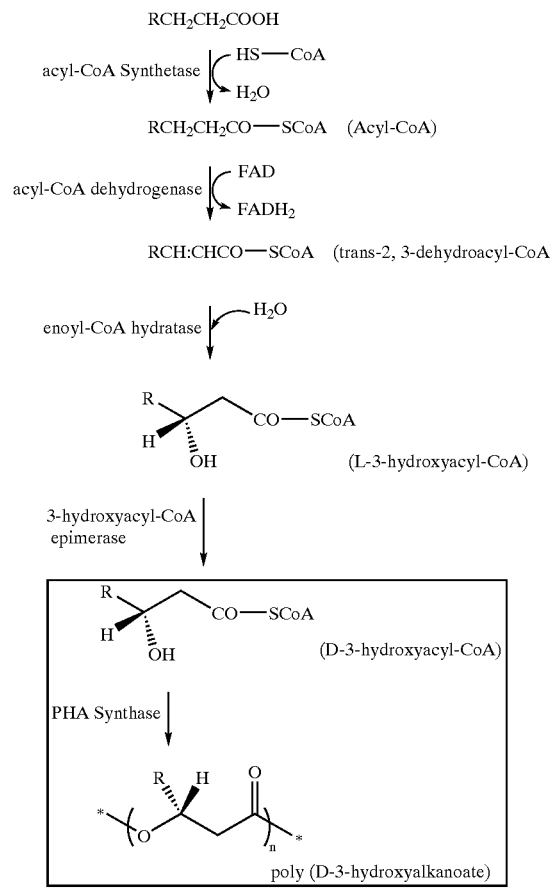

On the other hand, if the reaction is carried out by way of the fatty acid synthesis pathway, it can be considered that PHA is similarly synthesized by the PHA synthesizing enzyme using as a substrate (R)-3-hydroxyacyl CoA into which (R)-3-hydroxyacyl-ACP (ACP means an acyl carrier protein) produced in the pathway has been converted.

In addition, it is known that the above described PHB synthesizing enzyme and PHA synthesizing enzyme can be taken out from the cell to synthesize PHA in a cell-free system (in vitro), and specific examples thereof will be described below.

For example, in Proc. Natl. Acad. Sci. USA, 92, 6279–6283 (1995), it is reported that PHB comprising a 3-hydroxy-n-butanoic acid unit has been successfully synthesized by making 3-hydroxybutyryl CoA act on a PHB synthesizing enzyme derived from *Alcaligenes eutrophus*. In addition, it is reported in Int. J. Biol. Macromol., 25, 55–60 (1999) that PHA comprising a 3-hydroxy-n-butyryl acid unit or a 3-hydroxy-n-valeric acid unit has been successfully synthesized by making 3-hydroxybutyryl CoA and 3-hydroxyvaleryl CoA act on the PHB synthesizing enzyme derived from *Alcaligenes eutrophus*. In addition, according to this report, when racemic 3-hydroxybutyryl CoA was made to act on the enzyme, PHB comprising only a 3-hydroxy-n-butyric acid unit of R-configuration was synthesized due to the stereoselectivity of the enzyme. Synthesis of PHB outside the cell using a PHB synthesizing enzyme derived from *Alcaligenes eutrophus* is also reported in Macromol. Rapid Commun., 21, 77–84 (2000). In addition, it is reported in FEMS Microbiol. Lett., 168, 319–324 (1998) that PHB comprising a 3-hydroxy-n-butyric unit has been successfully synthesized by making 3-hydrozybutyryl CoA act on a PHB synthesizing enzyme derived from *Chromatium vinosum*. It is reported in Appl. Microbiol. Biotechnol., 54, 37–43 (2000) that PHA comprising a 3-hydroxydecanoic acid unit has been synthesized by making 3-hydroxydecanoyl CoA act on a PHA synthesizing enzyme from *Pseudomonas aeruginosa*.

In this way, the PHA synthesizing enzyme is an enzyme catalyzing a final stage in the PHA synthesis reaction system in an organism, and any PHA known to be capable of being synthesized in the organism is synthesized under catalytic action by the enzyme. Therefore, by making 3-hydroxyacyl CoA corresponding to desired PHA act on the enzyme fixed on the medium in the present invention, pigment-coated capsular structure with any type of PHA known to be capable of being synthesized in the organism can be prepared.

As an example of PHA for use in the present invention, PHA containing at least monomer units expressed by the following formulas [1] to [10] can specifically be shown.

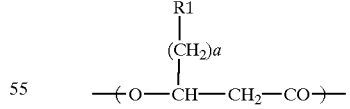

[1]

(wherein the monomer unit is at least one selected from the group consisting of monomer units having any of the following combinations of R1 and a:

a monomer unit in which R1 represents a hydrogen atom (H), and a represents an integer number of 0 to 10;

a monomer unit in which R1 represents a halogen atom, and a represents an integer number of 1 to 10;

a monomer unit in which R1 represents a chromophoric group, and a represents an integer number of 1 to 10;

a monomer unit in which R1 represents a carboxyl group or a salt thereof, and a represents an integer number of 1 to 10; and a monomer unit in which R1 represents,

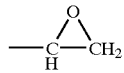

and a represents an integer number of 1 to 7.)

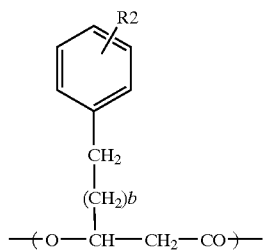

[2]

(wherein b represents an integer number of 0 to 7, and R2 represents any one selected from the group consisting of a hydrogen atom (H), halogen atom, —CN, —NO$_2$, —CF$_3$, —C$_2$F$_5$ and —C$_3$F$_7$.)

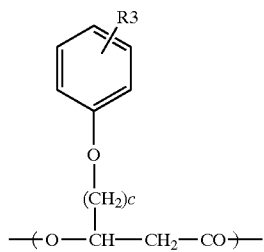

[3]

(wherein c represents an integer number of 1 to 8, and R3 represents any one selected from the group consisting of a hydrogen atom (H), halogen atom, —CN, —NO$_2$, —CF$_3$, —C$_2$F$_5$ and —C$_3$F$_7$.)

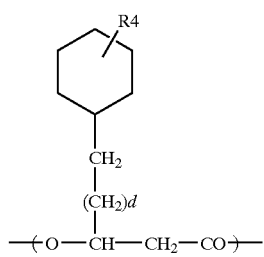

[4]

(wherein d represents an integer number of 0 to 7, and R4 represents any one selected from the group consisting of a hydrogen atom (H), halogen atom, —CN, —NO$_2$, —CF$_3$, —C$_2$F$_5$ and —C$_3$F$_7$.)

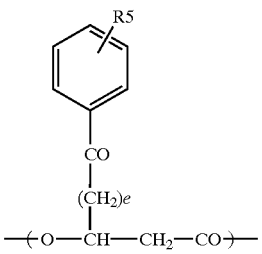

[5]

(wherein e represents an integer number of 1 to 8, and R5 represents any one selected from the group consisting of a hydrogen atom (H), halogen atom, —CN, —NO$_2$, —CF$_3$, —C$_2$F$_5$, —C$_3$F$_7$, —CH$_3$, —C$_2$H$_5$ and —C$_3$H$_7$).

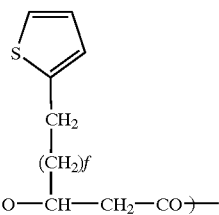

[6]

(wherein f represents an integer number of 0 to 7.)

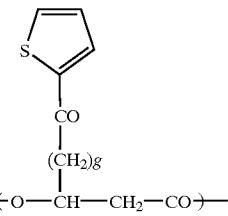

[7]

(wherein g represents an integer number of 1 to 8.)

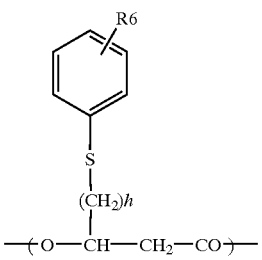

[8]

(wherein h represents an integer number of 1 to 7, R6 represents any one selected from the group consisting of a hydrogen atom (H), halogen atom, —CN, —NO$_2$, —COOR', —SO$_2$R'', —CH$_3$, —C$_2$H$_5$, —C$_3$H$_7$, —CH(CH$_3$)$_2$ and —C(CH$_3$)$_3$ wherein R' represents any of a hydrogen atom (H), Na, K, —CH$_3$ and —C$_2$H$_5$, and R'' represents any of —OH, —ONa, —OK, a halogen atom, —OCH$_3$ and —OC$_2$H$_5$.)

[9]

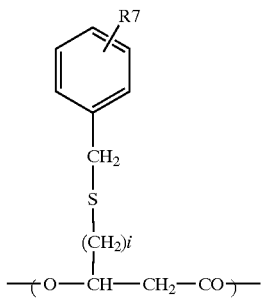

(wherein i represents an integer number of 1 to 7, R7 represents any one selected from the group consisting of a hydrogen atom (H), halogen atom, —CN, —$NO_2$, —COOR' and —$SO_2R''$ wherein R' represents any of a hydrogen atom (H), Na, K, —$CH_3$ and —$C_2H_5$, and R" represents any of —OH, —ONa, —OK, a halogen atom, —$OCH_3$ and —$OC_2H_5$.)

[10]

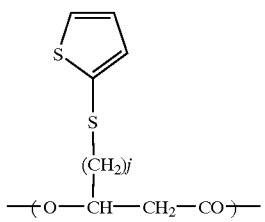

(wherein j represents an integer number of 1 to 9.)

Furthermore, examples of the above described halogen atom may include fluorine, chlorine and bromine.

A specific example of 3-hydroxyacyl CoA for use as a substrate for synthesizing the above PHA may be 3-hydroxyacyl CoA expressed by the following Chemical Formulas [12] to [21]:

[12]

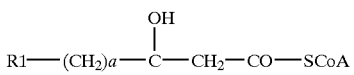

(wherein —SCoA represents a CoA bound to alkanoic acid, and the combination of R1 and a is defined as the same as the combinations of R1 and a in the monomer unit expressed by the above described Formula [1].)

[13]

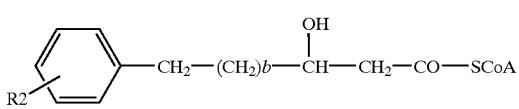

(wherein —SCoA represents a CoA bound to alkanoic acid, and b and R2 are respectively defined as the same as b and R2 in the monomer unit expressed by the above described Chemical Formula [2].)

[14]

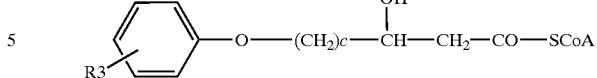

(wherein —SCoA represents a CoA bound to alkanoic acid, and c and R3 are respectively defined as the same as c and R3 in the monomer unit expressed by the above described Chemical Formula [3].)

[15]

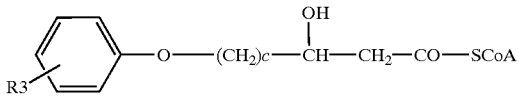

(wherein —SCoA represents a CoA bound to alkanoic acid, and d and R4 are respectively defined as the same as d and R4 in the monomer unit expressed by the above described Chemical Formula [4].)

[16]

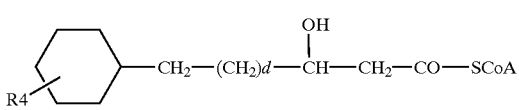

(wherein —SCoA represents a CoA bound to alkanoic acid, and e and R5 are respectively defined as the same as e and R4 in the monomer unit expressed by the above described Chemical Formula [5].)

[17]

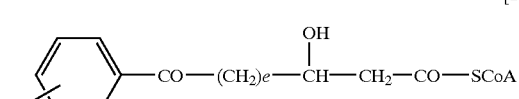

(wherein —SCoA represents a CoA bound to alkanoic acid, and f is defined as the same as f in the monomer unit expressed by the above described Chemical Formula [6].)

[18]

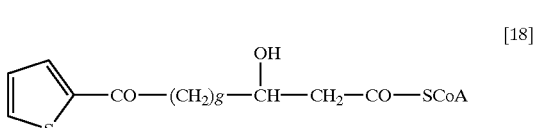

(wherein —SCoA represents a CoA bound to alkanoic acid, and g is defined as the same as g in the monomer unit expressed by the above described Chemical Formula [7].)

[19]

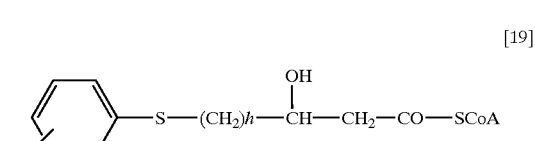

(wherein —SCoA represents a CoA bound to alkanoic acid, and h and R6 are respectively defined as the same as h and R6 in the monomer unit expressed by the above described Chemical Formula [8].)

[20]

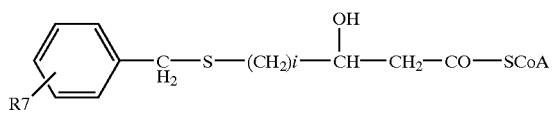

(wherein —SCoA represents a CoA bound to alkanoic acid, and i and R7 are respectively defined as the same as i and R7 in the monomer unit expressed by the above described Chemical Formula [9].)

[21]

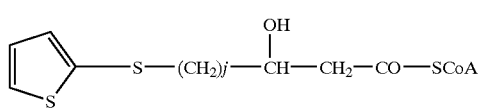

(wherein —SCoA represents a CoA bound to alkanoic acid, and j is defined as the same as j in the monomer unit expressed by the above described Chemical Formula [10].)

In addition, in the case where the surface of the base material is hydrophilic in the PHA-containing structure, PHA having a hydrophilic functional group is used as PHA constituting the PHA-containing structure. The hydrophilic functional group may be any hydrophilic functional group, but an anionic functional group can be used, and the anionic functional group may be any anionic functional group, but a carboxyl group can be used in particular. An example of PHA having a carboxyl group may be PHA comprised of at least one selected the group consisting of monomer units expressed by the following formula [11].

[11]

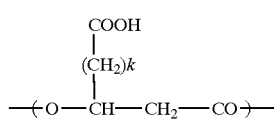

(wherein k represents any one of integer numbers of 1 to 10.)

In addition, a specific example of the above PHA may be PHA containing 3-hydroxypimelic acid expressed by the following Formula [23].

[23]

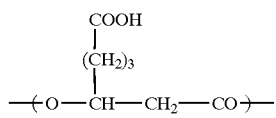

In addition, an example of 3-hydroxyacyl CoA for use as a substrate for synthesizing PHA expressed by the above Formula [11] may be 3-hydroxyacyl CoA expressed by the following Formula [22].

[22]

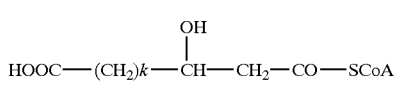

(wherein SCoA represents a CoA bound to alkanoic acid, and k is defined as the same as k in the monomer unit expressed by the above described Formula [11].

In addition, 3-hydroxyacyl CoA for use as a substrate for synthesizing PHA containing 3-hydroxypimelic acid expressed by the above Formula [23] may be 3-hydroxypimeril CoA expressed by the following Formula [24].

[24]

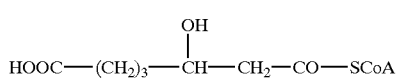

Furthermore, specific examples of the above described halogen atom may include fluorine, chlorine and bromine. In addition, the above described chromophoric group is not particularly limited as long as its 3-hydroxyacyl CoA body can be subjected to catalytic action of the PHA synthesizing enzyme, but it is more desirable that a methylene chain having 1 to 5 carbon atoms exists between the carboxyl group with CoA bound thereto and the chromophoric group in the 3-hydroxyacyl CoA molecule if considering steric hindrance that may occur during synthesis of a polymer. In addition, if the optical absorption wavelength of the chromophoric group is in the visible range, a colored PHA-containing structure can be obtained. Examples of such chromophoric groups may include nitroso, nitro, azo, diarylmethane, triarylmethane, xanthene, acridine, quinoline, methine, thiazole, indamine, indophenol, lactone, aminoketone, hydroxyketone, stilbene, azine, oxazine, thiazin, anthraquinone, phthalocyanine and indigoid.

For PHA to be used in the present invention, random copolymers and block copolymers each including the above described plurality of monomer units can also be used, thus making it possible to control properties of PHA and provide a plurality of functions using the properties of respective monomer units and contained functional groups, to realize new functions using interaction between functional groups, and so on. In addition, it is also possible to synthesize a block copolymer of any order and composition on the surface of the base material by selecting as appropriate the amount and order in which 3-hydroxyacyl CoA as a substrate is added. In addition, as required, chemical modification and the like may also be made after or during synthesis of PHA.

It is also possible to change the composition of the monomer unit of PHA in the laminating direction of the polyhydroxyalkanoate-containing structure to the outside thereof by changing with time the composition such as type and concentration of 3-hydroxyacyl CoA as a substrate, for example. Thereby, for example, if it is necessary to form a coated structure with PHA having a low affinity for the base material, the base material is first covered with PHA having a high affinity for the base material, and the composition of the monomer unit of PHA having a high affinity for the base material is changed to the composition of the monomer unit of desired PHA in the laminated direction to form, for example, a multi-layer structure or gradient structure, thereby making it possible to form a PHA cover with its bonding to the base material enhanced.

In addition, chemical modification of the PHA can provide polyhydroxyalkanoate-containing structure various properties of which are improved. For example, the incorporation of a graft chain into a PHA can give polyhydroxyalkanoate-containing structure in which at least part of the base material has been coated with the PHA being given a variety of properties attributable to the graft chain. Further, crosslinking the PHA can provide polyhydroxyalkanoate-containing structure in which at least part of the base material has been coated with the PHA given a variety of physicochemical properties (for example, mechanical strength, resistance to chemicals and heat resistance). The term, "chemical modification" as used in the present invention indicates the meaning that the molecular structure of a polymer substance is altered by allowing an intramolecular or intermolecular chemical reaction of the polymer substance or a chemical reaction between the polymer substance and another chemical substance. The term, "crosslinking" indicates the meaning that a polymer substance is chemically or physicochemically bonded intramolecularly or intermolecularly to form a network structure. Furthermore, a crosslinking agent refers to a substance having a certain reactivity with the aforementioned polymer substance which is added to carry out the above crosslinking reaction.

Furthermore, PHA synthesized by a PHA synthesizing enzyme, which is used in the structure of the present invention, is generally an isotactic polymer constituted only by a R-configuration.

3-hydroxyacyl CoA as a synthesis substrate for PHA can be synthesized for use by a method appropriately selected from an in vitro synthesis method using enzymes, an in vivo synthesis method using organisms such as microorganisms and plants, a chemical synthesis method, and the like. In particular, the enzyme synthesis method is a method that is generally used for synthesis of the substrate, and known enzyme synthesis methods include a method using the following reaction using commercially available acyl CoA synthetase (Acyl CoA Ligase, E.C.6.2.1.3)(Eur. J.Biochem., 250, 432–439 (1997), Appl. Microbiol. Biotechnol., 54, 37–43 (2000), etc.):

acyl CoA synthetase 3-hydroxyalkanoic acid+CoA→3-hydroxyacyl CoA.

For the synthesis process using enzymes and organisms, a batch type synthesis method may be used, or series production may be carried out using immobilized enzymes and immobilized cells.

<PHA Synthesizing Enzymes and Microorganisms for Producing the Enzymes>

For the PHA synthesizing enzyme for use in the present invention, an enzyme produced by a microorganism appropriately selected from microorganisms capable of producing the enzyme, or a transformant with the gene of a PHA synthesizing enzyme introduced into the host may be used.

For microorganisms for producing PHA synthesizing enzymes, PHB or PHB/V producing microorganisms may be used, and as these microorganisms, *Burkholderia cepacia* KK01, *Ralstonia eutropha* TB64, *Alcaligenes* sp. TL2 that have been isolated by the inventors may be used in addition to *Aeromonas* sp., *Alcaligenes* sp., *Chromatium* sp., *Comamonas* sp., *Methylobacterium* sp., *Paracoccus* sp., *Pseudomonas* sp. and the like. Furthermore, KK01, TB64 and TL2 are deposited as FERM BP-4235, FERM BP-6933 and FERM BP-6913, respectively, in National Institute of Advanced Industrial Science and Technology, International Patent Organism Depositary.

Also, as microorganisms for producing PHA synthesizing enzymes, microorganisms producing mcl-PHA and unusual-PHA may be used, and as these microorganisms may be used *Pseudomonas* sp. microorganisms such as *Pseudomonas putida* P91, *Psuedomonas cichorii* H45, *Pseudomonas cichorii* YN2, *Pseudomonas jessenii* P161, etc. that have been isolated by the inventors, in addition to *Pseudomonas oleoborans*, *Pseudomonas resinoborans*, *Pseudomonas* sp. 61–3, *Pseudomonas putida* KT2442, *Pseudomonas aeruginosa* and the like, and *Burkholderia* sp. microorganisms such as *Burkholderia* sp. OK3 (FERM P-17370) described in Japanese Patent Application Laid-Open No. 2001-78753 and *Burkholderia* sp. OK4 (FERM P-17371) described in Japanese Patent Application Laid-Open No. 2001-69968. Also, in addition to these microorganisms, microorganisms belonging to *Aeromonas* sp., *Comamonas* sp. and the like and producing mcl-PHA and unusual-PHA can be used.

Furthermore, P91, H45, YN2 and P161 are deposited on an international basis as FERM BP-7373, FERM BP-7374, FERM BP-7375 and BP-7376, respectively, in National Institute of Advanced Industrial Science and Technology, International Patent Organism Depositary, under Budapest Treaty on international approval for deposition of microorganisms in terms of patent procedures.

For normal culture of microorganisms for use in production of PHA synthesizing enzymes according to the present invention, for example preparation of stock strains, and reproduction for securing the number of cells and their active states required for production of the PHA synthesizing enzyme, a culture medium containing components needed for growth of microorganisms to be used is appropriately selected and used. For example, any type of culture media such as general natural culture media (broths, yeast extracts, etc) and synthetic culture media with nutrient sources added thereto may be used unless they adversely affect growth and survival of microorganisms.

For the culture, any method such as liquid culture and solid culture may be used as long as reproduction of the microorganisms is possible. In addition, any type of culture including batch culture, fed batch culture, semi-continuous culture and continuous culture may be used. As for the form of the liquid batch culture, a method in which oxygen is supplied by shaking with a shaking flask, a method in which oxygen is supplied using a stirring aeration system with a jar fermenter and the like are employed. In addition, a multistage method in which these steps are connected in multiple stages may be employed.

In the case where the PHA synthesizing enzyme is produced using PHA producing microorganisms as described above, for example, a method in which the microorganism is grown in an inorganic culture medium containing alkanoic acid such as octanoic acid and nonanoic acid, and cells of the microorganism in the logarithmic growth phase to the early stage of the stationary phase are collected by centrifugation or the like to extract a desired enzyme, and so on may be used. Furthermore, if the microorganism is cultured using a condition as described above, mcl-PHA derived from added alkanoic acid is synthesized in a cell of the microorganism, but in this case, it is generally said that the PHA synthesizing enzyme exists in such a manner as to be bound to small particles of PHA produced in the cell. However, as a result of studies conducted by the inventors, it has been found that almost equivalent enzyme activity is present even in the supernatant liquid after conducting centrifugation of the liquid from fragmentation of cells cultured by any of the above described methods. It is assumed that this is because an almost equivalent amount of PHA synthesizing enzyme exists in a free state in a relatively early stage of culture, which is from the logarithmic growth phase to the early stage of the stationary phase as described above, since the enzyme is actively produced continuously in the cell.

For the inorganic culture medium for use in the above culture methods, any medium containing components enabling microorganisms to be grown such as phosphorous sources (e.g. phosphates) and nitrogen sources (e.g. ammonium salts, nitrates, etc.) may be used, and inorganic culture media may include, for example, a MSB medium, E medium (J. Biol. Chem., 218, 97–106 (1956)) and M9 medium. Furthermore, the composition of the M9 medium for use in Examples of the present invention is as follows:

Na$_2$HPO$_4$: 6.2 g
KH$_2$PO$_4$: 3.0 g
NaCl: 0.5 g
NH$_4$Cl: 1.0 g
(per liter of medium, pH 7.0).

In addition, about 0.3% (v/v) of a solution containing minor components shown below is preferably added in the above inorganic culture medium for ensuring satisfactory growth of the microorganism and production of the PHA synthesizing enzyme:
(Solution Containing Minor Components)
nitrilotriacetic acid: 1.5 g
MgSO$_4$: 3.0 g
MnSO$_4$: 0.5 g
NaCl: 1.0 g
FeSO$_4$: 0.1 g
CaCl$_2$: 0.1 g
CoCl$_2$: 0.1 g
ZnSO$_4$: 0.1 g
CuSO$_4$: 0.1 g
AlK (SO$_4$)$_2$: 0.1 g
H$_3$BO$_3$: 0.1 g
Na$_2$MoO$_4$: 0.1 g
NiCi$_2$: 0.1 g
(per liter)

The culture temperature may be any temperature at which the above microorganism can satisfactorily be grown, for example 14 to 40° C., preferably 20 to 35° C.

Also, a desired PHA synthesizing enzyme can be produced using a transformant having a PHA synthesizing enzyme gene of the aforesaid PHA producing microorganism. Cloning of the PHA synthesizing enzyme gene, preparation of an expression vector, and preparation of the transformant may be carried out in accordance with an established method. In a transformant obtained with a microorganism such as *Escherichia coli* as a host, the medium for use in culture is a natural medium or a synthetic medium, for example, a LB medium, M9 medium or the like. A culture temperature is in the range of from 25 to 37° C. In addition, aerobic culture is conducted for 8 to 27 hours to achieve growth of the microorganism. Thereafter, cells can be collected to collect the PHA synthesizing enzyme accumulated in the cells. Antibiotics such as kanamycin, ampicillin, tetracycline, chloramphenicol and streptomycin may be added in the medium as necessary. Also, in the case where an inductive promoter is used in the expression vector, an inductive material corresponding to the promoter may be added to the medium to promote expression when the transformant is cultured. Such inductive materials include, for example, isopropyl-1-thio-β-D-galactoside (IPTG), tetracycline and indolacrylic acid (IAA).

For the PHA synthesizing enzyme, liquids from fragmentation of cells of microorganism, and crude enzymes such as salted ammonium sulfate obtained by precipitation and collection of protein components with ammonium sulfate and the like may be used, or enzymes purified by various kinds of methods may be used. Stabilizers such as metal salts, glycerin, dithiothreitol, EDTA and bovine serum albumin (BSA), and activators may be added to the enzymes as necessary.

For isolation and purification of PHA synthesizing enzymes, any method allowing enzyme activation of PHA synthesizing enzymes to be retained may be used. For example, obtained cells of microorganism are crushed with a French press, a supersonic crusher, lysozyme, various kinds of surfactants and the like, and thereafter, for a crude enzyme solution obtained by centrifugation or salted ammonium sulfate prepared therefrom, means such as affinity chromatography, cation or anion exchange chromatography, and gel filtration is applied alone or in combination, whereby a purified enzyme can be obtained. In particular, a gene recombination protein can be purified more conveniently by expressing the protein in the form of united protein with "tags" such as histidine residues bound to the N terminal and C terminal, and making the protein to be bound to an affinity resin through these tags. For isolating a desired protein from the united protein, methods of cleaving the linkage by protease such as thrombin and a blood coagulation factor Xa, decrasing the pH, adding a high concentration of imidazole as a competitive binding agent and the like may be used. Alternatively, if the tag includes intein as in the case of using pTYB1 (manufactured by New EnglanBiolab Co., Ltd.) as a expression vector, a reduction condition is achieved by dithiothreitol or the like to cleave the linkage. For the united protein enabling purification by affinity chromatography, glutathione-S-transferase (GST), chitin bound domain (CBD), maltose bound protein (MBP) and thioredoxine (TRX) are also well known in addition to the histidine tag. The GST united protein can be purified by the GST affinity resin.

A various kinds of reported methods may be used for measuring activity of the PHA synthesizing enzyme, and for example, the activity may be measured by the following method in which as a measurement principle, CoA released in the process through which 3-hydroxyacyl CoA is polymerized under the catalytic action of the PHA synthesizing enzyme to form PHA is colored with 5,5'-dithiobis-(2-nitrobenzoic acid) to carry out measurements. Reagent 1: bovine serum albumin (manufactured by Sigma Co., Ltd.) is dissolved in a 0.1 M Tris hydrochloric buffer (pH 8.0) in the concentration of 3.0 mg/ml, Reagent 2: 3-hydroxyoctanoyl CoA is dissolved in a 0.1 M Tris hydrochloric buffer (pH 8.0) in the concentration of 3.0 mM, Reagent 3: trichloroacetic acid is dissolved in a 0.1 M Tris hydrochloric buffer (pH 8.0) in the concentration of 10 mg/ml, and Reagent 4: 5,5'-dithiobis-(2-nitrobenzoic acid) is dissolved in a 0.1 M Tris hydrochloric buffer (pH 8.0) in the concentration of 2.0 mM. First reaction (PHA synthesis reaction): 100 µl of Reagent 1 is added in 100 µl of sample (enzyme) solution and mixed together, and is pre-incubated at 30° C. for a minute. 100 µl of Reagent 2 is added thereto and mixed together, and is incubated at 30° C. for 1 to 30 minutes, followed by adding thereto Reagent 3 to stop the reaction. Second reaction (reaction of coloring free CoA): the first reaction solution of which reaction has been stopped is subjected to centrifugation (15,000×g, 10 minutes), and 500 µl of Reagent 4 is added in 500 µl of supernatant liquid of this solution, and is incubated at 30° C. for 10 minutes, followed by measuring an absorbance at 412 nm. Calculation of enzyme activity: the amount of enzyme for releasing 1 µmol of CoA per minute is defined as one unit (U).

<Preparation of Structure>

An example of a method for producing a structure containing polyhydroxyalkanoate of the present invention at least comprises the steps of: (1) immobilizing on a base material a PHA Synthase containing an amino acid sequence capable of binding to the base material, (2) adding a 3-hydroxyacyl CoA, or a substrate, (3) conducting a PHA synthesis reaction, and (4) processing a structure containing polyhydroxyalkanoate, the structure being coated with the polyhydroxyalkanoate, depending on an application, as required.

An amino acid sequence capable of binding to a base material of the present invention is an amino acid sequence determined by screening of a random peptide library, or an amino acid sequence rationally designed by means of the chemical properties of a base material.

The random peptide libraries of the present invention include a random synthesis peptide library wherein a random peptide is chemically synthesized in a soluble form, a solid phase immobilized peptide library wherein a peptide is synthesized on resin beads, a peptide library wherein a DNA of a random sequence chemically synthesized is biosynthesized in a ribosome in vitro, a phage display peptide library wherein, for example, a random synthesis gene is connected to the N terminal side gene of the surface protein (e.g., the gene III protein) of a M13 base phage, a random peptide library wherein, in a similar way above mentioned, a membrane protein of a microbe, Omp A (Francisco et al., 1993, PNAS, 90, 10444–10448, or Pistor and Hoborn, 1989, Klin. Wochenschr., 66, 110–116), PAL (Fuchs et al., 1991, Bio/Technology, 9, 1369–1372), Lamb (Charbit et al., 1988, Gene, 70, 181–189 and Bradbury et al., 1993, Bio/Technology, 1565–1568), fimbrin (Hedegaard and Klemm, 1989, Gene, 85, 115–124, and Hofnung, 1991, Methods Cell Biol., 34, 77–105) and IgA protease β domain (Klauser et al., 1990, EMBO J., 9, 1991–1999) are fused and presented.

A method of screening an amino acid sequence capable of binding to a base material by means of these random peptide libraries, when a chemical synthesis peptide library is used, involves causing a peptide library to make contact with a base material, removing a peptide incapable of binding to the base material, and subsequently retrieving a peptide binding to the base material to determine the amino acid sequence by use of Edman degradation, etc.

On the other hand, when a phage display peptide library is used, a base material is fixed on a column or plate if the base material is granular, or if a base material is a plate, the aforementioned library is directly added on the base material surface for contact, and then a binding phage is kept and a non-binding phage is washed away. A phage left subsequent to washing is eluted with an acid, etc. After neutralization with a buffer, the phage is incorporated into $E.$ $coli$ to amplify it. Repetition of this selection of a plurality of times concentrates a plurality of clones that are capable of binding to a target base material. At this time, to obtain a single clone, the phage is again allowed incorporated into the $E.$ $coli$ to make a colony on a culture plate. After each single colony is cultured in a liquid culture medium, the phage present in a supernatant of the medium is precipitation purified with polyethylene glycol, or the like. The structure of the peptide is determined by the analysis of this base sequence.

Screening of a peptide capable of binding to a base material by means of a phage display peptide library can be suitably used for this invention in that an operation wherein a phage that bonds more strongly to a base material is concentrated, so called panning, is included so that a more reliable peptide candidate can be selected. The method of forming a phage random peptide library includes, for example, coupling a random synthesis gene to the N terminal side gene of the surface protein (for example the gene III protein) of a M13 base phage. The method has been reported by Scott, J K. and Smith (G P., Science Vol. 249, 389, 1990), Cwirla, S E et al. (Proc. Natl. Acad. Sci. USA Vol. 87, 6378, 1990), etc. The size of a gene to be inserted is not particularly limited if the peptide is stably expressed; however, the size corresponding to the number of amino acids of 6 to 40 (corresponding to a molecular weight of about 600 to 4000) is appropriate in order to cover all the random sequences of a formed library and for these sequences to have binding ability, and of them the size corresponding to 7 to 18 amino acids is preferable.

Where two or more kinds of peptides capable of binding to a base material by screening of a phage display peptide library are obtained, all or part of the amino acid sequence out of at least one peptide selected from the group consisting of these peptides may be combined in series in a suitable combination to prepare a peptide capable of binding to the base material for use. In this case, it is desirable to set up an appropriate spacer sequence between two kinds of amino acid sequences. The spacer sequence preferably has a range of about 3 to about 400 amino acids, and the sequence may contain any amino acid. Most preferably, the spacer sequence is one that does not prevent the function of a PHA synthase or does not disturb the binding of a PHA synthase to a base material.

An amino acid sequence capable of binding to a base material of the present invention is an amino acid sequence determined by screening of a random peptide library, or can also be an amino acid sequence rationally designed by means of the chemical properties of a base material.

The immobilization of a PHA synthase with respect to a base material is established through an amino acid sequence capable of binding to the base material having been fused into the synthase and presented. Enzyme proteins including a PHA synthase are polypeptides of many amino acids combined, which exhibit the properties of an ion adsorbent via free ionic amino acids such as lysine, histidine, arginine, asparagine, and glutamate, and also offer the properties of a hydrophobic adsorbent due to organic polymers and through amino acids having free hydrophobic groups such as alanine, valine, leucine, isoleucine, methionine, tryptophan, phenylalanine, and proline. Accordingly, enzyme proteins can be immobilized on base materials that have hydrophilic, hydrophobic, or both hydrophilic and hydrophobic properties although there are varying degrees of immobilization.

When base materials that primarily present ionic functional groups on their surfaces, for example, inorganic pigments containing clay minerals, metal oxides, etc. as main components are utilized, a PHA synthase can be immobilized by the ionic adsorption method by choosing sequences containing many amino acids having free ionic groups such as lysine, histidine, arginine, asparagine, and glutamate as amino acid sequences capable of binding the base materials to be fused into the synthase and presented.

In addition, when a base material, the surface of which is mainly nonpolar, for example, an inorganic pigment comprising a carbon crystal such as an azo pigment having a plurality of aromatic rings or condensed polycyclic phthalocyanine base pigment, an organic pigment such as an anthraquinone base pigment, or carbon black, is used, a PHA synthase can be immobilized via hydrophobic adsorption by selecting a sequence containing many amino acids having free hydrophobic groups such as alanine, valine, leucine, isoleucine, methionine, tryptophan, phenylalanine, and proline as an amino acid sequence capable of binding the base material to be fused into the synthase and presented.

Amino acid sequences capable of binding to a base material obtained by the aforementioned methods are fused into polyhydroxyalkanoate synthase and utilized by means of usual genetic engineering methods. A peptide capable of binding to respect to a base material can be expressed by connecting the N terminal or C terminal of polyhydroxyalkanoate synthase. Also, it can be expressed by insertion of an appropriate spacer sequence.

A spacer sequence preferably has a range of about 3 to about 400 amino acids, and the sequence may contain any amino acid. Most preferably, a spacer sequence is one that does not prevent the function of a PHA synthase or does not disturb the binding of a PHA synthase to a base material.

Where two or more kinds of peptides capable of binding to a base material by operations such as the above described screening of a phage display peptide library are determined, a mixture of a plural kinds of PHA synthases produced by individually fusing these peptides into a PHA synthase can be utilized in the present invention.

For a method of separating and purifying a PHA synthase containing an amino acid sequence capable of binding to a base material, as described above, any method can be used if it is a way to maintain the enzyme activities of the PHA synthase.

A step of immobilizing a PHA synthase on a base material is achieved by causing a PHA synthase containing an amino acid sequence capable of binding to a base material to make contact with the base material in an aqueous medium.

The composition of the aqueous medium for synthesis of PHA in this step may be any composition that does not interfere the step of carrying out the PHA synthesis reaction, but the composition may be adjusted into a composition allowing the activity of the PHA synthesizing enzyme to be exerted in order to simplify the subsequent steps. As the composition allowing the activity of the PHA enzyme to be exerted, for example, a buffer may be used. For the buffer, general buffers for use in biochemical reactions, for example, acetate buffers, phosphate buffers, potassium phosphate buffers, 3-(N-morpholino) propane sulfonate (MOPS) buffers, N-tris (hydroxymethyl) methyl-3-aminopropane sulfonate (TAPS) buffers, trischloride buffers, glycin buffers, and 2-(cyclohexylamino) ethanesulfonate (CHES) buffers are suitably used. The concentration of the buffer allowing the activity of the PHA synthesizing enzyme to be exerted may be a general concentration, namely in the range of from 5 mM to 1.0 M, but is preferably in the range of from 10 to 200 mM. Also, an adjustment is made so that pH is in the range of from 5.5 to 9.0, preferably from 7.0 to 8.5, but the possibility is not excluded that a pH condition is set in a range other than the above described range depending on the most suitable pH and pH stability of a PHA synthesizing enzyme to be used.

In addition, when the base material is a powder, for maintaining a dispersion condition of the base substrate in the aqueous medium, a suitable surfactant may be added as long as the surfactant has a type and concentration not interfering the subsequent steps. Examples of the surfactant may include, for example, anionic surfactants such as sodium oleate, sodium dodecylsulfonate, sodium dodecyl sulfate, sodium dodecyl-N-sarcosinate, sodium cholate, sodium deoxycholate and sodium taurodeoxycholate; cationic surfactants such as cetyltrimethylammonium bromide and dodecylpyridinium chloride; ampholytic surfactants such as 3-[(choleamidepropyl) dimethylammonio]-1-propanesulfonic acid (CHAPS), 3-[(3-choleamidepropyl) dimethylammonio]-2-hydroxy-1-propanesulfonic acid (CHAPSO), palmitoyllysolecithin and dodecyl-β-alanine; and nonionic surfactants such as octylglucoside, octylthioglucoside, heptylthioglucoside, decanoyl-N-methylglucamide (MEGA-10), polyoxyethylenedodecylether (Brij, Lubrol), polyoxyethylene-i-octylphenylether (Triton X), polyoxyethylenenonylphenylether (Nonidet P-40, Triton N), polyoxyethylene fatty acid ester (Span) and polyoxyethylenesorbitol ester (Tween).

In addition, for maintaining a dispersion of the base material in a state of powder in the aqueous medium, a suitable auxiliary solvent may be added as long as it has a type and concentration not interfering the subsequent steps. For the auxiliary solvent, one or two types of substances selected from, for example, linear aliphatic hydrocarbons such as hexane, and their derivatives such as monovalent alcohols such as methanol and ethanol, polyvalent alcohols such as glycerol, fatty acid ethers and carboxylates may be selected and used.

Immobilization of a PHA synthase on a base material by means of the ion adsorption method or hydrophobic adsorption method can be achieved by admixing a base material with a PHA synthase in a specified aqueous medium so as to give a specified concentration. In this case, the reaction vessel is desirably shook or stirred with a suitable strength so that the enzyme is uniformly adsorbed on the base material surface.

In the immobilization treatment described above, the composition of an aqueous medium of a mixture of a base material and an enzyme is desirably prepared taking into account the fact that the positivity or negativity of the surface charges, the amounts of charge, and hydrophobicity, of the base material and the PHA synthase vary depending on the pH and salt concentration of the aqueous medium. For example, when the base material is mainly ion adsorbent, lowering the salt concentration can increase the amount of charge that contributes the adsorption between the base material and the PHA synthase. In addition, changing the pH can increase the amounts of the opposite charges of the two. When the base material is primarily hydrophobic and adsorbent, increasing the salt concentration can increase the hydrophobicity of the two. Further, the measurement of the wetting angle and the electrophoresis to examine the charge condition and hydrophobicity of the base material and PHA synthase can set up a composition suitable for adsorption. Furthermore, the direct measurement of the amounts of base material and PHA synthase adsorbed can evaluate the composition. An example of the method for measuring the amount of adsorption may include adding a PHA synthase solution of known concentration to a base material, conducting adsorption treatment, and subsequently the PHA synthase concentration in the solution to evaluate the amount of adsorbed enzyme by balance.

In order to supplement the immobilization of an enzyme by the ionic adsorption method or hydrophobic adsorption method, the covalent binding methods may be used when considering the possibility of the activity or inactivity of the enzyme and the complexity of the operation. The methods include, for example, a method of diazotizing a base material having an aromatic amino group and diazo coupling an enzyme to the resulting material, a method of forming a peptide bond between a base material having a carboxyl and an amino group and an enzyme, a method of performing alkylation among a base material having a halogen group, an amino group of an enzyme, and the like, a method of reacting a base material activated by cyanogen bromide with an amino group of an enzyme, a method of crosslinking an amino group of a base material and amino group of an enzyme, a method of reacting a base material having a carboxyl and an amino group with an enzyme in the presence of a compound having an aldehyde or ketone group and an isocyanide compound, and a method of conducting an exchange reaction between a base material with a disulfido group and a thiol group of an enzyme.

An immobilized enzyme produced by a method mentioned above can directly be used and further freeze-dried for use. The time for the immobilization treatment of the enzyme is desirably between 1 minute and 24 hours, more desirably between 10 minutes and 1 hour. Excess standing or leaving is not preferable because it leads to a decrease in enzyme activities.

Where, for example, the base material composes a core of the capsular structure, the amount of phospholipid fixed to the base material may be set in the range of from 10 units (U) to 1,000 units (U), desirably from 50 units (U) to 500 units (U) per 1 g of phospholipid, wherein one unit (U) is defined as the amount of PHA synthesizing enzyme when the amount of CoA released in the reaction through which PHA is synthesized by polymerization of 3-hydroxyacyl CoA equals 1 μmol per minute.

In the step of adding a 3-hydroxyacyl CoA, a substrate, a PHA synthase on the base material surface synthesizes a PHA by the introduction of the aforementioned immobilized enzyme into an aqueous reaction solution containing a 3-hydroxyacyl CoA to become a raw material of a desirable PHA to thereby form a structure, the base material of which is coated with the PHA. The aforementioned aqueous reaction solution should be prepared as a reaction system wherein the activity of the PHA synthase is to be fully performed, and is adjusted from pH 5.5 to pH 9.0 by a buffer solution, preferably from pH 7.0 to pH 8.5. However, other conditions besides the above ranges may be set up, depending on the pH suitability and stability of a PHA synthase to be used. The kind of the buffer solution can be selected, as required, depending on the pH range to be set up, if the activity of the PHA synthase is to be fully performed. Usable buffers for general biochemical reactions include, for example, an acetic acid buffer, phosphoric acid buffer, potassium phosphate buffer, 3-(N-morphorino)propane sulfonic acid (MOPS) buffer, N-tris(hydroxymethyl)methyl-3-aminopropane sulfonic acid (TAPS) buffer, tris-hydrochloric acid buffer, glycine buffer, and 2-(cyclohexylamino)ethane sulfonic acid (CHES) buffer. The concentration of the buffer solution to be used is also not limited if the activity of the PHA synthase to be used is to be fully performed, and is normally from 5.0 mM to 1.0 M, preferably from 0.1 M to 0.2 M. The reaction temperature is set up, as required, depending on the characteristics of a PHA synthase to be used, and is normally from 4° C. to 50° C., preferably from 20° C. to 40° C. However, other conditions besides the above ranges may be set up, depending on the temperature suitability and thermal resistance of a PHA synthase to be used. The reaction time varies with the stability or the like of a PHA synthase to be used, and is normally from 1 minute to 24 hours, preferably is selected, as required, within the range of 30 minutes to 3 hours. The concentration of a 3-hydroxyacyl CoA in the reaction solution is set up, as required, within the range wherein the activity of a PHA synthase to be used is to be fully performed, and is normally from 0.1 mM to 1.0 M, preferably is set up within the range of 0.2 mM to 0,2 M. Additionally, when the concentration of a 3-hydroxyacyl CoA in the reaction solution is high, the pH of the reaction system generally tends to decrease, and so the aforementioned buffer is preferably set up at a slightly higher concentration as well when a 3-hydroxyacyl CoA is set up at a high concentration.

Also, in the above describe step, the composition such as type and concentration of 3-hydroxyacyl CoA in the aqueous reaction solution is changed with time, thereby making it possible to change the composition of the monomer unit of PHA covering the base material in the perpendicular direction of the base material.

The form of this base material with the monomer unit composition changed may be, for example, a form in which the change of the composition of the PHA cover is continuous, and the base material is covered with one layer of PHA having a gradient of composition formed in the perpendicular direction. The production method may be, for example, a method in which 3-hydroxyacyl CoA of different composition is added in the reaction solution while synthesizing PHA.

In addition, as another form, there may be a form in which the composition of the PHA cover is changed by stages, and PHA of different compositions covers the base material in multiple layers. The production method for this form may be a method in which PHA is synthesized with a certain composition of 3-hydroxyacyl CoA, followed by collecting the base material under preparation from the reaction solution on a temporary basis using a washing process or the like, and adding thereto a reaction solution of 3-hydroxyacyl CoA of different composition again, and so on.

The structure obtained by the above described reaction is, as required, given to the washing step. The method of washing is not particularly limited, as long as it does not bring about an undesirable change in the structure against the purpose of production of the structure. When a structure is a capsular structure with its base material being the core and the PHA being the out shell, the unnecessary components contained in the reaction solution can be removed, for example, by precipitating the structure by means of centrifuge separation and removing the supernatant. In this case, further cleaning can also be performed by adding a cleaning agent in which the PHA is not dissolved, such as water, a buffer solution, or methanol, and then running centrifuge separation. In addition, a method such as filtration or the like may be utilized instead of centrifuge separation. On the other hand, a structure is a structure, the plate-like base material of which is coated with a PHA, cleaning can be conducted, for example, by immersing it in an aforementioned cleaning agent. Also, the aforementioned structure can be, as required, given to the drying step. Furthermore, the structure can be treated by various secondary processing, chemical modification, etc. prior to utilization.

For example, a polyhydroxyalkanoate-containing structure having further useful functions and properties can be obtained by subjecting PHA on the surface of the base material to chemical modification. For example, a graft chain is introduced, whereby a polyhydroxyalkanoate-containing structure having various kinds of properties derived from the graft chain can be obtained. If polysiloxane as described later is introduced as a graft chain, for example, a polyhydroxyalkanoate-containing structure having more improved mechanical strength, dispersibility, weather resistance, water repellency (resistance), heat resistance and the like can be obtained. In addition, by having PHA on the surface layer of the base material crosslinked, mechanical strength, chemical resistance, heat resistance and the like of the polyhydroxyalkanoate-containing structure can be improved.

The method for chemical modification is not particularly limited as long as it is a method by which the purpose of obtaining a desired function and structure is achieved, but, for example, a method in which PHA having a reactive functional group on the side chain is synthesized, and chemical modification is accomplished using the chemical reaction of the functional group may be used as a suitable method.

The type of the above described reactive functional group is not particularly limited as long as it serves the purpose of obtaining a desired function and structure, and may be, for example, an epoxy group as described previously. PHA having an epoxy group on the side chain can be chemically converted as in the case of a normal polymer having an epoxy group. Specifically, for example, conversion into a hydroxyl group, and introduction of a sulfone group are possible. Also, a compound having thiol and amine can be added, and for example, a compound having a reactive functional group at the terminal, specifically a compound having an amino group having high reactivity with the epoxy group is added and reacted, whereby the graft chain of polymer is formed.

Compounds having amino groups on the terminals may include, for example, polyvinyl amine, polyethylene imine, and amino modified polymers such as amino modified polysiloxane (amino modified silicone oil). Among them, for amino modified polysiloxane, commercially available modified silicone oil, or amino modified polysiloxane that is synthesized by a method described in J. Amer. Chem. Soc., 78, 2278 (1956) or the like may be used, and the effect of improving mechanical strength, dispersibility, light resistance, weather resistance, water repellency (resistance) and heat resistance and so on by addition of the graft chain of the polymer can be expected.

In addition, another example of chemical conversion of a polymer having an epoxy group is a crosslinking reaction by a diamine compound such as hexamethylenediamine, succinic anhydride, 2-ethyl-4-methylimidazole, or the like, and an example of physicochemical conversion is a crosslinking reaction by irradiation with electron rays or the like. Among them, the reaction between PHA having an epoxy group on the side chain and hexamethylenediamine progresses in accordance with a scheme as described below to produce a crosslinked polymer.

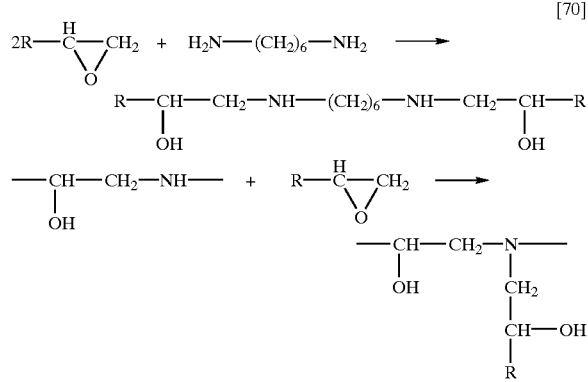

[70]

In polyhydroxyalkanoate-containing structure of the present invention, an enzyme immobilized on a base material has the effect of enhancing the affinity and adhesion between the polyhydroxyalkanoate and the base material to hardly peel off the polyhydroxyalkanoate coating the base material.

In an obtained structure, the method of confirming that the base material is coated with a PHA encompasses, for example, a method of the combination of composition analysis by gas chromatography, or the like and form observation by electron microscopy, or the like, and a method of evaluating the structure from mass spectrum of each composition layer using the time-of-flight secondary ion mass spectrometry analysis apparatus (TOF-SIMS) and ion spattering technology. However, as a further direct, simple, easy confirmation method, a method of the combination of Nile Blue A stain and fluorescence microscope observation, which has been newly developed by the present inventors, can be utilized as well. A study of the present inventors on a method of simply and easily confirming PHA synthesis in vitro using a PHA synthase has shown that Nile Blue A, which is a reagent having the property of specifically binding to a PHA to emit fluorescence and which has been reported in Appl. Environ. Microbiol., 44, 238–241 (1982) that Nile Blue A can be used for the simple confirmation of PHA production in a microbe cell in vivo, can also be utilized for the check of PHA synthesis in vitro by setting up appropriate method of use and use conditions, which has completed the aforementioned method. That is, this method can simply check PHA synthesis in vitro, the method that involves filtering a Nile Blue A solution of a specified concentration, admixing the resulting filtrate with a reaction solution containing a PHA, irradiating the mixture with excited light of a given wavelength by a fluorescence microscope and controlling it, and emitting fluorescence only from the synthesized PHA and observing it. As long as a base material used does not emit fluorescence under the aforementioned conditions, a PHA with which the base material surface is coated can be directly observed and evaluated by applying the aforementioned method to the production of a structure of the present invention.

<Utilization of Structure>

A feature of the present invention has enabled the production of a structure that is difficult to manufacture by an ordinary organic synthetic method. Therefore, the invention can provide a structure having excellent properties that are not exhibited by a capsular structure or laminated structure produced by a conventional organic synthetic process. For example, the invention makes it possible to newly utilize polymeric compounds and provide polymers with new functions and structures, which are difficult to realize by means of conventional organic synthetic approaches. More specifically, new functional polymeric compounds that are difficult to produce by conventional organic synthetic approaches, capsular structures and laminated structures coated with polymeric compounds of extremely high chirality, and the like, can be manufactured by means of extremely simple and easy processes by utilizing extremely precise molecule recognition abilities and stereoselectivity characteristic of catalytic actions of living organisms.

Applications of a structure as mentioned above include, for example, a highly functional capsule toner for electrophotography, microcapsule pigment ink of excellent dispersion stability, an electrophoresis particle for electrophoresis display, and a coloring composition for a color filter.

EXAMPLES

The present invention will be more specifically described below using Examples. However, each of the Examples that will be described below represents one example of the most preferred embodiments of the present invention, but the technical scope of the present invention should not be limited to these Examples.

Reference Example 1

Preparation of Transformant Capable of Producing PHA Synthesizing Enzyme, And Production of PHA Synthesizing Enzyme A transformant capable of producing the PHA synthesizing enzyme was prepared by the following method.

The YN2 strain was cultured on 100 ml of LB culture medium (1% polypeptone, 0.5% yeast extract, 0.5% sodium chloride, pH 7.4) at 30° C. overnight, followed by isolating and collecting chromosome DNA using a method by Marmer, et al. The obtained chromosome DNA was fully decomposed with a restriction enzyme Hind III. pUC18 was as a vector and cleaved by the restriction enzyme Hind III. Dephosphorylation of the terminal (Molecular Cloning, 1, 572, (1989); Cold Spring Harbor Laboratory Press.) was carried out, and thereafter DNA Ligation Kit Ver. 11 (Takara Shuzo Co., Ltd.) was used to couple the cleaved site (cloning site) of the vector to the Hind III fully decomposed fragment of the chromosome DNA. A plasmid vector with this chromosome DNA fragment incorporated therein was used to transform the Escherichia coli HB101 strain to prepare a DNA library of the YN2 strain.

Then, for selecting the DNA fragment including the PHA synthesizing enzyme gene of the YN2 strain, a probe for colony hybridization was prepared. Oligonucleotides composed of base sequences of SEQ ID NO:5 and SEQ ID NO:6 were synthesized (Amasham Pharmacia.Biotech), and these oligonucleotides were used as primers to carry out PCR with the chromosome DNA as a template. The PCR-amplified DNA fragment was used as a probe. The labeling of the probe was carried out using the commercially available labeling enzyme AlkPhosDirect (Amasham Pharmacia.Biotech). The obtained labeled probe was used to select Escherichia coli strains having recombinant plasmids including PHA synthesizing enzyme genes from the chromosome DNA library of YN2 strains by the colony hybridization method. Plasmids were collected from the selected strains by the alkali method, whereby the DNA fragment including the PHA synthesizing enzyme gene can be obtained.

The gene DNA fragment obtained here was recombined into a vector PBBR 122 (Mo Bi Tec) including a broad-host-range replication region belonging to none of Inc P, Inc Q and Inc W constituting an incompatibility group. When this recombinant plasmid was transformed into the Pseudomonas cichorii YN2 ml strain (strain lacking PHA synthesis capability) by the Electroporation method, PHA synthesizing capability of the YN2 ml strain was recovered, thus exhibiting complement property. Thus, it is ensured that the selected gene DNA fragment includes a PHA synthesizing enzyme gene domain capable of being translated into the PHA synthesizing enzyme in Pseudomonas cichorii YN2 ml strain.

For this DNA fragment including the PHA synthesizing enzyme gene, base sequences were determined by the Sanger's method. As a result, it was found that in the determined base sequences, there existed base sequences expressed by SEQ ID NO:2 and SEQ ID NO:4, each coding a peptide. As described below, it could be ensured that the proteins composed of individual peptide chains all had enzyme activity, and the base sequences expressed by SEQ ID NO:2 and SEQ ID NO:4 were PHA synthesizing enzymes. Specifically, it was ensured that the base sequence of SEQ ID NO:2 coded the amino acid sequence expressed by SEQ ID NO:1, and the base sequence of SEQ ID NO:4 coded the amino acid sequence expressed by SEQ ID NO:3, and the PHA synthesis capability can be exhibited with a protein having only any one of these amino acid sequences.

For the PHA synthesizing enzyme gene of base sequence expressed by SEQ ID NO:2, PCR was carried out with Chromosome DNA as a template to reprepare the full length of the PHA synthesizing enzyme.

For the base sequence expressed by SEQ ID NO:2, oligonucleotide having base sequences upstream to its initiation codon (SEQ ID NO:7), which serves as an upstream primer, and oligonucleotide having base sequences downstream to its stop codon (SEQ ID NO:8), which serves as a downstream primer were designed and synthesized, respectively (Amasham Pharmacia.Biotech) Using these oligonucleotides as primers, PCR was carried out with chromosome DNA as a template to amplify the full length of the PHA synthesizing enzyme gene (LA-PCR Kit; Takara Shuzo Co., Ltd.)

In a similar way, for the PHA synthesizing enzyme gene of base sequence expressed by SEQ ID NO:4, PCR was carried out with Chromosome DNA as a template to repreparate the full length enzyme of the PHA synthesizing enzyme. For the base sequence expressed by SEQ ID NO:4, oligonucleotide having base sequences upstream to its initiation codon (SEQ ID NO:9), which serves as an upstream primer, and oligonucleotide having base sequences downstream to its stop codon (SEQ ID NO:10), which serves as a downstream primer were designed and synthesized, respectively (Amasham Pharmacia.Biotech). Using this oligonucleotide as a primer, PCR was carried out to amplify the full length gene of the PHA synthesizing enzyme (LA-PCR Kit; Takara Shuzo Co., Ltd.)

Then, PCR amplified fragment including the obtained full length gene of PHA synthesizing enzyme were each fully decomposed using the restriction enzyme Hind III. In addition, the expression vector pTrc99A was also cleaved with the restriction enzyme Hind III, and was subjected to dephosphorylation processing (Molecular Cloning, vol. 1, p. 572, 1989; Cold Spring Harbor Laboratory Press). A DNA fragment including the full length gene of the PHA synthesizing enzyme gene with unnecessary base sequences at both terminals removed was coupled to the cleaved site of this expression vector pTrc99A using DNA Ligation Kit Ver. II (Takara Shuzo Co., Ltd.).

Escherichia coli (HB101: Takara Shuzo Co., Ltd.) was transformed by a potassium chloride method using the obtained recombinant plasmid. The obtained recombinant was cultured, amplification of recombinant plasmid was carried out, and the recombinant plasmid was collected for each type. The recombinant plasmid retaining gene DNA of SEQ ID NO:2 was defined as pYN2-C1 (derived from SEQ ID NO:2), and the recombinant plasmid retaining gene DNA of SEQ ID NO:4 was defined as pYN2-C2 (derived from SEQ ID NO:4).

Escherichia coli (strain HB101fB, fadB deficient mutant) was transformed by a potassium chloride method using pYN2-C1 and pYN2-C2 to obtain recombinant Escherichia coli strains, a pYN2-C1 recombinant strain and a pYN2-C2 recombinant strain each having its own recombinant plasmid.

The pYN2-C1 recombinant strain and pYN2-C2 recombinant strain were each plated in 200 ml of M9 medium containing 0.5% of yeast extract and 0.1% of octanoic acid, and were subjected to shaking culture at 37° C. and 125 strokes/minute. After 24 hours, cells were collected by centrifugation, and plasmid DNA was collected using an ordinary method.

For pYN2-C1, oligonucleotide serving as an upstream primer (SEQ ID NO:11) and oligonucleotide serving as a downstream primer (SEQ ID NO:12) were each designed and synthesized (Amasham Pharmacia-Biotech) Using these oligonucleotides as primers, PCR was carried out with pYN2-C1 as a template to amplify the full length gene of the PHA synthesizing enzyme having the BamHI and SacI restriction sites in the upstream and the SpeI and XhoI restriction sites in the downstream (LA-PCR Kit; Takara Shuzo Co., Ltd.).

In a similar way, for pYN2-C2, oligonucleotide serving as an upstream primer (SEQ ID NO:13) and oligonucleotide serving as a downstream primer (SEQ ID NO:14) were each designed and synthesized (Amasham Pharmacia.Biotech). Using this oligonucleotide as a primer, PCR was carried out with pYN2-C2 as a template to amplify the full length gene of the PHA synthesizing enzyme having the BamHI restriction site in the upstream and the XhoI restriction site in the downstream (LA-PCR Kit; Takara Shuzo Co., Ltd.).

Each of purified PCR amplified products was digested by BamHI and XhoI, and was inserted into a corresponding site of plasmid pGEX-6P-1 (manufactured by Amasham PharmaciaBiotech Co., Ltd.). These vectors (pGEX-C1 and pGEX-C2) were used to transform *Escherichia coli* (JM109) to obtain a strain for expression. The strain was checked with DNA fragments obtained by treating with BamHI and XhoI plasmid DNA prepared in large quantity using Miniprep (Wizard Minipreps DNA Purification Systems, manufactured by PROMEGA Co., Ltd.). The obtained strain was pre-cultured in 10 mL of LB-Amp medium overnight, and thereafter 0.1 mL of the strain was added in 10 mL of LB-Amp medium, and was shaking-cultured at 170 rpm at 37° C. for 3 hours. Thereafter, IPTG was added (at a final concentration of 1 mM), and culture was continuously carried out at 37° C. for 4 to 12 hours.

IPTG-induced *Escherichia coli* was collected (8,000×g, 2 minutes, 4° C.), and was resuspended in 1 ml of PBS at 4° C. The cells were crushed by freezing and thawing and sonication, and were subjected to centrifugation (8,000×g, 10 minutes, 4° C.) to remove cell debris. The presence of desired expression proteins in the supernatant (cell-free extract) was confirmed with SDS-PAGE, followed by purifying the induced and expressed GST fused protein with Glutathion Sepharose 4B beads (manufactured by Amasham Pharmacia.Biotech Co., Ltd.).

The glutathion sepharose for use in the purification was treated in order to avoid nonspecific adsorption in advance. Specifically, the glutathion sepharose was washed three times with the same amount of PBS (8,000×g, 1 minute, 4° C.), and thereafter the same amount of PBS containing 4% BSA was added to treat the glutathion sepharose at 4° C. for 1 hour. After treatment, the glutathion sepharose was washed two times with the same amount of PBS, and was resuspended in ½ in quantity of PBS. 40 μL of pretreated glutathion sepharose was added to 1 mL of cell-free extract and stirred gently at 4° C. Thereby, the fused proteins GST-YN2-C1 and GST-YN2-C2 were adsorbed to glutathion sepharose.

After they were adsorbed, glutathion sepharose was collected by centrifugation (8,000×g, 1 minute, 4° C.), and was washed three times with 400 μL of PBS. Thereafter, 40 μL of 10 mM of reduced glutathion was added, and was stirred at 4° C. for 1 hour to elute the adsorbed fused protein. The supernatant was collected after centrifugation (8,000×g, 2 minutes, 4° C.), and thereafter dialysis was conducted against PBS to purify the GST fused protein. It was confirmed by SDS-PAGE that the protein exhibited a single band.

500 μg of each GST fused protein was digested by PreScission protease (Amasham Pharmacia-Biotech, 5U), and was thereafter passed through glutathion sepharose to remove the protease and GST. Flow-through fractions were further processed with a sephadex G200 column equilibrated with PBS to obtain final purified expression proteins YN2-C1 and Yn2-C2. It was confirmed by SDS-PAGE that they exhibited single bands of 60.8 kDa and 61.5 kDa, respectively.

Each purified enzyme solution was concentrated using a biological solution sample concentrating agent (Mizubutorikun AB-1100, manufactured by Ato Co., Ltd.) to obtain 10 U/ml of purified enzyme solution.

The activity of each purified enzyme was measured by the aforesaid method. Also, the concentrations of proteins in the sample were measured by the Micro BCA protein quantification reagent kit (Pierce Chemical Co., Ltd.). The result of measuring the activity of each purified enzyme is shown in Table 1.

TABLE 1

|  | Activity | Specific Activity |
|---|---|---|
| YN2-C1 | 2.1 U/mL | 4.1 U/mg Protein |
| YN2-C2 | 1.5 U/mL | 3.6 U/mg Protein |

Reference Example 2

Synthesis of 3-Hydroxy Acyl-CoA (R)-3-hydroxy octanoyl-CoA was prepared by the following method, based on Rehm BHA, Kruger N, Steinbuchel A (1998) Journal of Biological Chemistry 273 pp24044–24051, being added with some modification. Acyl-CoA synthetase (manufactured by Sigma-Aldrich Com.) was dissolved in tris-hydrochloric acid buffer solution (50 mM, pH 7.5) containing ATP 2 mM, $MgCl_2$ 5 mM, coenzyme A 2 mM, and (R)-3-hydroxyoctanoate 2 mM so as to obtain the resulting solution of 0.1 miliunit/microliter. The solution was incubated in a 37-degree C. of warm bath, and was sampled timely so that progress of a reaction might be analyzed by HPLC. Sulfuric acid was added into a sampled reaction solution to obtain a concentration of 0.02 N to terminate enzyme reaction, and subsequently (R)-3-hydroxyoctanoate that was unreacted substrate was removed by extraction with n-heptane. In analysis by HPLC, RP18 column (nucleosil C18, 7 micrometers, Knauser) was used, elution was conducted with a linear density gradient of acetonitrile using 25 mM phosphate buffer solution (pH 5.3) as a mobile phase, and an absorption spectrum of 200 to 500 nm was monitored with a diode array detector to detect thioester compounds generated by enzyme reaction. (R)-3-hydroxy-5-phenyl valeryl CoA and (R)-3-hydroxy-5-(4-fluorophenyl) valeryl CoA were prepared in a same procedure.

Example 1

Obtaining of an Amino Acid Sequence Having a Binding Affinity to Copper Phthalocyanine (1) Copper phthalocyanine (alpha type: Tokyo Kasei Kogyo Co., Ltd.) was suspended into methanol to obtain a concentration of 5 mg/ml. The suspension 1.5 ml was applied to a plate made of polystyrene, and methanol was removed by evaporation, whereby a coating of copper phthalocyanine was fixed on the surface of the plate made of polystyrene. It was confirmed that the coating of copper phthalocyanine fixed was not removed off even if it was washed with TBS buffer (50 mM Tris-HCl pH7.5 150 mM NaCl) including 0.1% Tween-20.

(2) A blocking buffer containing bovine serum albumin (BSA) (0.1 M $NaHCO_3$ (pH 8.6), 5 mg/ml BSA, 0.1 mg/ml streptavidin, 0.02% $NaN_3$) was filled on the polystyrene plate with copper phthalocyanine fixed thereon, and kept still standing at 4° C. for one hour. The blocking buffer was then discarded and the plate was washed 10 times by TBST buffer (TBS buffer +0.1% Tween-20).

(3) An equivalent for 1.4×10¹¹ pfu of Ph.D.-7 phage display peptide library (manufactured by New England BioLabs Inc.) was added to the plate, which was kept still standing for 60 minutes at 25° C.

(4) The solution of the plate was discarded and the plate was washed 10 times by TBST buffer.

(5) After elution buffer (0.2 M Glycine-HCl (pH 2.2) 1 mg/ml BSA) 1 ml was added and the solution was kept still standing for 3 minutes, the solution was moved into a microdose centrifugation tube, and then 1 M Tris-HCl of 150 µl (pH 9.1) was added. The solution was neutralization to obtain an eluted phage.

(6) *Escherichia coli* ER2537 (manufactured by New England BioLabs Inc.) in early stages of a logarithmic growth was infected with the eluted phage, and was the phage amplified. It was cultured at 37° C. for 4.5 hours. Subsequently, the phage was separated from cell by centrifugation, and purified by precipitation with polyethylene glycol. The phage purified and amplified was suspended in TBS buffer, and was measured for a titer by infection with suitable dilution series to *Escherichia coli*.

(7) Above described procedures (1) to (6) were repeated further 3 times using the amplified phage. However, a concentration of Tween-20 in TBST buffer to be used was raised to 0.5%, and conditions of washing were made severer.

In second time henceforth the same operation was conducted also to samples in which only blocking by BSA to plates made of polystyrene was conducted, and it was used as controls. Titers of the phage eluted in each cycle are shown in Table 2.

TABLE 2

Titer of phages eluted in each cycle

| | Stock solution (A) | Control bond (B) | Phthalocyanine bond (C) | C/A | C/B |
|---|---|---|---|---|---|
| First time | $1.4 \times 10^{11}$ | | $5 \times 10^5$ | $3.6 \times 10^{-6}$ | |
| Second time | $6.5 \times 10^{11}$ | $8.5 \times 10^5$ | $2.6 \times 10^6$ | $4 \times 10^{-6}$ | 3 |
| Third time | $6.0 \times 10^{11}$ | $1.2 \times 10^6$ | $1 \times 10^9$ | $1.6 \times 10^{-3}$ | 800 |
| Fourth time | $8.5 \times 10^{11}$ | $2 \times 10^6$ | $5.3 \times 10^9$ | $6.2 \times 10^{-3}$ | 2700 |

(Unit of A, B, and C is represented by pfu/ml)

Cloning was performed by making *Escherichia coli* of large excess be infected with the phage eluted finally. After infecting *Escherichia coli* with each clone and amplifying the clone, ssDNA was prepared, a base sequence of random domain was decoded and a peptide displayed was sequenced. Amino acid sequence and frequency of 30 clones that were picked up then are shown in Table 3.

TABLE 3

Determined amino acid sequence and frequency

| Determined amino acid sequence | Number (A) | Frequency (A/30) |
|---|---|---|
| SEQ ID No: 15 VFHKLVW Val-Phe-His-Lys-Leu-Val-Trp | 23 | 0.77 |
| SEQ ID No: 182 | 5 | 0.16 |

TABLE 3-continued

Determined amino acid sequence and frequency

| Determined amino acid sequence | Number (A) | Frequency (A/30) |
|---|---|---|
| VYHRLVN Val-Tyr-His-Arg-Leu-Val-Asn SEQ ID No: 183 VIHRLVW Val-Ile-His-Arg-Leu-Val-Trp | 2 | 0.07 |

A copper phthalocyanine binding motif of amino acid sequence VXHXLVX (SEQ ID NO:178), particularly an amino acid sequence VFHKLVW (SEQ ID NO:15) having affinity to a copper phthalocyanine has been determined.

Example 2

Preparation of PHA Synthase Having a Binding Affinity to Copper Phthalocyanine

*Escherichia coli* expression vector expressed via a spacer sequence GGGS (SEQ ID NO:177) by fusing a copper phthalocyanine affinity sequence of amino acid sequence VFHKLVW (SEQ ID NO:15) with N terminal of PHA synthase was built as follows. DNA that encodes this amino acid sequence is manufactured as a double stranded synthetic oligonucleotide, and ligated to suitable restriction cleavage site (BamHI and SacI) of pGEX-C1 plasmid. In this case, according to a description of manufacturer, two synthetic oligonucleotides O1 (5' GATCCGTGTTCCA-CAAATTAGTGTGGGGTGGAGG TTCGGAGCT, SEQ ID NO:16) and O2 (5' CCGAACCTCCACCCCACACTAATTTGTGGAACACG, SEQ ID NO:17) were phosphorylated using T4 polynucleotide kinase (manufactured by Gibco). It was heated at 80° C. for 5 minutes continuously, and then was left to cool slowly to room temperature. This double stranded DNA fragment was directly used for subsequent cloning procedure.

Plasmid pGEX-C1 was digested by BamHI and SacI, and the above described double stranded DNA fragment was inserted. An *Escherichia coli* (JM109) was transformed using this vector, and a strain for expression was obtained. Check of the strain was conducted by determining a base sequence of insertion by sequencing using pGEX5' Sequencing Primer (manufactured by Amasham Pharmasia Biotech Corp.) and using a plasmid DNA prepared by Miniprep (Wizard Minipreps DNA Purification Systems, manufactured by PROMEGA) as a template. After carrying out pre-culture of the obtained strain by LB-Amp culture medium 10 mL overnight, 0.1 mL of a resultant containing the strain was added to LB-Amp culture medium of 10 mL, and a shake culture was carried out at 37° C. and 170 rpm for 3 hours. IPTG was then added (final concentration 1 mM), and cultivation was continued at 37° C. for 4 to 12 hours.

IPTG induced *Escherichia coli* was harvested (8000×g, 2 minutes, 4° C.), and it was re-suspended in 4-degree C. PBS of 1/10 amount. Cell was crushed by freeze thawing and sonication, cell debris was removed by centrifugation (8000×g, 10 minutes, 4° C.). After it was confirmed by SDS-PAGE that target expression protein existed in supernatant, GST fusion protein induced and expressed was purified with glutathione Sepharose 4B (Glutathione Sepharose 4B beads: manufactured by Amasham Pharmasia Biotech Corp.)

Treatment controlling nonspecific adsorption was beforehand given to a glutathione sepharose used. That is, after the glutathione sepharose was washed (8000×g, 1 minute, 4° C.) 3 times by a same amount of PBS, it was treated with a same amount of PBS including 4% BSA added at 4° C. for 1 hour. It was washed twice by same amount of PBS after treatment, and was re-suspended in ½ amount of PBS. The pretreated glutathione sepharose 40 μl was added to a cell free extract 1 mL, and calmly stirred at 4° C. Thereby, the fusion protein GST-YN2-C1 was adsorbed to the glutathione sepharose.

The glutathione sepharose was collected by centrifugation (8000×g, 1 minute, 4° C.) after adsorption, and washing was performed 3 times with PBS 400 μL. Subsequently, 10 mM reduced glutathione 40 μL was added and the solution was stirred at 4° C. for 1 hour and the fusion protein adsorbed was eluted out. After centrifugation (8000×g, 2 minutes, 4° C.), supernatants were collected, and dialyzed to PBS to purify GST fusion protein. It was confirmed that a single band was given by SDS-PAGE.

After each GST fusion protein 500 μg was digested by PreScission protease (Amasham Pharmasia Biotech Corp., 5U), the protease and GST were removed through glutathione sepharose. Flow through fraction was further processed by Sephadex G200 column equilibrated by PBS to obtain a final purified expression protein YN2-C1 (pht). It was confirmed that a single band of 61.9 kDa was given by SDS-PAGE.

Purified enzyme activity was measured by the above described procedure. Moreover, a protein concentration in samples was measured with micro BCA protein determination reagent kit (manufactured by Pierce Chemical com.) Enzyme concentration was 1.9 U/ml and specific activity was 4.0 U/mg protein. Purified enzyme was concentrated using organism solution sample concentration agent (Mizubutorikun AB-1100, manufactured by ATTO Corporation) to obtain 10 U/ml purified enzyme solution.

Example 3

Evaluation of a Binding Affinity to Copper Phthalocyanine

Copper phthalocyanine was suspended in TBS buffer containing 0.1% Tween-20 so that it might give 0.5% (w/v). This suspension 10 ml was sampled into a centrifuge tube made of Teflon, equivalent for 0.5U of PHA synthase YN2-C1 (pht) prepared in Example 2 and YN2-C1 prepared in Reference Example 1 were added to this suspension, which was shaken for 30 minutes at room temperature. By centrifugation operation (for 10,000×g, 4° C., and 10 minutes), copper phthalocyanine particles were collected as a precipitation and separated from supernatant containing enzyme not binding to copper phthalocyanine. The copper phthalocyanine was again suspended into TBS buffer containing 0.1% Tween-20, a centrifugal operation was repeated, whereby the copper phthalocyanine was washed. Results of having measured an enzyme activity of the suspension of the washed copper phthalocyanine are shown in Table 4.

TABLE 4

| Evaluation of binding affinity of enzyme to copper phthalocyanine | |
|---|---|
| | Activity U |
| YN2-C1(pht) | 0.04 |
| YN2-C1 | 0.01 |

It was confirmed that the enzyme YN2-C1 (pht) fused with a copper phthalocyanine affinity sequence had a higher enzyme activity compared with the enzyme YN2-C1 of control, and thus could be effectively immobilized on a base material surface.

Example 4

PHA Capsular Structure of Copper Phthalocyanine

Copper phthalocyanine was suspended in TBS buffer containing 0.1% Tween-20 so that it might give 0.5% (w/v). The suspension 10 ml was sampled into a centrifuge tube made of Teflon, and an equivalent for 0.5U of PHA synthase YN2-C1 (pht) or YN2-C1 was added hereto, and the tube was shaken for 30 minutes at room temperature. Once, copper phthalocyanine was collected by a centrifugation operation, and again this was suspended into TBS buffer containing 0.1% Tween-20 so that it might give 0.5% (w/v). Subsequently, (R)-3-hydroxy octanoyl CoA prepared in Reference Example 2 was added so that it might give a final concentration of 5 mM. Synthetic reaction was conducted by incubating for 30 minutes at 37° C.

PHA generated in the reaction mixture was dyed by Nile blue A, and was observed by a fluorescence microscope. In a sample in which YN2-C1 was added, free PHA granule was observed. In a sample in which YN2-C1 (pht) was added on the other hand, free PHA granule was not observed, and thereby it was confirmed that an efficient PHA synthesis by synthase had been performed.

The reaction mixture was separated by centrifugation (10,000×g, 4° C., and 10 minutes), and a hydrous cake with capsular structure having copper phthalocyanine therein as core was obtained. After re-suspension of this hydrous cake in water, the capsular structure was again collected by a centrifugation operation. Washing was carried out by repeating this operation 3 times.

Figure 1B:
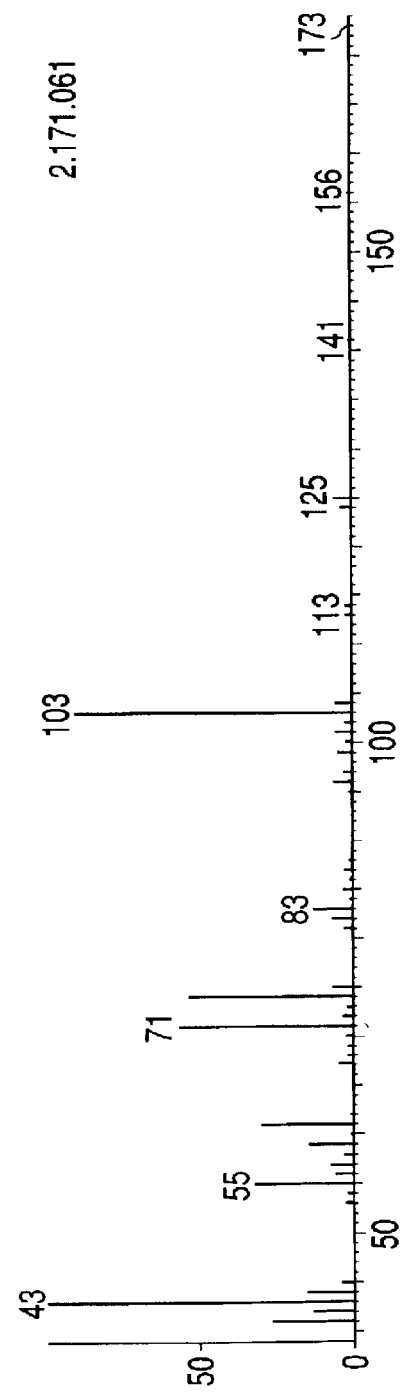

A part of the hydrous cake of the manufactured capsular structure was vacuum dried, suspended in chloroform 20 ml, and the suspension was stirred at 60° C. for 20 hours to extract PHA forming a pellicle. Extract was filtered by a membrane filter of 0.45 micrometers of pore size, vacuum concentration was carried out by a rotating evaporator, and, subsequently methanolysis was conducted according to a conventional method. Resultant product was analyzed by a gas chromatography-mass spectrometry equipment (GC-MS, Shimadzu QP-5050, EI method) to identify methyl esterified PHA monomer unit. As a result, it was confirmed that the PHA concerned was a PHA having 3-hydroxyoctanoic acid as a monomer unit as shown in FIGS. 1A and 1B. Moreover, the PHA was evaluated for a molecular weight by a gel permeation chromatography (GPC; TOSOH CORPORATION HLC-8020, column; Polymer Laboratory PLgel MIXED-C (5 micrometers), solvent; chloroform, column temperature; 40° C., polystyrene calibrated), and Mn=21,000 and Mw=40,000 were given.

Example 5

Obtaining of an Amino Acid Sequence Having a Binding Affinity to Carbon Black (1) Carbon black (Sigma Aldrich Japan Inc.) was suspended in methanol to give a concentration of 5 mg/ml. This suspension 1.5 ml was applied to a polystyrene plate, and methanol was removed by vaporization to obtain a coating of carbon black fixed to a surface of the polystyrene plate. It was confirmed that the carbon black fixed was not removed off even if it was washed with a TBS buffer (50 mM Tris-HCl pH 7.5 150 mM NaCl) including 0.1% Tween-20.

(2) A blocking buffer containing bovine serum albumin (BSA) (0.1 M NaHCO$_3$ (pH 8.6), 5 mg/ml BSA, 0.1 mg/ml streptavidin, 0.02% NaN$_3$) was filled on the polystyrene plate with carbon black fixed thereon, and the plate was kept still standing at 4° C. for one hour. The blocking buffer was then discarded and the plate was washed 10 times by TBST buffer (TBS buffer +0.1% Tween-20).

(3) An equivalent for 1.4×10$^{11}$ pfu of Ph.D.-7 phage display peptide library (manufactured by New England BioLabs Inc.) was added to the plate, which was kept still standing for 60 minutes at 25° C.

(4) The solution of the plate was discarded and the plate was washed 10 times by TBST buffer.

(5) After elution buffer (0.2 M Glycine-HCl (pH 2.2) 1 mg/ml BSA) 1 ml was added and the solution was kept still standing for 3 minutes, the solution was moved into a microdose centrifugation tube, and then 1M Tris-HCl of 150 μl (pH 9.1) was added for neutralization to obtain an eluted phage.

(6) Escherichia coli ER2537 (manufactured by New England BioLabs Inc.) in early stages of logarithmic growth was infected with the eluted phage, and the phage was amplified. It was cultured at 37° C. for 4.5 hours. Subsequently, the phage was separated from cell by a centrifugation, and purified by precipitation in polyethylene glycol. The phage purified and amplified was suspended in TBS buffer, and a titer was measured by infecting *Escherichia coli* with a suitable dilution series.

(7) The above described procedures (1) to (6) were repeated further 3 times using the amplified phage. However, a concentration of Tween-20 in TBST buffer to be used was raised to 0.5%, and conditions of washing were made severer. In second times henceforth the same operation was conducted also to samples in which only blocking by BSA to plates made of polystyrene was conducted, and it was used as controls. Titers of phage eluted in each cycle are shown in Table 5.

TABLE 5

Titer of phages eluted in each cycle

| | Stock solution (A) | Control bond (B) | Carbon black bond (C) | C/A | C/B |
|---|---|---|---|---|---|
| First time | 1.4 × 10$^{11}$ | | 3.0 × 10$^5$ | 2.1 × 10$^{-6}$ | |
| Second time | 6.4 × 10$^{11}$ | 7.5 × 10$^5$ | 1.6 × 10$^6$ | 2.5 × 10$^{-6}$ | 2 |
| Third time | 6.5 × 10$^{11}$ | 1.4 × 10$^6$ | 1.4 × 10$^9$ | 2.2 × 10$^{-3}$ | 1000 |
| Fourth time | 8.4 × 10$^{11}$ | 2.3 × 10$^6$ | 5.6 × 10$^9$ | 6.7 × 10$^{-3}$ | 2400 |

(Unit of A, B, and C is represented by pfu/ml)

A large excessive *Escherichia coli* was infected with the finally eluted phage, and the phage was cloned. After infecting each clone to *Escherichia coli* and amplifying, ssDNA was prepared, a base sequence of random domain was decoded and an amino acid sequence of peptide displayed was determined. Amino acid sequence and frequency of 30 clones that were picked up then are shown in Table 6.

TABLE 6

Determined amino acid sequence and frequency

| Determined amino acid sequence | Number (A) | Frequency (A/30) |
|---|---|---|
| SEQ ID NO: 18 WFWILVN Trp-Phe-Trp-Ile-Leu-Val-Asn | 25 | 0.83 |
| SEQ ID NO: 184 WYWILTN Trp-Tyr-Trp-Ile-Leu-Thr-Asn | 5 | 0.17 |

A carbon black binding motif having amino acid sequence WXWILXN (SEQ ID NO:179), particularly an amino acid sequence WFWILVN (SEQ ID NO:18) having affinity to a carbon black has been determined.

Example 6

Preparation of a PHA Synthase Having a Binding Affinity to Carbon Black

*Escherichia coli* expression vector expressed via a spacer sequence GGGS (SEQ ID NO:177) by fusing a carbon black affinity sequence of amino acid sequence WFWILVN (SEQ ID NO:18) with C terminal of PHA synthase was built as follows. DNA that encodes this amino acid sequence is manufactured as a double stranded synthetic oligonucleotide, and carries out ligation to a suitable restriction cleavage site (SpeI and XhoI) of pGEX-C2 plasmid. In this case, according to a description of manufacturer, two synthetic oligonucleotides O3 (5' CTAGTT GGTTCTGGATTTTAGTGAACGGTGGAGGTTCGC, SEQ ID NO:19) and O4 (5' TCGA GCGAACCTCCACCGTTCACTAAAATCCAGAACCAA, SEQ ID NO:20) were phosphorylated using T4 polynucleotide kinase (manufactured by Gibco). It was heated for 5 minutes at 80° C. continuously, and then was left to cool slowly to room temperature. This double stranded DNA fragment was directly used for subsequent cloning. The plasmid pGEX-C2 was digested by SpeI and XhoI, and the above described double stranded DNA fragment was inserted. *Escherichia coli* (JM109) was transformed using the vector, and a strain for expression was obtained. Check of the strain was conducted by determining a base sequence of insertion by a sequencing using pGEX3' Sequencing Primer (manufactured by Amasham Pharmasia Biotech Corp.) and using a plasmid DNA prepared by Miniprep (Wizard Minipreps DNA Purification Systems, manufactured by PROMEGA) as a template. After carrying out pre-culture of the obtained strain by LB-Amp culture medium 10 mL overnight, 0.1 mL of a resultant containing the strain was added to LB-Amp culture medium of 10 mL, and shake culture was carried out at 37° C. and 170 rpm for 3 hours. IPTG was then added (final concentration 1 mM), and culture was continued at 37° C. for 4 to 12 hours.

IPTG induced *Escherichia coli* was harvested (8000×g, 2 minutes, 4° C.), and it was re-suspended in 4-degree C. PBS of ¹/₁₀ amount. Cell was crushed by freeze thawing and sonication, cell debris was removed by centrifugation (8000×g, 10 minutes, 4° C.). After it was confirmed by SDS-PAGE that a target expression protein exists in supernatant, GST fusion protein induced and expressed was purified with glutathione Sepharose 4B (Glutathion Sepharose 4B beads: manufactured by Amasham Pharmasia Biotech Corp.)

A treatment controlling nonspecific adsorption was beforehand given to glutathione sepharose used. That is, after the glutathione sepharose was washed (8000×g, 1 minute, 4° C.) 3 times by a same amount of PBS, it was treated with a same amount of PBS including 4% BSA added at 4° C. for 1 hour. It was washed twice by a same amount of PBS after treatment, and was re-suspended in ½ amount of PBS. The pretreated glutathione sepharose 40 µl was added to a cell free extract 1 mL, and the solution was calmly stirred at 4° C. Thereby, the fusion protein GST-YN2-C1 adsorbed to the glutathione sepharose.

The glutathione sepharoses were collected by centrifugation (8000×g, 1 minute, 4° C.) after adsorption, and washing was performed 3 times with PBS 400 µL. Subsequently, 10 mM glutathione 40 µL was added and the solution was stirred at 4° C. for 1 hour and the fusion protein adsorbed was eluted out. After centrifugation (8000×g, 2 minutes, 4° C.), supernatants were collected, and dialyzed to PBS to purify the GST fusion protein. It was confirmed that a single band was given by SDS-PAGE.

After each of the GST fusion protein 500 µg was digested by PreScission protease (Amasham Pharmasia Biotech Corp., 5U), the protease and GST were removed through glutathione sepharose. Flow through fraction was further processed by Sephadex G200 column equilibrated by PBS to obtain a final purified expression protein YN2-C2 (cb). It was confirmed that a single band of 61.9 kDa was given by SDS-PAGE.

Purified enzyme activity was measured by the above described procedure. Moreover, a protein concentration in samples was measured with micro BCA protein determination reagent kit (manufactured by Pierce Chemical com.) Enzyme concentration was 2.1 U/ml and specific activity was 4.1 U/mg protein. Purified enzyme was concentrated using organism solution sample concentration agent (Mizubutorikun AB-1100, manufactured by ATTO Corporation) to obtain 10 U/ml purified enzyme solution.

Example 7

Evaluation of a Binding Affinity to Carbon Black

Carbon black was suspended in TBS buffer containing 0.1% Tween-20 so that it might give 0.5% (w/v). This suspension 10 ml was sampled into a centrifuge tube made of Teflon, an equivalent for 0.5 U of PHA synthase YN2-C2 (cb) prepared in Example 6 and YN2-C2 prepared in Reference Example 1 were added to this suspension, which was shaken for 30 minutes at room temperature. By a centrifugation operation (for 10,000×g, 4° C., and 10 minutes), carbon black particles were collected as precipitation and separated from supernatant containing enzyme not binding to the carbon black. The carbon black was again suspended into TBS buffer containing 0.1% Tween-20, a centrifugal operation was repeated, whereby the carbon black was washed. Results of having measured an enzyme activity of the suspension of the washed carbon black are shown in Table 7.

TABLE 7

Evaluation of binding affinity of enzyme to carbon black

|  | Activity U |
|---|---|
| YN2-C2(cb) | 0.04 |
| YN2-C2 | 0.01 |

It was confirmed that the enzyme YN2-C2 (cb) fused with carbon black affinity sequence had a higher enzyme activity compared with the enzyme YN2-C2 of control, and thus could be effectively immobilized on a base material surface.

Example 8

PHA Capsular Structure of Carbon Black

Carbon black was suspended in TBS buffer containing 0.1% Tween-20 so that it might give 0.5% (w/v). The suspension 10 ml was sampled into a centrifuge tube made of Teflon, and an equivalent for 0.5 U of PHA synthase YN2-C2 (cb) or YN2-C2 was added hereto, and the solution was shaken for 30 minutes at room temperature. Once, carbon black was collected by a centrifugation operation, and again this was suspended into TBS buffer containing 0.1% Tween-20 so that it might give 0.5% (w/v). Subsequently, (R)-3-hydroxy-5-phenylvaleryl CoA prepared in Reference Example 2 was added so that it might give a final concentration 5 mM. Synthetic reaction was conducted by incubating for 30 minutes at 37° C.

PHA generated in the reaction mixture was dyed by Nile blue A, and was observed by a fluorescence microscope. In a sample in which YN2-C2 was added, free PHA granule was observed. In a sample in which YN2-C2 (cb) was added on the other hand, free PHA granule was not observed, and thereby it was confirmed that an efficient PHA synthesis by synthase had been performed.

The reaction mixture was separated by centrifugation (10,000×g, 4° C., and 10 minutes), and a hydrous cake with a capsular structure having carbon black therein as core was obtained. After re-suspension of the hydrous cake in water, the capsular structure was again collected by a centrifugation operation. Washing was carried out by repeating this operation 3 times.

Figure 2A:
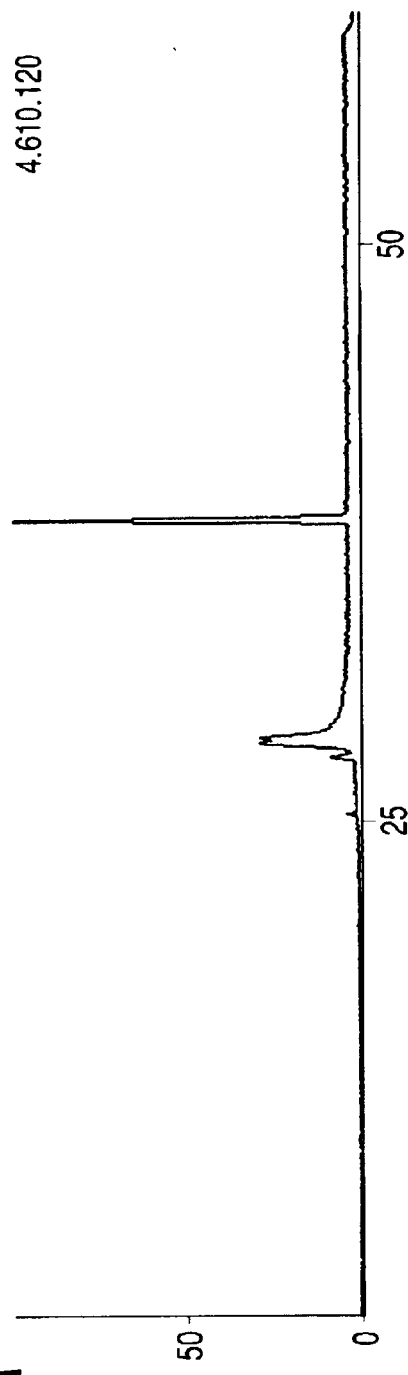
FIGS. 2A and 2B show GC-MS analysis results of the outer shell of a PHA capsular structure using carbon black in Example 8.
Figure 2B:
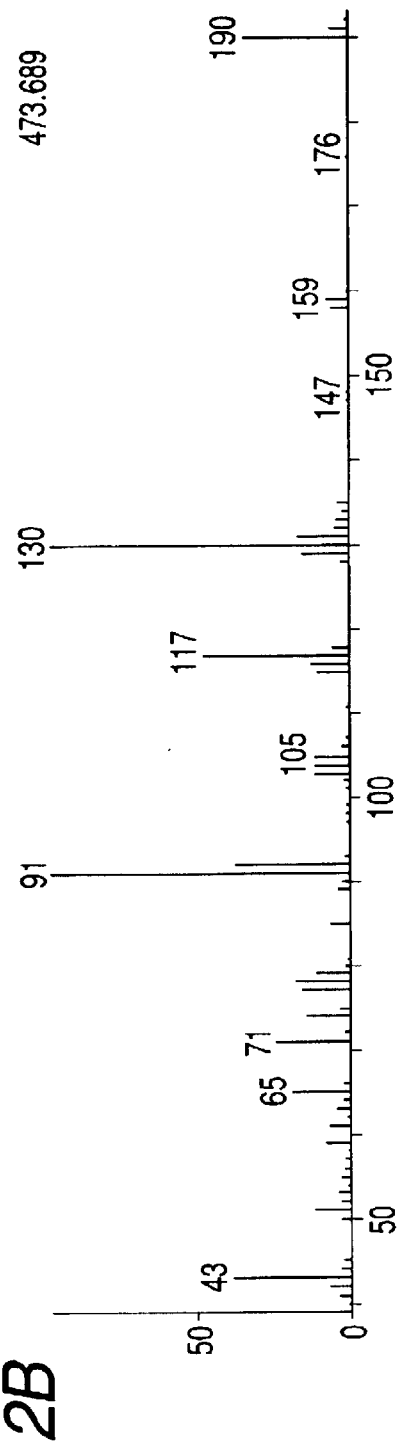

A part of the hydrous cake of the manufactured capsular structure was vacuum dried, suspended in chloroform 20 ml, and the suspension was stirred at 60° C. for 20 hours to extract PHA forming a pellicle. Extract was filtered by a membrane filter of 0.45 micrometers of pore size, vacuum concentration was carried out by a rotating evaporator, and, subsequently methanolysis was conducted according to a conventional method. Resultant product was analyzed by a gas chromatography-mass spectrometry equipment (GC-MS, Shimadzu QP-5050, EI method) to identify a methyl esterified PHA monomer unit. As a result, it was confirmed that the PHA concerned was a PHA having 3-hydroxy-5-phenylvaleric acid as a monomer unit as shown in FIGS. 2A and 2B. Moreover, the PHA was evaluated for a molecular weight by a gel permeation chromatography (GPC; TOSOH CORPORATION HLC-8020, column; Polymer Laboratory PLgel MIXED-C (5 micrometers), solvent; chloroform, column temperature; 40° C., polystyrene calibrated), and Mn=16,000 and Mw=36,000 were given.

Example 9

Obtaining of an Amino Acid Sequence Having a Binding Affinity to a Silicon Substrate (1) A surface of a single crystal silicon substrate (manufactured by FZ method, plane (100), specific resistance 100 Ω·cm to 1 kΩ·cm) was washed with methanol, and the surface of the substrate was filled with blocking buffer (0.1 M NaHCO$_3$ (pH 8.6), 5 mg/ml BSA, 0.1 mg/ml streptavidin, 0.02% NaN$_3$) including bovine serum albumin (BSA), and it was placed at 4° C. for 1 hour. The blocking buffer was then discarded and the silicon substrate was washed by TBST buffer (TBS buffer +0.1% Tween-20).

(2) An equivalent for 1.4×10¹¹ pfu of Ph.D.-7 phage display peptide library (manufactured by New England BioLabs Inc.) was added to the silicon substrate, which was kept still standing for 60 minutes at 25° C.

(3) The solution on the silicon substrate was discarded and the substrate was washed with TBST buffer.

(4) After elution buffer (0.2 M Glycine-HCl (pH 2.2) 1 mg/ml BSA) 1 ml was added to fill the surface and the solution was kept still standing for 3 minutes, the solution was moved into a microdose centrifugation tube, and then 1 M Tris-HCl of 150 μl (pH 9.1) was added for neutralization to obtain an eluted phage.

(5) *Escherichia coli* ER2537 (manufactured by New England BioLabs Inc.) in early stages of logarithmic growth was infected with the eluted phage, and the phage was amplified. It was cultured at 37° C. for 4.5 hours. Subsequently, the phage was separated from cell by a centrifugation, and purified by precipitation with polyethylene glycol. The phage purified and amplified was suspended in TBS buffer, and a titer was measured by infecting *Escherichia coli* with a suitable dilution series.

(6) The above described procedures (1) to (5) were repeated further 3 times using the amplified phage. However, a concentration of Tween-20 in TBST buffer to be used was raised to 0.5%, and conditions of washing were made severer. Titers of phages eluted in each cycle is shown in Table 8.

TABLE 8

Titer of phage eluted in each cycle

|  | Stock solution (A) | Silicon substrate bond (B) | B/A |
|---|---|---|---|
| First time | 1.4 × 10¹¹ | 2.8 × 10³ | 2.0 × 10⁻⁸ |
| Second time | 6.5 × 10¹¹ | 1.6 × 10⁵ | 2.5 × 10⁻⁷ |
| Third time | 6.4 × 10¹¹ | 1.2 × 10⁷ | 1.9 × 10⁻⁵ |
| Fourth time | 8.4 × 10¹¹ | 5.3 × 10⁸ | 6.3 × 10⁻⁴ |

(Unit of A, B, and C is represented by pfu/ml)

A large excessive *Escherichia coli* was infected with the finally eluted phage, and the phage was cloned. After infecting *Escherichia coli* with each clone and amplifying the clone, ssDNA was prepared, a base sequence of random domain was decoded and an amino acid sequence of peptide displayed was determined. Amino acid sequences and frequency of 30 clones that were picked up then are shown in Table 9.

TABLE 9

Determined amino acid sequence and frequency

| Determined amino acid sequence | Number (A) | Frequency (A/30) |
|---|---|---|
| SEQ ID No: 21 DSHFTIN Asp-Ser-His-Phe-Thr-Ile-Asn | 22 | 0.73 |
| SEQ ID NO: 185 DTFHTIN Asp-Thr-Phe-His-Thr-Ile-Asn | 5 | 0.17 |
| SEQ ID NO: 186 ESHFTIN Glu-Ser-His-Phe-Thr-Ile-Asn | 3 | 0.1 |

A silicon substrate binding motif having an amino acid sequence DSXXTIN (SEQ ID NO:180), particularly an amino acid sequence DSHFTIN (SEQ ID NO:21) having affinity to a silicon substrate has been determined.

Example 10

Preparation of a PHA Synthase Having a Binding Affinity to Silicon Substrate

An *Escherichia coli* expression vector expressed via a spacer sequence GGGS (SEQ ID NO:177) by fusing a silicon substrate affinity sequence of amino acid sequence DSHFTIN (SEQ ID NO:21) with N terminal of a PHA synthase was built as follows. DNA that encodes the amino acid sequence is manufactured as a double stranded synthetic oligonucleotide, and carries out ligation to a suitable restriction cleavage site (BamHI and SacI) of a pGEX-C1 plasmid. In this case, according to a description of manufacturer, two synthetic oligonucleotides O5 (5' GATC-CGATTCACATTTTACTATTAATGGTGGAGGTT CGGAGCT, SEQ ID NO:22) and O6 (5'CCGAACCTCCACCATTAATAGTAAAATGTGAAT CG, SEQ ID NO:23) were phosphorized using a T4 polynucleotide kinase (manufactured by Gibco). It was heated for 5 minutes at 80° C. continuously, and then was left to cool slowly to room temperature. This double stranded DNA fragment was directly used for subsequent cloning.

The plasmid pGEX-C1 was digested by BamI and SacI, and the above described double stranded DNA fragment was inserted. *Escherichia coli* (JM109) was transformed using this vector, and a strain for expression was obtained. Check of the strain was conducted by determining a base sequence of insertion by a sequencing using pGEX5' Sequencing Primer (manufactured by Amasham Pharmasia Biotech Corp.) and using a plasmid DNA prepared by Miniprep (Wizard Minipreps DNA Purification Systems, manufactured by PROMEGA) as a template. After carrying out pre-culture of the obtained strain by LB-Amp culture medium 10 mL overnight, 0.1 mL of a resultant containing the strain was added to LB-Amp culture medium of 10 mL, and shake culture was carried out at 37° C. and 170 rpm for 3 hours. IPTG was then added (final concentration 1 mM), and culture was continued at 37° C. for 4 to 12 hours.

The IPTG induced *Escherichia coli* was harvested (8000× g, 2 minutes, 4° C.), and it was re-suspended in 4-degree C. PBS of 1/10 amount. Cell was crushed by freeze thawing and sonication, cell debris was removed by centrifugation (8000×g, 10 minutes, 4° C.). After it was confirmed by SDS-PAGE that a target expression protein exists in supernatant, GST fusion protein induced and expressed was purified with glutathione Sepharose 4B (Glutathion Sepharose 4B beads: manufactured by Amasham Pharmasia Biotech Corp.)

A treatment controlling nonspecific adsorption was beforehand given to the glutathione sepharose used. That is, after the glutathione sepharose was washed (8000×g, 1 minute, 4° C.) 3 times by a same amount of PBS, it was treated with a same amount of PBS including 4% BSA added at 4° C. for 1 hour. It was washed twice by a same amount of PBS after treatment, and was re-suspended in ½ amount of PBS. The pretreated glutathione sepharose 40 μl was added to a cell free extract 1 mL, and the solution was calmly stirred at 4° C. Thereby, the fusion protein was GST-YN2-C1 adsorbed to the glutathione sepharose.

Glutathione sepharoses were collected by centrifugation (8000×g, 1 minute, 4° C.) after adsorption, and washing was performed 3 times with PBS 400 μL. Subsequently, 10 mM reduced glutathione 40 μL was added and the solution was stirred at 4° C. for 1 hour and the fusion protein adsorbed was eluted out. After centrifugation (8000×g, 2 minutes, 4° C.), supernatants were collected, and dialyzed to PBS to purify the GST fusion protein. It was confirmed that a single band was given by SDS-PAGE.

After each of the GST fusion protein 500 μg was digested by PreScission protease (Amasham Pharmasia Biotech Corp., 5U), the protease and GST were removed through glutathione sepharose. Flow through fraction was further processed by Sephadex G200 column equilibrated by PBS to obtain a final purified expression protein YN2-C1 (Si). It was confirmed that single band of 61.9 kDa was given by SDS-PAGE.

Purified enzyme activity was measured by the above described procedure. Moreover, a protein concentration in samples was measured with micro BCA protein determination reagent kit (manufactured by Pierce Chemical com.) Enzyme concentration was 2.1 U/ml and specific activity was 4.1 U/mg protein. Purified enzyme was concentrated using organism solution sample concentration agent (Mizubutorikun AB-1100, manufactured by ATTO Corporation) to obtain 10 U/ml purified enzyme solution.

Example 11

Evaluation of a Binding Affinity to Silicon Substrate

A silicon substrate surface was washed with TBST buffer containing 0.1% Tween-20. An equivalent for 0.5 U of PHA synthase YN2-C1(Si) prepared in Example 10, or YN2-C1 prepared in Reference Example was added hereto, and it was shaken for 30 minutes at room temperature. The silicon substrate surface was washed with TBST buffer, and enzyme not binding to the silicon substrate was removed. The washed silicon substrate surface was filled with TBST buffer, 3-hydroxy octanoyl CoA that was a substrate of the enzyme was added hereto, and an activity of enzyme fixed on the silicon substrate surface was measured by generation rate of CoA. Results are shown in Table 10.

TABLE 10

Evaluation of binding affinity of enzyme to silicon substrate

|  | Activity U |
|---|---|
| YN2-C1(Si) | 0.05 |
| YN2-C1 | 0.01 |

It was confirmed that the enzyme YN2-C1 (Si) fused with silicon substrate affinity sequence had a higher enzyme activity compared with the enzyme YN2-C1 of control, and could be effectively immobilized on a base material surface.

Example 12

PHA Laminated Structure of Silicon Substrate

A silicon substrate surface was washed with TBST buffer containing 0.1% Tween-20. An equivalent for 0.5 U of PHA synthase YN2-C1(Si) or YN2-C1 was added hereto, and it was shaken for 30 minutes at room temperature. The silicon substrate surface was washed with TBST buffer, and the enzyme not binding to the silicon substrate was removed. The washed silicon substrate surface was filled with TBST buffer, and (R)-3-hydroxy-5-(4-fluorophenyl)valeryl CoA prepared in Reference Example 2 was added so that it might give a final concentration 5 mM. Synthetic reaction was conducted by incubating for 30 minutes at 37° C.

The PHA generated in the reaction mixture supernatant and on the silicon substrate was dyed by Nile blue A, and was observed with fluorescence microscope. In a sample in which YN2-C1 was added, free PHA granule was observed. In a sample in which YN2-C1 (Si) was added on the other hand, free PHA granule was not observed in the reaction mixture supernatant, and thereby it was confirmed that an efficient PHA synthesis by synthase had been performed. Moreover, the PHA laminated on the silicon substrate was observable by a fluorescent staining.

Figure 3A:
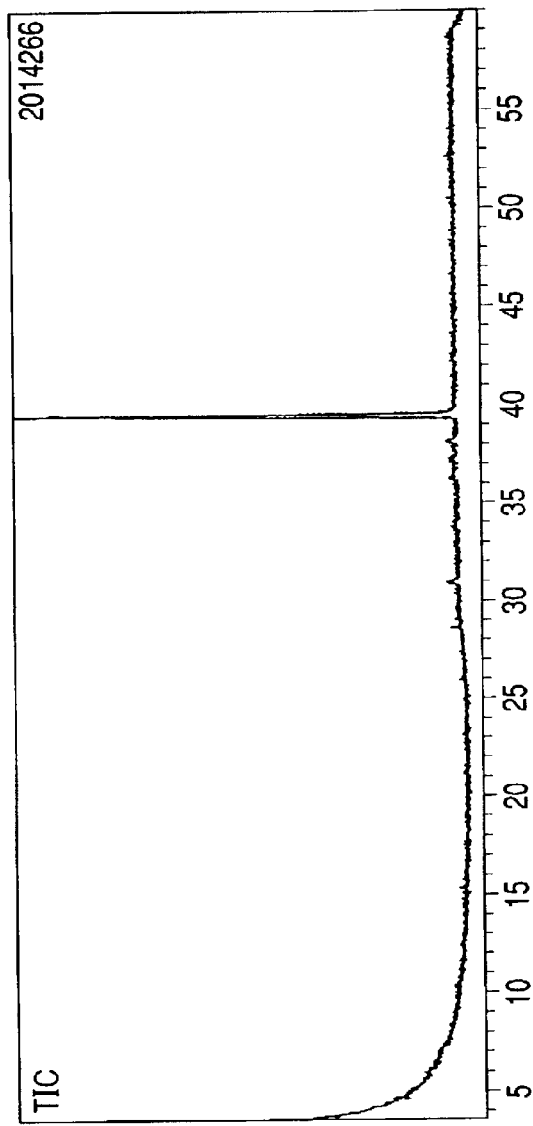
FIGS. 3A and 3B show GC-MS analysis results of the laminated body of a PHA laminated structure using a silicon board in Example 12.
Figure 3B:
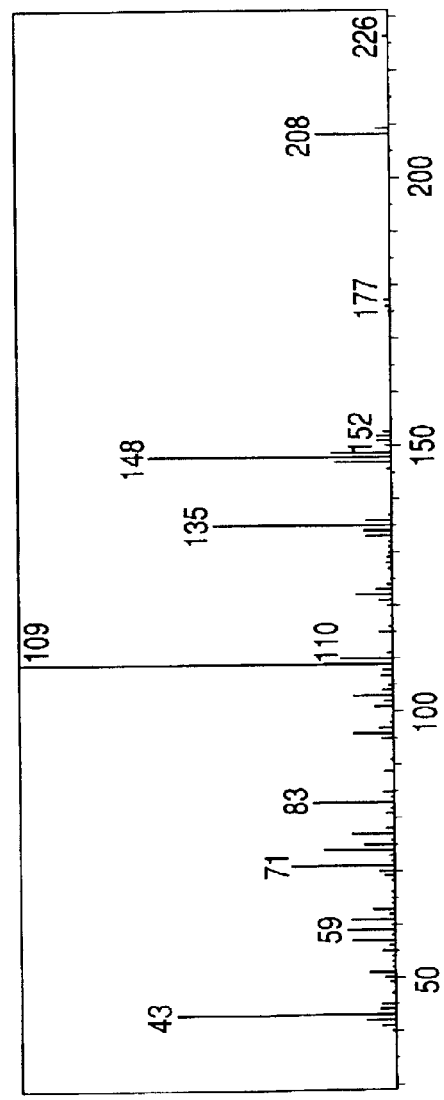

The manufactured PHA laminated silicon substrate structure was vacuum dried, subsequently was immersed into chloroform 20 ml, and the solution was stirred for 20 hours at 60° C. to extract the laminated PHA. Extract was filtered by a membrane filter of 0.45 micrometers of pore size, vacuum concentration was carried out by a rotating evaporator, and, subsequently methanolysis was conducted according to a conventional method. Resultant product was analyzed by a gas chromatography-mass spectrometry equipment (GC-MS, Shimadzu QP-5050, EI method) to identify a methyl esterified PHA monomer unit. As a result, it was confirmed that the PHA concerned was a PHA having (R)-3-hydroxy-5-(4-fluorophenyl)valeric acid as a monomer unit as shown in FIGS. 3A and 3B. Moreover, the PHA was evaluated for a molecular weight by a gel permeation chromatography (GPC; TOSOH CORPORATION HLC-8020, column; Polymer Laboratory PLgel MIXED-C (5 micrometers), solvent; chloroform, column temperature; 40° C., polystyrene calibrated), and Mn=17,000 and Mw=37,000 were given.

Example 13

Preparation of a Capsular Structure (Gradient Structure)

1 mass part of copper phthalocyanine particle (volume mean particle diameter 1.45 micrometers) whose particle diameter was equalized by a sedimentation method, and 39 parts by mass of PBS were added to 10 parts by mass of the expression protein YN2-C1 (pht) (10 U/ml) prepared in Example 2, and the mixture was gently shaken for 30 minutes at 30° C. to immobilize the PHA synthase to copper phthalocyanine. This was separated by centrifuge (10,000× g, 4° C., and 10 minutes), the precipitation was suspended into PBS solution, and then was again separated by centrifuge (10,000×g, 4° C., and 10 minutes) to obtain an immobilized enzyme.

The immobilized enzyme was immersed in 0.1 M phosphoric acid buffer (pH 7.0) 100 parts by mass including 30 mM (R)-3-hydroxyoctanoyl CoA (prepared by a procedure in Eur. J. Biochem., 250, and 432–439 (1997)), and 0.1% bovine serum albumin (manufactured by Sigma-Aldrich Com.) Subsequently, while the reaction mixture was gently shaken at 30° C., to this reaction system, 0.1 M phosphoric acid buffer (pH 7.0) including 30 mM (R)-3-hydroxypimelyl CoA (prepared by a procedure in J. Bacteriol., 182, 2753–2760 (2000)) and 0.1% bovine serum albumin (manufactured by Sigma-Aldrich Com.) were added at a rate of 25 parts by mass per 1 minute using micro tube pump (MP-3N, manufactured by TOKYO RIKAKIKAI CO, LTD.)

After shaking for 30 minutes the resultant was washed with 0.1 M phosphoric acid buffer (pH 7.0), to remove unreacted matter etc., followed by air-drying the resulting, and thereby a capsular structure was obtained.

Mass of a polymer formed on a surface of this capsular structure was measured by a time-of-flight type secondary ion mass spectroscopy equipment (TOF-SIMS IV, manufactured by CAMECA). Obtained mass spectrum showed that the capsular structure surface was comprised of a copolymer of 3-hydroxypimelic acid and 3-hydroxyoctanoic acid (mole ratio 17:1). Moreover, when a mass spectrum measurement was advanced by TOF-SIMS in a same manner, as cutting off the capsular structure surface little by little by ion sputtering, a composition ratio of 3-hydroxypimelic acid in the above described copolymer decreased gradually, and a composition ratio of 3-hydroxyoctanoic acid increased. From this result, it was clear that a capsular structure of the Example has a structure in which a surface is covered with polyhydroxy pimelate having hydrophilic functional groups, and a lower area is covered with a copolymer of 3-hydroxypimelic acid having hydrophilic functional groups and 3-hydroxyoctanoic acid having hydrophobic functional groups, increasing a composition ratio of 3-hydroxyoctanoic acid as it extends in lower layer.

Moreover, the PHA was evaluated for a molecular weight by gel permeation chromatography (GPC; TOSOH CORPORATION HLC-8020, column; Polymer Laboratory PLgel MIXED-C (5 micrometers), solvent; chloroform, column temperature; 40° C., polystyrene calibrated), and Mn=21,000 and Mw=40,000 were given.

Example 14

Preparation of a Capsular Structure (Chemical Modification)

1 mass part of copper phthalocyanine particle (particle diameter 0.12 micrometers to 135 micrometers) and 39 parts by mass of PBS were added to 10 parts by mass of the expression protein YN2-C1 (pht) (10 U/ml) prepared in Example 2, and the mixture was gently shaken for 30 minutes at 30° C. to immobilize PHA synthase to copper phthalocyanine. This was separated by centrifuge (10,000× g, 4° C., and 10 minutes), the precipitation was suspended into PBS solution, and then was again separated by centrifuge (10,000×g, 4° C., and 10 minutes) to obtain an immobilized enzyme.

The immobilized enzyme was suspended in 48 parts by mass of 0.1 M phosphoric acid buffer (pH 7.0), and to this suspension were added 0.8 parts by mass of (R,S)-3-hydroxy-5-phenoxyvaleryl CoA which had been prepared by hydrolyzing 3-hydroxy-5-phenoxy valerianate obtained by Reformatsky reaction of 3-phenoxy-propanal and ethyl bromoacetate was hydrolyzed to give 3-hydroxy-5-phenoxyvaleric acid and then carrying out a preparation according to a procedure given in Eur. J. Biochem., 250, and 432–439 (1997), 0.2 parts by mass of (R,S)-3-hydroxy-7,8-epoxyoctanoyl CoA which had been prepared by epoxidating unsaturated part of 3-hydroxy-7-octenic acid synthesized according to a procedure given in Int. J. Biol. Macromol., 12, and 85–91 (1990) with 3-chlorobenzoic acid and then carrying out a preparation according to a procedure given in Eur. J. Biochem., 250, and 432–439 (1997), and 0.1 mass part of bovine serum albumin (manufactured by Sigma-Aldrich Com.), then the resultant was gently shaken at 30° C. for 2 hours to obtain sample 1.

A same procedure as the above described procedure were repeated except that (R,S)-3-hydroxy-7,8-epoxyoctanoyl CoA was changed into 3-hydroxyoctanoyl CoA., to obtain sample 2 as a control.

After the above described sample 10 µl was sampled on a slide glass, 1% Nile blue A aqueous solution 10 µl was added and mixed on the slide glass, a cover glass was placed thereon, and subsequently the resulting was observed using a fluorescence microscope (330–380 nm excitation filter, 420 nm long pass absorption filter, manufactured by Nikon Corporation). Then, also in all samples, it was confirmed that copper phthalocyanine particle surface emitted fluorescence. Therefore, it turned out that surface of copper phthalocyanine particle was covered with PHA.

As comparison, copper phthalocyanine 1 mass part was added to 0.1 M phosphoric acid buffer (pH 7.0) 49 parts by mass and the solution was shaken gently at 30° C. for 2.5 hours, the resultant was thus dyed by Nile blue A in a same manner and observed using a fluorescence microscope. As a result, copper phthalocyanine particle surface did not emit fluorescence at all.

Moreover, a part of the sample was collected by centrifugation (for 10,000×g, 4° C., and 10 minutes), after vacuum dried, it was suspended in chloroform and the solution was stirred at 60° C. for 20 hours, and PHA constituting pellicle was extracted. $^1$H-NMR analysis was conducted for this extract (used instrument: FT-NMR: Bruker DPX400, measured nuclide:$^1$H, used solvent: heavy chloroform (with TMS)). A unit percentage of each side chain unit calculated from the resulting data are shown in Table 11.

TABLE 11

| Composition of pellicle PHA of capsule structure ($^1$H-NMR, unit %) | | |
|---|---|---|
| Monomer unit | Sample 1 | Sample 2 |
| 3-hydroxy-5-phenoxy valeric acid | 84% | 76% |
| 3-hydroxy-7,8-epoxy octanoic acid | 16% | — |
| 3-hydroxyoctanoic acid | — | 24% |

Centrifugation (10,000×g, 4° C., and 10 minutes) of 50 parts by mass of the above described sample 1 was carried out, the capsular structure was collected, and operation of suspending the resultant in purified water 50 mass part was repeated 3 times. Subsequently, hexamethylenediamine 0.5 mass part was dissolved in the suspension as a cross linking agent. After confirming dissolution, water was removed by freeze-drying (referred to as sample 3). Moreover, sample 3 was reacted by 70° C. for 12 hours (referred to as sample 4). The above described sample 3 and sample 4 were suspended in chloroform, and the suspension was stirred at 60° C. for 20 hours to extract PHA constituting pellicle, chloroform was removed by vacuum evaporation, and was measured using a differential scanning calorimeter equipment (DSC; manufactured by Perkin Elmer, Inc., Pyris 1, temperature rising: 10-degree C./minute). Then, the sample 3 gave a clear exothermic peak in the vicinity of 90° C., and this showed that a reaction between epoxy groups in polymer and hexamethylenediamine occurred, and that a cross linkage among polymers proceeded. On the other hand, in the sample 4, clear heat flaw was not observed, but it was shown that a cross linkage reaction had almost completed.

Moreover, infrared absorption was measured for a same sample (FT-IR; manufactured by Perkin Elmer, Inc., 1720X). Then, peaks of amine (near 3340 cm$^{-1}$) and epoxy (near 822 cm$^{-1}$) observed in the sample 3 had disappeared in the sample 4.

It became clear from the above result that a cross-linked polymer was obtained by a reaction between a PHA having epoxy units in side chains and hexamethylenediamine.

On the other hand, as comparison, although a same evaluation was conducted for the sample 2, evaluation results as in the above described case clearly showing cross linkage among polymers were not obtained.

Example 15

Obtaining of an Amino Acid Sequence Having a Binding Affinity to Copper Phthalocyanine (1) A copper phthalocyanine (alpha type: Tokyo Kasei Kogyo Co., Ltd.) was dispersed in TBS buffer (50 mM Tris-HCl pH 7.5, 150 mM NaCl) including 0.1% Tween-20 to obtain a concentration of 5 mg/ml. This 10 μl was added to Eppendorf tube, and TBST buffer (TBS buffer +0.1% Tween-20) 990 μl was added for dilution.

(2) An equivalent for 4×10$^{10}$pfu of ph.D.-12 phage display peptide library (manufactured by New England BioLabs Inc.) was added to the tube, which was placed for 10 minutes at 25° C.

(3) After the tube was separated by centrifugation (20, 630×g, 5 minutes), supernatant was discarded and the pigment was collected as precipitation. The collected pigment was again suspended in TBST buffer, centrifugation was repeated, and thus the pigment was washed 10 times by TBST buffer.

(4) After elution buffer 100 μl (0.2 M Glycine-HCl (pH 2.2), 1 mg/ml BSA) was added and the solution was placed for 1 minute, centrifugation (20,630×g, 5 minutes) was carried out, then supernatant was moved to another Eppendorf tube, 1 M Tris-HCl (pH 9.1) 15 μl was added for neutralization to obtain an eluted phage.

(5) *Escherichia coli* ER2537 (manufactured by New England BioLabs Inc.) in early stages of logarithmic growth was infected with the eluted phage, and the phage was amplified. It was cultured at 37° C. for 4.5 hours. Subsequently, the phage was separated from cell by a centrifugation, and purified by precipitation in polyethylene glycol. The phage purified and amplified was suspended in TBS buffer, and a titer was measured by infecting *Escherichia coli* with a suitable dilution series.

(6) The above described procedures (1) to (5) were repeated further 3 times using the amplified phage. However, a concentration of Tween-20 in TBST buffer to be used was raised to 0.5%, and conditions of washing were made severer. Henceforth, the same operation was conducted from second time also to an Eppendorf tube as a control. Titers of phages eluted in each cycle are shown in Table 12.

TABLE 12

Titer of phage eluted in each cycle

| | Stock solution (A) | Control bond (B) | Phthalocyanine bond (C) | C/A | C/B |
|---|---|---|---|---|---|
| First time | 4.0 × 10$^{11}$ | | 1.2 × 10$^6$ | 3.0 × 10$^{-6}$ | |
| Second time | 1.6 × 10$^{11}$ | 1.1 × 10$^5$ | 1.7 × 10$^5$ | 1.1 × 10$^{-5}$ | 1 |

TABLE 12-continued

Titer of phage eluted in each cycle

| | Stock solution (A) | Control bond (B) | Phthalocyanine bond (C) | C/A | C/B |
|---|---|---|---|---|---|
| Third time | 2.0 × 10$^{11}$ | 1.6 × 10$^5$ | 3.0 × 10$^8$ | 1.5 × 10$^{-3}$ | 1800 |
| Fourth time | 1.7 × 10$^{11}$ | 2.7 × 10$^6$ | 5.3 × 10$^9$ | 3.1 × 10$^{-2}$ | 2000 |

(Unit of A, B, and C is Represented by pfu/ml)

Large excessive *Escherichia coli* was infected with the finally eluted phage, and the phage was cloned. After infecting the *Escherichia coli* with each clone and amplifying the clone, ssDNA was prepared, a base sequence of random domain was decoded and an amino acid sequence of peptide displayed was determined, and thereby amino acid sequences having a binding affinity to copper phthalocyanine were obtained.

Resulting amino acid sequence and frequency are shown in Table 13.

TABLE 13

Determined amino acid sequence and frequency

| Determined amino acid sequence | Number (A) | Frequency (A/36) |
|---|---|---|
| Lys-Tyr-Asp-Ser-Arg-His-Leu-His-Thr-His-Ser-His (SEQ ID NO: 24) | 6 | 0.17 |
| Pro-Asn-Arg-Leu-Gly-Arg-Arg-Pro-Val-Arg-Trp-Glu (SEQ ID NO: 25) | 6 | 0.17 |
| Lys-Cys-Cys-Tyr-Tyr-Asp-His-Ser-His-Ala-Leu-Ser (SEQ ID NO: 26) | 4 | 0.11 |
| Glu-Tyr-Leu-Ser-Ala-Ile-Val-Ala-Gly-Pro-Trp-Pro (SEQ ID NO: 27) | 3 | 0.08 |
| Lys-Leu-Trp-Ile-Leu-Glu-Pro-Thr-Val-Thr-Pro-Thr (SEQ ID NO: 28) | 3 | 0.08 |
| Gln-Ser-Asn-Leu-Lys-Val-Ile-Pro-Ser-Trp-Trp-Phe (SEQ ID NO: 29) | 3 | 0.08 |
| Trp-Ile-Pro-Pro-Gln-Trp-Ser-Arg-Leu-Ile-Glu-Pro (SEQ ID NO: 30) | 3 | 0.08 |
| Asp-His-Pro-Gln-Ala-Lys-Pro-Asn-Trp-Tyr-Gly-Val (SEQ ID NO: 31) | 1 | 0.02 |
| Gly-Leu-Pro-Pro-Tyr-Ser-Pro-His-Arg-Leu-Ala-Gln (SEQ ID NO: 32) | 1 | 0.02 |
| Lys-Leu-Thr-Thr-Gln-Tyr-Met-Ala-Arg-Ser-Ser-Ser (SEQ ID NO: 33) | 1 | 0.02 |
| Lys-Val-Trp-Met-Leu-Pro-Pro-Leu-Pro-Gln-Ala-Thr (SEQ ID NO: 34) | 1 | 0.02 |
| Asn-Val-Thr-Ser-Thr-Ala-Phe-Ile-Asp-Thr-Pro-Trp (SEQ ID NO: 35) | 1 | 0.02 |
| Arg-Leu-Asn-Leu-Asp-Ile-Ile-Ala-Val-Thr-Ser-Val (SEQ ID NO: 36) | 1 | 0.02 |
| Thr-Leu-Pro-Ser-Pro-Leu-Ala-Leu-Leu-Thr-Val-His (SEQ ID NO: 37) | 1 | 0.02 |
| Thr-Asn-Arg-His-Asn-Pro-His-His-Leu-His-His-Val (SEQ ID NO: 38) | 1 | 0.02 |

Example 16

A same procedure as in Example 2 was repeated and a PHA synthase having a binding affinity to a copper phthalocyanine was prepared as follows. An *Escherichia coli* expression vector expressed by fusing to N terminal of a PHA synthase through a spacer sequence GS to each amino acid sequence (from SEQ ID NO:24 to SEQ ID NO:38) was built as follows. In DNA encoding these amino acid sequences, since it was manufactured as a double stranded synthetic DNA, a set of synthetic oligonucleotides in next table 14 was prepared.

TABLE 14

Synthetic DNA set for expressing each amino acid sequence

| SEQ ID NO: amino acid sequence | SEQ ID NO: base sequence of synthetic DNA | |
|---|---|---|
| SEQ ID NO: 24 | 5'-GATCCAAATATGATAGCCGTCATCTGCATACCCATAGCCATGAGCT-3' | SEQ ID NO:64 |
| KYDSRHLHTHSH | 5'-CATGGCTATGGGTATGCAGATGACGGCTATCATATTTG-3' | SEQ ID NO:65 |
| SEQ ID NO:25 | 5'-GATCCCCGAACCGTCTGGGCCGTCGTCCGGTGCGTTGGGAAGAGCT-3' | SEQ ID NO:66 |
| PNRLGRRPVRWE | 5'-CTTCCCAACGCACCGGACGACGGCCCAGACGGTTCGGG-3' | SEQ ID NO:67 |
| SEQ ID NO:26 | 5'-GATCCAAATGCTGCTATTATGATCATAGCCATGCGCTGAGCGAGCT-3' | SEQ ID NO:68 |
| KCCYYDHSHALS | 5'-CGCTCAGCGCATGGCTATGATCATAATAGCAGCATTTG-3' | SEQ ID NO:69 |
| SEQ ID NO:27 | 5'-GATCCGAATATCTGAGCGCGATTGTGGCGGGCCCGTGGCCGGAGCT-3' | SEQ ID NO:70 |
| EYLSAIVAGPWP | 5'-CCGGCCACGGGCCCGCCACAATCGCGCTCAGATATTCG-3' | SEQ ID NO:71 |
| SEQ ID NO:28 | 5'-GATCCAAACTGTGGATTCTGGAACCGACCGTGACCCCGACCGAGCT-3' | SEQ ID NO:72 |
| KLWILEPTVTPT | 5'-CGGTCGGGGTCACGGTCGGTTCCAGAATCCACAGTTTG-3' | SEQ ID NO:73 |
| SEQ ID NO:29 | 5'-GATCCCAGAGCAACCTGAAAGTGATTCCGAGCTGGTGGTTTGAGCT-3' | SEQ ID NO:74 |
| QSNLKVIPSWWF | 5'-CAAACCACCAGCTCGGAATCACTTTCAGGTTGCTCTGG-3' | SEQ ID NO:75 |
| SEQ ID NO:30 | 5'-GATCCTGGATTCCGCCGCAGTGGAGCCGTCTGATTGAACCGGAGCT-3' | SEQ ID NO:76 |
| WIPPQWSRLIEP | 5'-CCGGTTCAATCAGACGGCTCCACTGCGGCGGAATCCAG-3' | SEQ ID NO:77 |
| SEQ ID NO:31 | 5'-GATCCGATCATCCGCAGGCGAAACCGAACTGGTATGGCGTGGAGCT-3' | SEQ ID NO:78 |
| DHPQAKPNWYGV | 5'-CCACGCCATACCAGTTCGGTTTCGCCTGCGGATGATCG-3' | SEQ ID NO:79 |
| SEQ ID NO:32 | 5'-GATCCGGCCTGCCGCCGTATAGCCCGCATCGTCTGGCGCAGGAGCT-3' | SEQ ID NO:80 |
| GLPPYSPHRLAQ | 5'-CCTGCGCCAGACGATGCGGGCTATACGGCGGCAGGCCG-3' | SEQ ID NO:81 |
| SEQ ID NO:33 | 5'-GATCCAAACTGACCACCCAGTATATGGCGCGTAGCAGCAGCGAGCT-3' | SEQ ID NO:82 |
| KLTTQYMARSSS | 5'-CGCTGCTGCTACGCGCCATATACTGGGTGGTCAGTTTG-3' | SEQ ID NO:83 |
| SEQ ID NO:34 | 5'-GATCCAAAGTGTGGATGCTGCCGCCGCTGCCGCAGGCGACCGAGCT-3' | SEQ ID NO:84 |
| KVWMLPPLPQAT | 5'-CGGTCGCCTGCGGCAGCGGCGGCAGCATCCACACTTTG-3' | SEQ ID NO:85 |
| SEQ ID NO:35 | 5'-GATCCAACGTGACCAGCACCGCGTTTATTGATACCCCGTGGGAGCT-3' | SEQ ID NO:86 |
| NVTSTAFIDTPW | 5'-CCCACGGGGTATCAATAAACGCGGTGCTGGTCACGTTG-3' | SEQ ID NO:87 |
| SEQ ID NO:36 | 5'-GATCCCGTCTGAACCTGGATATTATTGCGGTGACCAGCGTGGAGCT-3' | SEQ ID NO:88 |
| RLNLDIIAVTSV | 5'-CCACGCTGGTCACCGCAATAATATCCAGGTTCAGACGG-3' | SEQ ID NO:89 |
| SEQ ID NO:37 | 5'-GATCCACCCTGCCGAGCCCGCTGGCGCTGCTGACCGTGCATGAGCT-3' | SEQ ID NO:90 |
| TLPSPLALLTVH | 5'-CATGCACGGTCAGCAGCGCCAGCGGGCTCGGCAGGGTG-3' | SEQ ID NO:91 |
| SEQ ID NO:38 | 5'-GATCCACCAACCGTCATAACCCGCATCATCTGCATCATGTGGAGCT-3' | SEQ ID NO:92 |
| TNRHNPHHLHHV | 5'-CCACATGATGCAGATGATGCGGGTTATGACGGTTGGTG-3' | SEQ ID NO:93 |

Two kinds of synthetic DNA to each amino acid sequence in Table 14 were phosphorylated according to a description of a manufacturer respectively using a T4 polynucleotide kinase (manufactured by Gibco). Subsequently, equi-molar amounts of two kinds of the synthetic DNA were mixed and heated for 5 minutes at 80° C., and then cooled slowly to room temperature to form a double stranded DNA fragment. The formed double stranded DNA fragment was directly used for subsequent cloning.

Plasmid pGEX-C1 was digested by BamHI and SacI, and the above described double stranded DNA fragment was inserted. Using the vector, *Escherichia coli* (JM109) was transformed to obtain a strain for expression. A check of the strain was conducted by determining a base sequence of insertion by a sequencing using pGEX5' Sequencing Primer (manufactured by Amasham Pharmasia Biotech Corp.) and using a plasmid DNA prepared by Miniprep (Wizard Minipreps DNA Purification Systems, manufactured by PROMEGA) as a template. After carrying out pre-culture of the obtained strain by LB-Amp culture medium 10 mL overnight, 0.1 mL of a resultant containing the strain was added to LB-Amp culture medium of 10 mL, and shake culture was carried out at 37° C. and 170 rpm for 3 hours. IPTG was then added (final concentration 1 mM), and culture was continued at 37° C. for 4 to 12 hours.

IPTG induced *Escherichia coli* was harvested (8000×g, 2 minutes, 4° C.), and it was re-suspended in 4-degree C. PBS of 1/10 amount. Cell was crushed by freeze thawing and sonication, cell debris was removed by centrifugation (8000×g, 10 minutes, 4° C.). After it was confirmed by SDS-PAGE that a target expression protein existed in supernatant, a GST fusion protein induced and expressed was purified with glutathione Sepharose 4B (Glutathion Sepharose 4B beads: manufactured by Amasham Pharmasia Biotech Corp.)

A treatment controlling nonspecific adsorption was beforehand given to the glutathione sepharose used. That is, after the glutathione sepharose was washed (8000×g, 1 minute, 4° C.) 3 times by a same amount of PBS, it was treated with a same amount of PBS including 4% BSA added at 4° C. for 1 hour. It was washed twice by a same amount of PBS after treatment, and was re-suspended in ½ amount of PBS. The petreated glutathione sepharose 40 µl was added to a cell free extract 1 mL, and calmly stirred at 4° C. Thereby, fusion proteins GST-aa24-YN2-C1 to GST-aa38-YN2-C1 were adsorbed to the glutathione sepharose. [In fusion proteins GST-aa##-YN2-C1, aa## means that a polypeptide comprising an amino acid sequence of SEQ ID NO:## being fused between PHA synthase and GST is expressed.]

The glutathione sepharoses were collected by centrifugation (8000×g, 1 minute, 4° C.) after adsorption, and washing was performed 3 times with PBS 400 µL. Subsequently, 10 mM reduced glutathione 40 µL was added and stirred at 4° C. for 1 hour and the fusion protein adsorbed was eluted out. After centrifugation (8000×g, 2 minutes, 4° C.), supernatants were collected, and dialyzed to PBS to purify the GST fusion protein. It was confirmed that a single band was given by SDS-PAGE.

After each of the GST fusion protein 500 µ g was digested by PreScission protease (Amasham Pharmasia Biotech Corp., 5U), the protease and GST were removed through glutathione sepharose. Flow through fraction was further processed by Sephadex G200 column equilibrated by PBS to obtain final purified expression proteins aa24-YN2-C1(pht) to aa38-YN2-C1(pht). [In expression protein aa##-YN2-C1 (pht), aa## means that a polypeptide comprising an amino acid sequence of SEQ ID NO:## is expressed by being fused with N terminal of PHA synthase.]

Activity of each purified enzyme was measured by the above described procedure. Moreover, a protein concentration in samples was measured with micro BCA protein determination reagent kit (manufactured by Pierce Chemical com.). Enzyme concentration was 1.9 U/ml and specific activity was 4.0 U/mg protein. The purified enzyme was concentrated using organism solution sample concentration agent (Mizubutorikun AB-1100, manufactured by ATTO Corporation) to obtain 10 U/ml purified enzyme solution.

Example 17

Evaluation of a Binding Affinity to Copper Phthalocyanine

Copper phthalocyanine was suspended in TBS buffer containing 0.1% Tween-20 so that it might give 0.5% (w/v). This suspension 10 ml was sampled in a centrifuge tube made of Teflon, and an equivalent for 0.5 U of PHA synthase aa24-YN2-C1(pht) to aa38-YN2-C1 (pht) prepared in Example 16 and YN2-C1 prepared in Reference Example 1 were added hereto, and shaken for 30 minutes at room temperature. By centrifugation operation (for 10,000×g, 4° C., and 10 minutes), copper phthalocyanine particles were collected as precipitation and separated from supernatant containing enzyme not binding to copper phthalocyanine. The copper phthalocyanine was again suspended into TBS buffer containing 0.1% Tween-20, a centrifugal operation was repeated, whereby the copper phthalocyanine was washed. Results of having measured an enzyme activity of the suspension of the washed copper phthalocyanine are shown in Table 15.

TABLE 15

Evaluation of binding affinity of enzyme to copper phthalocyanine

| Enzyme | Fusion amino acid sequence | Enzyme activity U |
|---|---|---|
| Aa24-YN2-C1 (pht) | SEQ ID NO:24 KYDSRHLHTHSH | 0.06 |
| Aa25-YN2-C1 (pht) | SEQ ID NO:25 PNRLGRRPVRWE | 0.06 |
| Aa26-YN2-C1 (pht) | SEQ ID NO:26 KCCYYDHSHALS | 0.05 |
| Aa27-YN2-C1 (pht) | SEQ ID NO:27 EYLSAIVAGPWP | 0.05 |
| Aa28-YN2-C1 (pht) | SEQ ID NO:28 KLWILEPTVTPT | 0.05 |
| Aa29-YN2-C1 (pht) | SEQ ID NO:29 QSNLKVIPSWWF | 0.05 |
| Aa30-YN2-C1 (pht) | SEQ ID NO:30 WIPPQWSRLIEP | 0.05 |
| Aa31-YN2-C1 (pht) | SEQ ID NO:31 DHPQAKPNWYGV | 0.05 |
| Aa32-YN2-C1 (pht) | SEQ ID NO:32 GLPPYSPHRLAQ | 0.05 |
| Aa33-YN2-C1 (pht) | SEQ ID NO:33 KLTTQYMARSSS | 0.05 |
| Aa34-YN2-C1 (pht) | SEQ ID NO:34 KVWMLPPLPQAT | 0.05 |
| Aa35-YN2-C1 (pht) | SEQ ID NO:35 NVTSTAFIDTPW | 0.05 |
| Aa36-YN2-C1 (pht) | SEQ ID NO:36 RLNLDIIAVTSV | 0.05 |
| Aa37-YN2-C1 (pht) | SEQ ID NO:37 TLPSPLALLTVH | 0.04 |
| Aa38-YN2-C1 (pht) | SEQ ID NO:38 TNRHNPHHLHHV | 0.04 |
| YN2-C1 | — | 0.01 |

It was confirmed that the enzyme aa24-YN2-C1(pht) to aa38-YN2-C1(pht) fused with a copper phthalocyanine affinity sequence were fused had a higher enzyme activity compared with the enzyme YN2-C1 of control, and thus could be effectively immobilized on a base material surface.

Example 18

Two kinds of amino acid sequences capable of binding to copper phthalocyanine, Lys-Tyr-Asp-Ser-Arg-His-Leu-His-Thr-His-Ser-His (SEQ ID NO:24) and Pro-Asn-Arg-Leu-Gly-Arg-Arg-Pro-Val-Arg-Trp-Glu (SEQ ID NO:25), were all connected in the indicated order in series through the spacer sequence Gly-Gly-Gly-Ser-Gly-Gly-Gly-Ser (SEQ ID NO:181) to give Lys-Tyr-Asp-Ser-Arg-His-Leu-His-Thr-His-Ser-His-Gly-Gly-Gly-Ser-Gly-Gly-Gly-Ser-Pro-Asn-Arg-Leu-Gly-Arg-Arg-Pro-Val-Arg-Trp-Glu (SEQ ID NO:144), which was further fused to the N terminal of a PHA synthase through the use of the spacer sequence GS to prepare an *Escherichia coli* expression vector in the following. The DNA encoding this amino acid sequence was formed as a double-stranded DNA fragment by, after phosphorylating (3) After the tube was separated by centrifugation (20,630×g, 5 minutes), supernatant was discarded and the pigment was collected as a precipitation. The collected pigment was again suspended in TBST buffer, centrifugation was repeated, and thus the pigment was washed 10 times by TBST buffer.

(4) After elution buffer 100 µl (0.2 M Glycine-HCl (pH 2.2), 1 mg/ml BSA) was added and being placed for 1 minute, centrifugation (20,630×g, 5 minutes) was carried out, then supernatant was moved to another Eppendorf tube,

```
Seq.1:
5'-GATCCAAATATGATAGCCGTCATCTGCATACCCATAGCCATGGCGGCGGCAGCGG    (SEQ ID NO:145)

CGGCGGCAGCCCGAACCGTCTGGGCCGTCGTCCGGTGCGTTGGGAAGAGCT-3' and Seq. 2:
5'-CTTCCCAACGCACCGGACGACGGCCCAGACGGTTCGGGCTGCCGCCGCCGCTGCC    (SEQ ID NO:146)

GCCGCCATGGCTATGGGTATGCAGATGACGGCTATCATATTTG-3'
``` each using T4 polynucleotide kinase (Gibco), mixing the equimolar amounts thereof, heating at 80° C. for 5 minutes, and then slowly cooling to room temperature. The double-stranded DNA fragment thus formed was inserted into the BamHI/SacI site of the plasmid pGEX-C1 as with Example 16, and an *Escherichia coli* (JM109) was transformed using this vector to yield a strain for expression. As with Example 16, the expressed protein aa144-YN2-C1(pht), the amino acid sequence of SEQ ID NO:144 being fused at the N terminal thereof, was purified to give 10 U/mL of a purified enzyme solution. The capability of the purified enzyme binding to copper phthalocyanine was evaluated as in Example 17. The results are shown in Table 16.

TABLE 16

Evaluation of binding affinity of enzyme to copper phthalocyanine

| Enzyme Fusion amino acid sequence | Enzyme activity U |
|---|---|
| aa144- SEQ ID NO:144 YN2-C1 KYDSRHLHTHSHGGGSGGGSPNRLGRRPVRWE (pht) | 0.11 |
| YN2-C1 — | 0.01 |

The enzymes aa144-YN2-C1(pht), in which the copper phthalocyanine affinity sequence was fused, have been confirmed to be higher in enzyme activity and to more effectively immobilize the enzyme on the base material surface than the enzyme YN2-C1, the control.

Example 19

Obtaining of an Amino Acid Sequence Having a Binding Affinity to Carbon Black (1) Carbon black (manufactured by Sigma Aldrich Japan Inc.) was suspended so that it might give a concentration of 5 mg/ml of TBS buffer (50 mM Tris-HCl pH 7.5, 150 mM NaCl) including 0.1% Tween-20. This 10 µl was added to an Eppendorf tube, and TBST buffer (TBS buffer +0.1% Tween-20) 990 µl was added for dilution.

(2) An equivalent for $4\times10^{10}$ pfu of Ph.D.-12 phage display peptide library (manufactured by New England BioLabs Inc.) was added to the tube, which was placed for 10 minutes at 25° C.

1 M Tris-HCl (pH 9.1) 15 µl was added and neutralized to obtain an eluted phage.

(5) *Escherichia coli* ER2537 (manufactured by New England BioLabs Inc.) in early stages of logarithmic growth was infected with the eluted phage, and the phage was amplified. It was cultured at 37° C. for 4.5 hours. Subsequently, the phage was separated from cell by centrifugation, and purified by precipitation in polyethylene glycol. The phage purified and amplified was suspended in TBS buffer, and a titer was measured by infecting *Escherichia coli* with a suitable dilution series.

(6) The above described procedures (1) to (5) were repeated further 4 times using the amplified phage. However, a concentration of Tween-20 in TBST buffer to be used was raised to 0.5%, and conditions of washing were made severer. Henceforth, the same operation was conducted from a second time also to an Eppendorf tube as a control. Titers of phage eluted in each cycle are shown in Table 17.

TABLE 17

Titer of phage eluted in each cycle

| | Stock solution (A) | Control bond (B) | Carbon black bond (C) | C/A | C/B |
|---|---|---|---|---|---|
| First time | $4.0 \times 10^{11}$ | | $8.9 \times 10^6$ | $2.2 \times 10^{-5}$ | |
| Second time | $1.6 \times 10^{11}$ | $1.1 \times 10^5$ | $3.8 \times 10^6$ | $2.4 \times 10^{-5}$ | 35 |
| Third time | $2.0 \times 10^{11}$ | $1.6 \times 10^5$ | $6.0 \times 10^6$ | $3.0 \times 10^{-5}$ | 40 |
| Fourth time | $1.7 \times 10^{11}$ | $1.1 \times 10^6$ | $1.5 \times 10^8$ | $8.8 \times 10^{-4}$ | 140 |
| Fifth time | $1.9 \times 10^{11}$ | $2.0 \times 10^6$ | $2.7 \times 10^9$ | $1.4 \times 10^{-2}$ | 1400 |

(Unit of A, B, and C is Represented by pfu/ml)

A large excessive *Escherichia coli* was infected with the finally eluted phage, and was cloned. After infecting *Escherichia coli* with each of the clone and amplifying the clone, ssDNA was prepared, a base sequence of random domain was decoded and thereby amino acid sequences having a binding affinity to carbon black were obtained. Resulting amino acid sequence and frequency are shown in Table 18.

TABLE 18

Determined amino acid sequence and frequency

| Determined amino acid sequence | | Number (A) | Frequency (A/38) |
|---|---|---|---|
| Trp-Pro-His-Ala-Trp-Lys-Val-Trp-Trp-Pro-Ala-Ser | (SEQ ID NO:39) | 4 | 0.10 |
| Asn-Trp-Trp-Trp-Pro-Pro-Tyr-Ile-Arg-His-Gln-Pro | (SEQ ID NO:40) | 3 | 0.08 |
| Trp-His-Trp-Ser-Trp-Thr-Pro-Trp-Pro-Ser-His-His | (SEQ ID NO:41) | 2 | 0.05 |
| Trp-Pro-Trp-Ala-Trp-His-Pro-Ser-Arg-Asp-Val-Tyr | (SEQ ID NO:42) | 2 | 0.05 |
| Trp-His-Gly-Tyr-Trp-Tyr-Ser-Asn-Leu-Asn-Thr-Thr | (SEQ ID NO:43) | 2 | 0.05 |
| Trp-Trp-Thr-Pro-Trp-Met-Ser-His-Ala-Tyr-Pro-Val | (SEQ ID NO:44) | 2 | 0.05 |
| Trp-Pro-Asn-Pro-Tyr-Trp-Gly-Trp-Phe-Ala-Ala-Val | (SEQ ID NO:45) | 2 | 0.05 |
| Thr-Ser-Trp-His-Thr-Trp-Trp-Trp-Arg-Gln-Pro-Pro | (SEQ ID NO:46) | 2 | 0.05 |
| Asn-Ala-Trp-His-Lys-Tyr-Trp-Trp-Pro-Ile-Thr-Lys | (SEQ ID NO:47) | 2 | 0.05 |
| His-Pro-Asn-Asn-Asp-Trp-Ser-Lys-Ala-Pro-Gln-Phe | (SEQ ID NO:48) | 2 | 0.05 |
| Trp-Trp-Thr-Pro-Gln-Pro-Trp-Trp-Ser-Phe-Pro-Ile | (SEQ ID NO:49) | 1 | 0.03 |
| Trp-Pro-His-Thr-Ser-Trp-Trp-Gln-Thr-Pro-Leu-Thr | (SEQ ID NO:50) | 1 | 0.03 |
| Trp-His-Val-Asn-Trp-Asp-Pro-Met-Ala-Trp-Tyr-Arg | (SEQ ID NO:51) | 1 | 0.03 |
| Ser-Trp-Pro-Trp-Trp-Thr-Ala-Tyr-Arg-Val-His-Ser | (SEQ ID NO:52) | 1 | 0.03 |
| Trp-His-Ser-Asn-Trp-Tyr-Gln-Ser-Ile-Pro-Gln-Val | (SEQ ID NO:53) | 1 | 0.03 |
| Gly-Tyr-Trp-Pro-Trp-Lys-Phe-Glu-His-Ala-Thr-Val | (SEQ ID NO:54) | 1 | 0.03 |
| Ala-Trp-Trp-Pro-Thr-Thr-Phe-Pro-Pro-Tyr-Tyr-Tyr | (SEQ ID NO:55) | 1 | 0.03 |
| Asn-Pro-Trp-Trp-Ser-His-Tyr-Tyr-Pro-Arg-Ser-Val | (SEQ ID NO:56) | 1 | 0.03 |
| Trp-Pro-His-Asn-Tyr-Pro-Leu-Asn-His-Ser-Asn-Pro | (SEQ ID NO:57) | 1 | 0.03 |
| Thr-Trp-Ala-His-Pro-Leu-Glu-Ser-Asp-Tyr-Leu-Arg | (SEQ ID NO:58) | 1 | 0.03 |
| His-Thr-Tyr-Tyr-His-Asp-Gly-Trp-Arg-Leu-Ala-Pro | (SEQ ID NO:59) | 1 | 0.03 |
| Thr-Phe-Val-Gln-Thr-Pro-Leu-Ser-His-Leu-Ile-Ala | (SEQ ID NO:60) | 1 | 0.03 |
| Arg-Val-Pro-Pro-Ser-Lys-Leu-Thr-Arg-Pro-Pro-Phe | (SEQ ID NO:61) | 1 | 0.03 |
| His-Ser-Ile-Tyr-Ser-Val-Thr-Pro-Ser-Thr-Ala-Ser | (SEQ ID NO:62) | 1 | 0.03 |
| Leu-Asn-Thr-Gln-Asn-His-Ala-Pro-Leu-Pro-Ser-Ile | (SEQ ID NO:63) | 1 | 0.03 |

Example 20

A PHA synthase having a binding affinity to carbon black was prepared as follows. An *Escherichia coli* expression vector expressed by fusing to N terminal of a PHA synthase through a spacer sequence GS to each amino acid sequence (from SEQ ID NO:39 to SEQ ID NO:63) was built as follows. In DNA encoding these amino acid sequences, since it was manufactured as a double stranded synthetic DNA, a set of synthetic oligonucleotides in next table 19 were prepared.

TABLE 19

Synthetic DNA set for expressing each amino acid sequence

| SEQ ID NO: amino acid sequence | SEQ ID NO: base sequence of synthetic DNA | |
|---|---|---|
| SEQ ID NO:39 WPHAWKVWWPAS | 5'-GATCCTGGCCGCATGCGTGGAAAGTGTGGTGGCCGGCGAGCGAGCT-3' | SEQ ID NO:94 |
| | 5'-CGCTCGCCGGCCACCACACTTTCCACGCATGCGGCCAG-3' | SEQ ID NO:95 |

TABLE 19-continued

Synthetic DNA set for expressing each amino acid sequence

| SEQ ID NO: amino acid sequence | SEQ ID NO: base sequence of synthetic DNA | |
|---|---|---|
| SEQ ID NO:40 | 5'-GATCCAACTGGTGGTGGCCGCCGTATATTCGTCATCAGCCGGAGCT-3' | SEQ ID NO:96 |
| NWWWPPYIRHQP | 5'-CCGGCTGATGACGAATATACGGCGGCCACCACCAGTTG-3' | SEQ ID NO:97 |
| SEQ ID NO:41 | 5'-GATCCTGGCATTGGAGCTGGACCCCGTGGCCGAGCCATCATGAGCT-3' | SEQ ID NO:98 |
| WHWSWTPWPSHH | 5'-CATGATGGCTCGGCCACGGGGTCCAGCTCCAATGCCAG-3' | SEQ ID NO:99 |
| SEQ ID NO:42 | 5'-GATCCTGGCCGTGGGCGTGGCATCCGAGCCGTGATGTGTATGAGCT-3' | SEQ ID NO:100 |
| WPWAWHPSRDVY | 5'-CATACACATCACGGCTCGGATGCCACGCCCACGGCCAG-3' | SEQ ID NO:101 |
| SEQ ID NO:43 | 5'-GATCCTGGCATGGCTATTGGTATAGCAACCTGAACACCACCGAGCT-3' | SEQ ID NO:102 |
| WHGYWYSNLNTT | 5'-CGGTGGTGTTCAGGTTGCTATACCAATAGCCATGCCAG-3' | SEQ ID NO:103 |
| SEQ ID NO:44 | 5'-GATCCTGGTGGACCCCGTGGATGAGCCATGCGTATCCGGTGGAGCT-3' | SEQ ID NO:104 |
| WWTPWMSHAYFV | 5'-CCACCGGATACGCATGGCTCATCCACGGGGTCCACCAG-3' | SEQ ID NO:105 |
| SEQ ID NO:45 | 5'-GATCCTGGCCGAACCCGTATTGGGGCTGGTTTGCGGCGGTGGAGCT-3' | SEQ ID NO:106 |
| WPNPYWGWFAAV | 5'-CCACCGCCGCAAACCAGCCCCAATACGGGTTCGGCCAG-3' | SEQ ID NO:107 |
| SEQ ID NO:46 | 5'-GATCCACCAGCTGGCATACCTGGTGGTGGCGTCAGCCGCCGGAGCT-3' | SEQ ID NO:108 |
| TSWHTWWWRQPP | 5'-CCGGCGGCTGACGCCACCACCAGGTATGCCAGCTGGTG-3' | SEQ ID NO:109 |
| SEQ ID NO:47 | 5'-GATCCAACGCGTGGCATAAATATTGGTGGCCGATTACCAAAGAGCT-3' | SEQ ID NO:110 |
| NAWHKYWWPITK | 5'-CTTTGGTAATCGGCCACCAATATTTATGCCACGCGTTG-3' | SEQ ID NO:111 |
| SEQ ID NO:48 | 5'-GATCCCATCCGAACAACGATTGGAGCAAAGCGCCGCAGTTTGAGCT-3' | SEQ ID NO:112 |
| HPNNDWSKAPQF | 5'-CAAACTGCGGCGCTTTGCTCCAATCGTTGTTCGGATGG-3' | SEQ ID NO:113 |
| SEQ ID NO:49 | 5'-GATCCTGGTGGACCCCGCAGCCGTGGTGGAGCTTTCCGATTGAGCT-3' | SEQ ID NO:114 |
| WWTPQPWWSFPI | 5'-CAATCGGAAAGCTCCACCACGGCTGCGGGGTCCACCAG-3' | SEQ ID NO:115 |
| SEQ ID NO:50 | 5'-GATCCTGGCCGCATACCAGCTGGTGGCAGACCCCGCTGACCGAGCT-3' | SEQ ID NO:116 |
| WPHTSWWQTPLT | 5'-CGGTCAGCGGGGTCTGCCACCAGCTGGTATGCGGCCAG-3' | SEQ ID NO:117 |
| SEQ ID NO:51 | 5'-GATCCTGGCATGTGAACTGGGATCCGATGGCGTGGTATCGTGAGCT-3' | SEQ ID NO:118 |
| WHVNWDPMAWYR | 5'-CACGATACCACGCCATCGGATCCCAGTTCACATGCCAG-3' | SEQ ID NO:119 |
| SEQ ID NO:52 | 5'-GATCCAGCTGGCCGTGGTGGACCGCGTATCGTGTGCATAGCGAGCT-3' | SEQ ID NO:120 |
| SWPWWTAYRVHS | 5'-CGCTATGCACACGATACGCGGTCCACCACGGCCAGCTG-3' | SEQ ID NO:121 |
| SEQ ID NO:53 | 5'-GATCCTGGCATAGCAACTGGTATCAGAGCATTCCGCAGGTGGAGCT-3' | SEQ ID NO:122 |
| WHSNWYQSIPQV | 5'-CCACCTGCGGAATGCTCTGATACCAGTTGCTATGCCAG-3' | SEQ ID NO:123 |
| SEQ ID NO:54 | 5'-GATCCGGCTATTGGCCGTGGAAATTTGAACATGCGACCGTGGAGCT-3' | SEQ ID NO:124 |
| GYWPWKFEHATV | 5'-CCACGGTCGCATGTTCAAATTTCCACGGCCAATAGCCG-3' | SEQ ID NO:125 |
| SEQ ID NO:55 | 5'-GATCCGCGTGGTGGCCGACCACCTTTCCGCCGTATTATTATGAGCT-3' | SEQ ID NO:126 |
| AWWPTTFPPYYY | 5'-CATAATAATACGGCGGAAAGGTGGTCGGCCACCACGCG-3' | SEQ ID NO:127 |
| SEQ ID NO:56 | 5'-GATCCAACCCGTGGTGGAGCCATTATTATCCGCGTAGCGTGGAGCT-3' | SEQ ID NO:128 |
| NPWWSHYYPRSV | 5'-CCACGCTACGCGGATAATAATGGCTCCACCACGGGTTG-3' | SEQ ID NO:129 |
| SEQ ID NO:57 | 5'-GATCCTGGCCGCATAACTATCCGCTGAACCATAGCAACCCGGAGCT-3' | SEQ ID NO:130 |
| WPHNYPLNHSNP | 5'-CCGGGTTGCTATGGTTCAGCGGATAGTTATGCGGCCAG-3' | SEQ ID NO:131 |

TABLE 19-continued

Synthetic DNA set for expressing each amino acid sequence

| SEQ ID NO:<br>amino acid<br>sequence | SEQ ID NO: base sequence of synthetic DNA | |
|---|---|---|
| SEQ ID NO:58 | 5'-GATCCACCTGGGCGCATCCGCTGGAAAGCGATTATCTGCGTGAGCT-3' | SEQ ID NO:132 |
| TWAHPLESDYLR | 5'-CACGCAGATAATCGCTTTCCAGCGGATGCGCCCAGGTG-3' | SEQ ID NO:133 |
| SEQ ID NO:59 | 5'-GATCCCATACCTATTATCATGATGGCTGGCGTCTGGCGCCGGAGCT-3' | SEQ ID NO:134 |
| HTYYHDGWRLAP | 5'-CCGGCGCCAGACGCCAGCCATCATGATAATAGGTATGG-3' | SEQ ID NO:135 |
| SEQ ID NO:60 | 5'-GATCCACCTTTGTGCAGACCCCGCTGAGCCATCTGATTGCGGAGCT-3' | SEQ ID NO:136 |
| TFVQTPLSHLIA | 5'-CCGCAATCAGATGGCTCAGCGGGGTCTGCACAAAGGTG-3' | SEQ ID NO:137 |
| SEQ ID NO:61 | 5'-GATCCCGTGTGCCGCCGAGCAAACTGACCCGTCCGCCGTTTGAGCT-3' | SEQ ID NO:138 |
| RVPPSKLTRPPF | 5'-CAAACGGCGGACGGGTCAGTTTGCTCGGCGGCACACGG-3' | SEQ ID NO:139 |
| SEQ ID NO:62 | 5'-GATCCCATAGCATTTATAGCGTGACCCCGAGCACCGCGAGCGAGCT-3' | SEQ ID NO:140 |
| HSIYSVTPSTAS | 5'-CGCTCGCGGTGCTCGGGGTCACGCTATAAATGCTATGG-3' | SEQ ID NO:141 |
| SEQ ID NO:63 | 5'-GATCCCTGAACACCCAGAACCATGCGCCGCTGCCGAGCATTGAGCT-3' | SEQ ID NO:142 |
| LNTQNHAPLPSI | 5'-CAATGCTCGGCAGCGGCGCATGGTTCTGGGTGTTCAGG-3' | SEQ ID NO:143 |

Two kinds of synthetic DNA to each amino acid sequence mentioned in Table 19 was phosphorylated, according to description of manufacturer, using a T4 polynucleotide kinase (manufactured by Gibco). Subsequently, equi-molar amounts of two kinds of synthetic DNA were mixed and heated for 5 minutes at 80° C., cooled slowly to room temperature, and a double stranded DNA fragment was formed. The formed double stranded DNA fragment was directly used for subsequent cloning.

Plasmid pGEX-C1 was digested by BamHI and SacI, and the above described double stranded DNA fragment was inserted. An *Escherichia coli* (JM109) was transformed using this vector, and a strain for expression was obtained. Check of the strain was conducted by determining a base sequence of insertion by a sequencing using pGEX5' Sequencing Primer (manufactured by Amasham Pharmasia Biotech Corp.) and using a plasmid DNA prepared by Miniprep (Wizard Minipreps DNA Purification Systems, manufactured by PROMEGA) as a template. After carrying out pre-culture of the obtained strain by LB-Amp culture medium 10 mL overnight, 0.1 mL of a resultant containing the strain was added to LB-Amp culture medium of 10 mL, and shake culture was carried out at 37° C. and 170 rpm for 3 hours. IPTG was then added (final concentration 1 mM), and cultivation was continued at 37° C. for 4 to 12 hours.

IPTG induced *Escherichia coli* was harvested (8000×g, 2 minutes, 4° C.), and it was re-suspended in 4-degree C. PBS of 1/10 amount. Cell was crushed by freeze thawing and sonication, cell debris was removed by centrifugation (8000×g, 10 minutes, 4° C.). After it was confirmed by SDS-PAGE that target expression protein existed in supernatant, the GST fusion protein induced and expressed was purified with glutathione Sepharose 4B (Glutathion Sepharose 4B beads: manufactured by Amasham Pharmasia Biotech Corp.)

A treatment controlling nonspecific adsorption was beforehand given to the glutathione sepharose used. That is, after the glutathione sepharose was washed (8000×g, 1 minute, 4° C.) 3 times by a same amount of PBS, it was treated with a same amount of PBS including 4% BSA added at 4° C. for 1 hour. It was washed twice by a same amount of PBS after treatment, and was re-suspended in ½ amount of PBS. The pretreated glutathione sepharose 40 μL was added to a cell free extract 1 mL, and calmly stirred at 4° C. Thereby, fusion proteins GST-aa39-YN2-C1 to GST-aa63-YN2-C1 were adsorbed to glutathione sepharose. [In fusion protein GST-aa##-YN2-C1, aa## means that polypeptide comprising amino acid sequence of SEQ ID NO:## is expressed by being fused between PHA synthase and GST.]

The glutathione sepharoses were collected by centrifugation (8000×g, 1 minute, 4° C.) after adsorption, and washing was performed 3 times with PBS 400 μL. Subsequently, 10 mM reduced glutathione 40 μL was added and stirred at 4° C. for 1 hour and the fusion protein adsorbed was eluted out. After centrifugation (8000×g, 2 minutes, 4° C.), supernatants were collected, and dialyzed to PBS to purify GST fusion protein. It was confirmed that single band was given by SDS-PAGE.

After each of the GST fusion protein 500 μg was digested by PreScission protease (Amasham Pharmasia Biotech Corp., 5U), the protease and GST were removed through glutathione sepharose. Flow through fraction was further processed by Sephadex G200 column equilibrated by PBS to obtain final purified expression proteins aa39-YN2-C1(cb) to aa63-YN2-C1(cb). [In expression protein aa##-YN2-C1 (cb), aa## means that a polypeptide comprising amino acid sequence of SEQ ID NO:## is expressed by being fused with N terminal of PHA synthase.]

Activity of each purified enzyme was measured by the above described procedure. Moreover, a protein concentration in samples was measured with micro BCA protein determination reagent kit (manufactured by Pierce Chemical com.). Enzyme concentration was 1.9 U/ml and specific activity was 4.0 U/mg protein. Purified enzyme was concentrated using organism solution sample concentration agent (Mizubutorikun AB-1100, manufactured by ATTO Corporation) to obtain 10 U/ml purified enzyme solution.

Example 21

Evaluation of a Binding Affinity to Carbon Black

Carbon black was suspended in TBS buffer containing 0.1% Tween-20 so that it might become 0.5% (w/v). This suspension 10 ml was sampled into a centrifuge tube made of Teflon, an equivalent for 0.5 U of PHA synthase aa39-YN2-C1(cb) to aa63-YN2-C1(cb) prepared in Example 20 and YN2-C1 prepared in Reference Example 1 were added to this suspension, and the resultant solution was shaken for 30 minutes at room temperature. By centrifugation operation (for 10,000×g, 4° C., and 10 minutes), carbon black particles were collected as precipitation and separated from supernatant containing enzyme not binding to the carbon black. The carbon black was suspended in TBS buffer containing 0.1% Tween-20, a centrifugal operation was repeated, whereby the carbon black was washed. Results of having measured an enzyme activity of the suspension of the washed carbon black are shown in Table 20.

TABLE 20

Evaluation of binding affinity of enzyme to carbon black

| Enzyme | Fusion amino acid sequence | Enzyme activity U |
|---|---|---|
| aa39-YN2-C1 (cb) | SEQ ID NO:39 WPHAWKVWWPAS | 0.06 |
| aa40-YN2-C1 (cb) | SEQ ID NO:40 NWWWPPYIRHQP | 0.06 |
| aa41-YN2-C1 (cb) | SEQ ID NO:41 WHWSWTPWPSHH | 0.05 |
| aa42-YN2-C1 (cb) | SEQ ID NO:42 WPWAWHPSRDVY | 0.05 |
| aa43-YN2-C1 (cb) | SEQ ID NO:43 WHGYWYSNLNTT | 0.05 |
| aa44-YN2-C1 (cb) | SEQ ID NO:44 WWTPWMSHAYPV | 0.05 |
| aa45-YN2-C1 (cb) | SEQ ID NO:45 WPNPYWGWFAAV | 0.05 |
| aa46-YN2-C1 (cb) | SEQ ID NO:46 TSWHTWWWRQPP | 0.05 |
| aa47-YN2-C1 (cb) | SEQ ID NO:47 NAWHKYWWPITK | 0.05 |
| aa48-YN2-C1 (cb) | SEQ ID NO:48 HPNNDWSKAPQF | 0.05 |
| aa49-YN2-C1 (cb) | SEQ ID NO:49 WWTPQPWWSFPI | 0.05 |
| aa50-YN-uC1 (cb) | SEQ ID NO:50 WPHTSWWQTPLT | 0.05 |
| aa51-YN2-C1 (cb) | SEQ ID NO:51 WHVNWDPMAWYR | 0.05 |
| aa52-YN2-C1 (cb) | SEQ ID NO:52 SWPWWTAYRVHS | 0.04 |
| aa53-YN2-C1 (cb) | SEQ ID NO:53 WHSNWYQSIPQV | 0.04 |
| aa54-YN2-C1 (cb) | SEQ ID NO:54 GYWPWKFEHATV | 0.04 |
| aa55-YN2-C1 (cb) | SEQ ID NO:55 AWWPTTFPPYYY | 0.04 |
| aa56-YN2-C1 (cb) | SEQ ID NO:56 NPWWSHYYPRSV | 0.04 |
| aa57-YN2-C1 (cb) | SEQ ID NO:57 WPHNYPLNHSNP | 0.04 |
| aa58-YN2-C1 (cb) | SEQ ID NO:58 TWAHPLESDYLR | 0.04 |
| aa59-YN2-C1 (cb) | SEQ ID NO:59 HTYYHDGWRLAP | 0.04 |
| aa60-YN2-C1 (cb) | SEQ ID NO:60 TFVQTPLSHLIA | 0.04 |
| aa61-YN2-C1 (cb) | SEQ ID NO:61 RVPPSKLTRPPF | 0.04 |
| aa62-YN2-C1 (cb) | SEQ ID NO:62 HSIYSVTPSTAS | 0.04 |
| aa63-YN2-C1 (cb) | SEQ ID NO:63 LNTQNHAPLPSI | 0.04 |
| YN2-C1 | — | 0.01 |

It was confirmed that the enzyme aa39-YN2-C1(cb) to aa63-YN2-C1(cb) fused with a carbon black affinity sequence had a higher enzyme activity compared with the enzyme YN2-C1 of control, and thus could be effectively immobilized on a base material surface.

Example 22

Two kinds of amino acid sequences capable of binding to carbon black, Trp-Pro-His-Ala-Trp-Lys-Val-Trp-Trp-Pro-Ala-Ser (SEQ ID NO:39) and Asn-Trp-Trp-Trp-Pro-Pro-Tyr-Ile-Arg-His-Gln-Pro (SEQ ID NO:40), were all connected in the indicated order in series through the spacer sequence Gly-Gly-Gly-Gly-Gly-Ser-Gly-Gly-Gly-Ser (SEQ ID NO:181) to give Trp-Pro-His-Ala-Trp-Lys-Val-Trp-Trp-Pro-Ala-Ser-Gly-Gly-Gly-Ser-Gly-Gly-Gly-Ser-Asn-Trp-Trp-Pro-Pro-Tyr-Ile-Arg-His-Gln-Pro (SEQ ID NO:147), which was further fused to the N terminal of a PHA synthase through the use of the spacer sequence GS to prepare an *Escherichia coli* expression vector in the following. The DNA encoding this amino acid sequence was formed as a double-stranded DNA fragment by, after phosphorylating Seq. 1:
5'-GATCCTGGCCGCATGCGTGGAAAGTGTGGTGGCCGGCGAGCGGCGGCGGCAGCGG (SEQ ID NO:148)

CGGCGGCAGCAACTGGTGGTGGCCGCCGTATATTCGTCATCAGCCGGAGCT-3' and Seq. 2:
5'-CCGGCTGATGACGAATATACGGCGGCCACCACCAGTTGCTGCCGCCGCCGCTGCC (SEQ ID NO:149)

GCCGCCGCTCGCCGGCCACCACACTTTCCACGCATGCGGCCAG-3' each using T4 polynucleotide kinase (Gibco), mixing the equimolar amounts thereof, heating at 80° C. for 5 minutes, and then slowly cooling to room temperature. The double-stranded DNA fragment thus formed was inserted into the BamHI/SacI site of the plasmid pGEX-C1 as with Example 20, and an *Escherichia coli* (JM109) was transformed using this vector to yield a strain for expression. As with Example 20, the expressed protein aa147-YN2-C1(cb), the amino acid sequence of SEQ ID NO:147 being fused at the N terminal thereof, was purified to give 10 U/mL of a purified enzyme solution. The capability of the purified enzyme binding to carbon black was evaluated as in Example 21. The results are shown in Table 21.

3-hydroxy-5-phenoxy valeric acid, and subsequently treating this was treated by a method in Eur. J. Biochem., 250, 432–439 (1997), and bovine serum albumin (manufactured by Sigma-Aldrich Com.) 0.1 mass part were added hereto. The resultant mixture was shaken gently at 30° C. for 2 hours. A blue microencapsulated pigment produced (hereinafter referred to as coloring agent) was filtrated, washed and dried, coloring agent 1 was thus obtained.

After vacuum drying of this coloring agent 1, it was suspended in chloroform 20 mL, agitated at 60° C. for 20 hours, and polymer constituting pellicle was extracted. After the extract was filtered by a membrane filter having 0.45 micrometers of pore sizes and vacuum-concentrated by a

TABLE 21

| Enzyme | Evaluation of binding affinity of enzyme to carbon black | |
|---|---|---|
| | Fusion amino acid sequence | Enzyme activity U |
| aa147-YN2-C1 (cb) | SEQ ID NO: 147 WPHAWKVWWPASGGGSGGGSNWWWPPYIRHQP | 0.15 |
| YN2-C1 | — | 0.01 |

The enzymes aa147-YN2-C1(cb), in which the carbon black affinity sequence was fused, have been confirmed to be higher in enzyme activity and to more effectively immobilize the enzyme on the base material surface than the enzyme YN2-C1, the control.

Example 23

Preparation and Evaluation of an Electrostatic Charge Image Development Toner

Copper phthalocyanine was dispersed by a sand mill so that no more than 0.1 micrometers of particle diameter might be given, 39 parts by mass of PBS buffer containing 0.1% Tween-20 was added to this copper phthalocyanine 1 mass part and suspended. This suspension 10 ml was sampled into a centrifuge tube made of Teflon, an equivalent for 4U of PHA synthase aa24-YN2-C1 (pht) prepared in Example 16 was added hereto, shaken for 30 minutes at room temperature to cause the PHA synthase to be absorbed on the pigment surface. Centrifugation (for 98,000 m/s$^2$ (10,000G), 4° C., and 10 minutes) was given to this, the precipitation was suspended in PBS solution, centrifugation (for 98,000 m/s$^2$ (10,000G), 4° C., and 10 minutes) was given again, to immobilize the PHA synthase to copper phthalocyanine.

Each of the above described immobilized enzyme was suspended in 0.1 M phosphoric acid buffer (pH 7.0) 48 parts by mass. Subsequently (R,S)-3-hydroxy-5-phenoxyvaleryl CoA 1 mass part, which had been prepared by hydrolyzing 3-hydroxy-5-phenoxy valerianate obtained by Reformatsky reaction with zinc using 3-phenoxy propanal and ethyl bromoacetate that were synthesized by a method given in J. Org. Chem., 55, 1490–1492 (1990) as materials, to obtain rotating evaporator, methanolysis was conducted according to a conventional method and the resultant product was analyzed by a gas chromatography mass spectrometry equipment (GC-MS, Shimadzu QP, 5050, EI method). As a result, it was confirmed that a main component of the pellicle of the obtained coloring agent 1 was a PHA comprising 3-hydroxy-5-phenoxy valeric acid unit.

Moreover, the PHA was evaluated for a molecular weight by a gel permeation chromatography (GPC; TOSOH CORPORATION HLC-8020, column; Polymer Laboratory PLgel MIXED-C (5 micrometers), solvent; chloroform, column temperature; 40° C., polystyrene calibrated), and Mn=29,000 was given.

Furthermore, the pigment before and after microencapsulation was measured for a volume mean particle diameter using a laser Doppler system particle size distribution measurement machine (UPA-150; manufactured by NIKKISO Co., LTD.). Results are summarized in Table 22.

Subsequently, the following materials for a composition were mixed, melted and kneaded by a biaxial extruder (L/D=30):

styrene-butyl acrylate copolymer resin (70° C. of glass transition temperature): 100 parts by mass,
coloring agent 1:5 parts by mass,
charge control agent (manufactured by Hoechst: NXVP 434): 2 parts by mass.

After the kneaded mixture was cooled, rough-ground by a hammer mill, pulverized with jet mill and classified to obtain a cyan coloring particle (1) by a grinding method. In grain size of the cyan coloring particle (1), a weight mean particle diameter of 7.1 micrometers and an amount of fine powders of 6.0 number-% were given.

To the cyano coloring particle (1) 100 parts by mass, hydrophobic silica fine powder 1.5 parts by mass (BET: 250 m²/g) processed by hexamethyldisilazane as a flow improver was dry-blended by Henschel Mixer to obtain a cyan toner (1) of the Example. Furthermore, the obtained cyan toner (1) 7 parts by mass and a resin coated magnetic ferrite carrier (mean particle diameter: 45 micrometers) 93 parts by mass were mixed, to prepare and two-component system cyan developer for magnetic brush development (1), followed by performing evaluations mentioned later.

Comparative Example 1

The same method as in Example 23 except that YN2-C1 was used instead of PHA synthase aa24-YN2-C1 (pht) was carried out to obtain cyano toner (2). Furthermore, the same method as in Example 23 was repeated using this toner to obtain a two-component system cyan developer (2). This toner was evaluated for characteristics as in Example 23.

Comparative Example 2

The same method as in Example 23 except that an equivalent for 10 U of YN2-C1 was used instead of an equivalent for 4 U of PHA synthase aa24-YN2-C1 (pht) was carried out to obtain cyano toner (3). Furthermore, the same method as in Example 23 was repeated using the toner to obtain a two-component system cyan developer (3). This toner was evaluated for characteristics as in Example 23.

Comparative Example 3

The same method as in Example 23 except that copper phthalocyanine 5 parts by mass were used instead of the coloring agent 1 was carried out to obtain a cyan toner (4). Furthermore, the same method as in Example 23 was repeated using the toner to obtain a two-component system cyan developer (4). This toner was evaluated for characteristics as in Example 23.

<Evaluation 1>

The amounts of toners charged were measured for the aforementioned developing agents (1), (2), (3) and (4) under environments of a normal temperature and humidity (25° C., 60% RH) and a high temperature and humidity (30° C., 80% RH) after agitation for 10 seconds and 300 seconds. The results are summarized in Table 22.

The sizes of pigments before and after microencapsulation show that the microencapsulation of the pigment in Comparative Example 1 is not sufficient as compared with that in Comparative Example 2. This seems to be because the amount of enzyme added to the pigment in Comparative Example 1 was smaller than the case of Comparative Example 2. On the other hand, the amount of enzyme added in Example 23 was the same as that in Comparative Example 1; however, the microencapsulation is almost equivalent to that of Comparative Example 2, showing large amount of its charge.

As a result, Example 23 can microencapsulate a pigment by means of a small amount of an enzyme, indicating that it can effectively increase the amount of toner charged.

Figure 4:
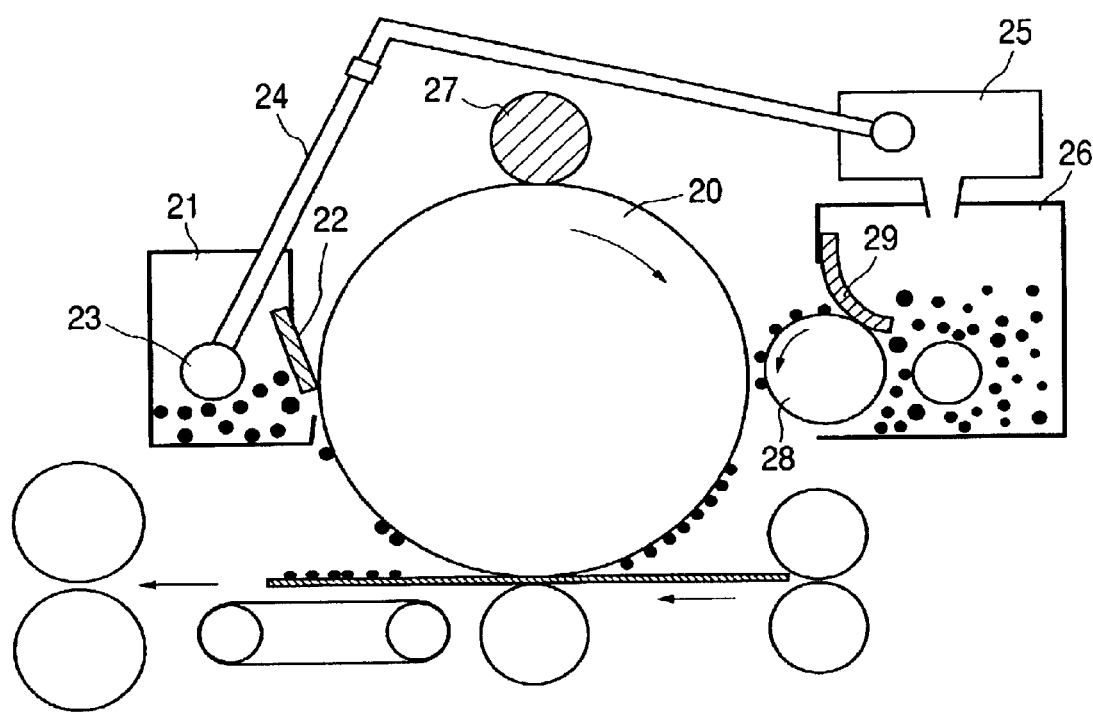
FIG. 4 shows a schematic diagram of a image forming apparatus having a reuse mechanism of a toner.

Next, image formation was conducted using the aforementioned coloring agent. An image forming apparatus reset and improved by installing a reuse mechanism in a commercially available laser beam printer LBP-EX (Canon Inc.) was employed as means of forming an image, as illustrated in FIG. 4. In other words, an image forming apparatus as shown in FIGS. 3A and 3B is provided with an operating system that includes scraping off an imprinted toner remaining on a photoconductor drum 20 by an elastic blade 22 of a cleaner 21 touching to the photoconductor drum 20 after printing, transporting the toner to the inside of the cleaner 21 by a cleaner roller, further passing it through cleaner reuse 23, returning the toner to a developing device 26 through a hopper 25 by means of a pipe 24 for supply equipped with a transport screw, and again reusing the recovered toner.

In the image forming apparatus as illustrated in FIG. 4, the surface of the photoconductor drum 20 is charged by a primary charging roller 27. A rubber roller (diameter 12 mm, touching pressure 50 g/cm) on which conductive carbon is dispersed, coated with nylon resin, was used for the primary charging roller 27 to form an electrostatic latent image with a dark space voltage VD=−700 V and a bright space voltage VL=−200 V on the electrostatic latent image supporter (photoconductor drum 20) by means of laser light exposure (600 dpi, not shown in the figure). As a toner supporter was used a developing sleeve 28, the surface of which is coated with resin in which Carbon Black is dispersed, with a surface roughness Ra of 1.1.

Figure 5:
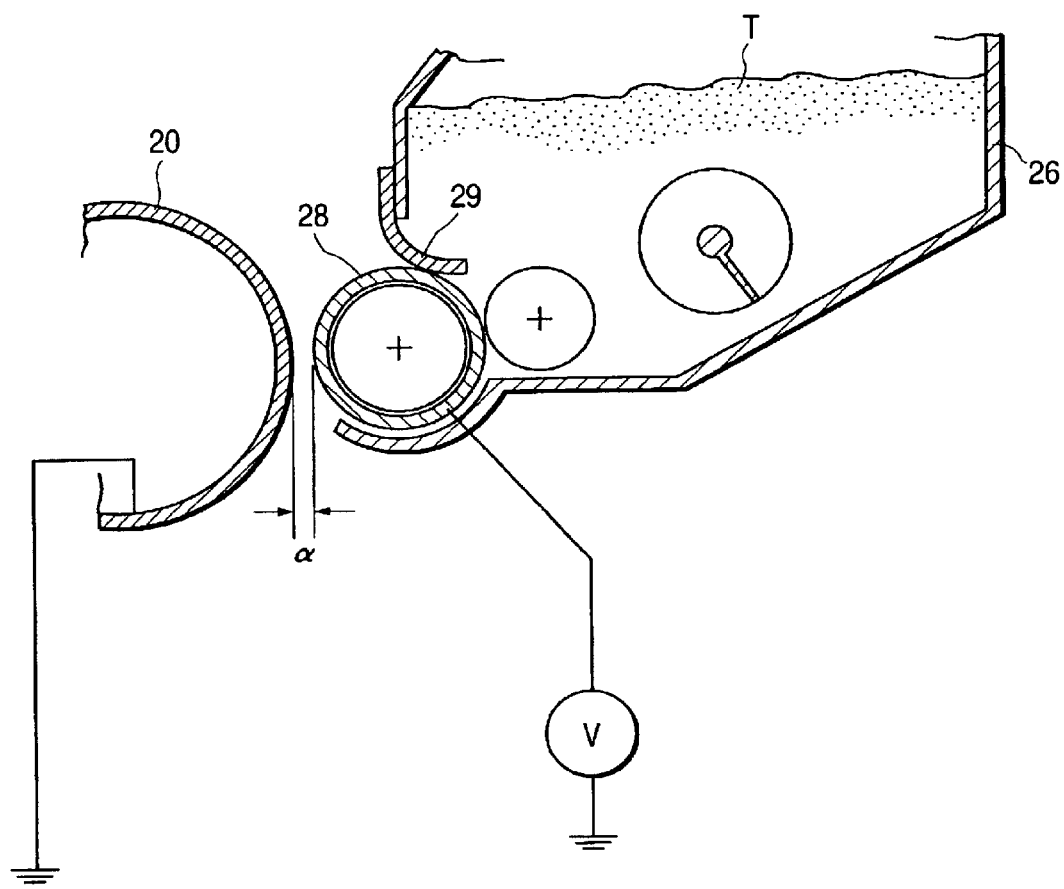
FIG. 5 shows a sectional view of the main portion of a developing apparatus for a one-component developing agent.

FIG. 5 shows an enlarged sectional view of the main portion of a developing apparatus for a one-component developing agent used in Example 24 and Comparative Example 2. For conditions of developing an electrostatic latent image, the speed of the developing sleeve 28 was set to be 1.1 times the moving speed of the opposing face of the

TABLE 22

Figure 6:
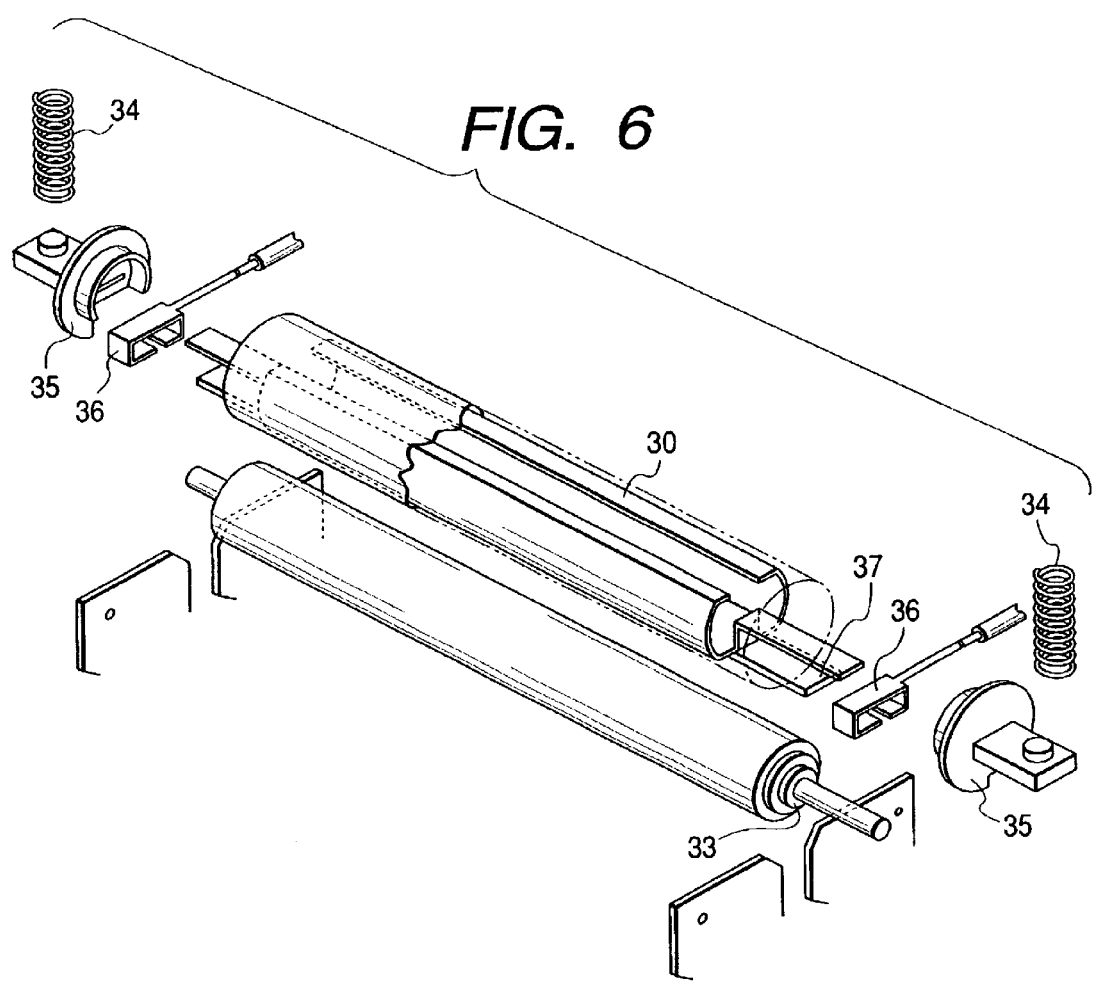
FIG. 6 shows an exploded perspective view of the main portion of a fixation apparatus.
Figure 7:
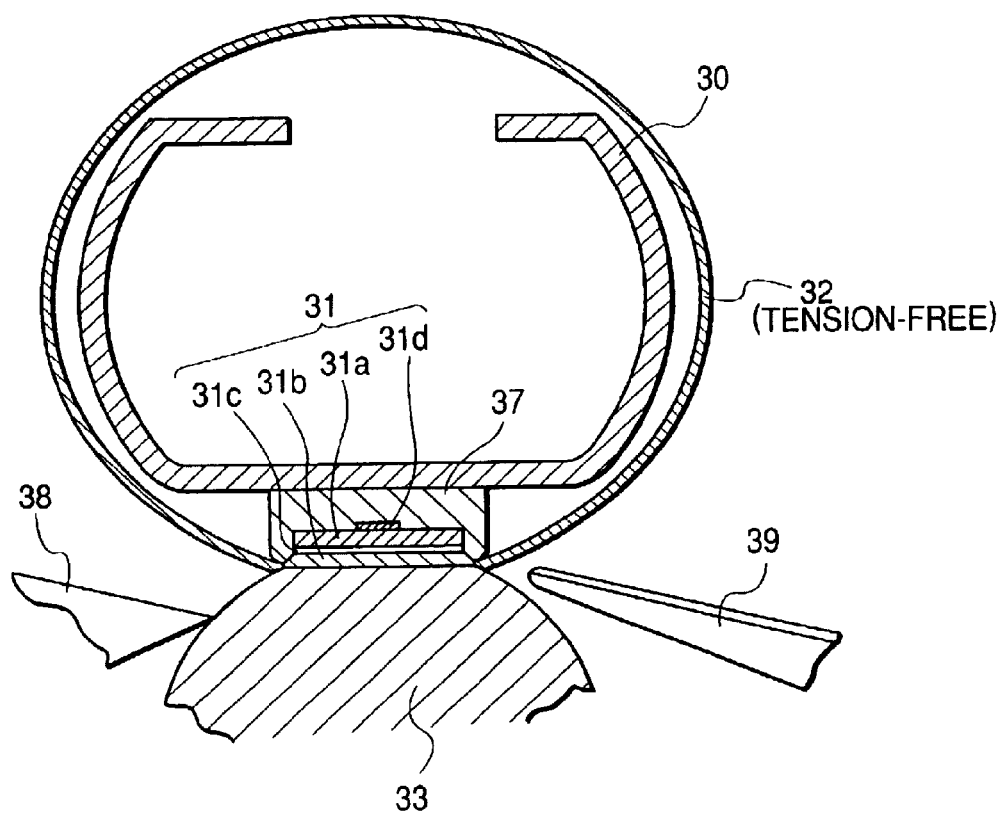
FIG. 7 shows an enlarged sectional view of the main portion that illustrates a film condition when the fixation apparatus is not run.

| | Toner number | Pigment particle size Prior to microencapsulation (μm) | Pigment particle size Subsequent to making microencapsulation (μm) | Amount of charge at normal temperature and humidity (μC/g) 10-second agitation | Amount of charge at normal temperature and humidity (μC/g) 300-second agitation | Amount of charge at high temperature and humidity (μC/g) 10-second agitation | Amount of charge at high temperature and humidity (μC/g) 300-second agitation |
|---|---|---|---|---|---|---|---|
| Example 23 | 1 | 0.804 | 0.102 | −23.6 | −27.7 | −22.1 | −26.5 |
| Comparative Example 1 | 2 | 0.796 | 0.853 | −20.9 | −25.3 | −18.3 | −22.4 |
| Comparative Example 2 | 3 | 0.811 | 0.107 | −24.1 | −27.5 | −21.8 | −26.4 |
| Comparative Example 3 | 4 | | 0.808 | −18.4 | −14.8 | −14.1 | −19.6 | photoconductor drum 20 and further the space α (between S and D) between the photoconductor drum 20 and the developing sleeve 28 was set to be 270 μm. An urethane rubber blade 29 was touched for use as a member of regulating the layer thickness of a toner. In addition, a heating fixation apparatus for fixing a toner image was set at a temperature of 160° C. Furthermore, a fixing apparatus shown in FIGS. 6 and 7 was used.

As described above, at normal temperature and humidity (25° C., 60% RT), 30,000 sheets were printed out at a print out speed of 8 sheets (A4 size)/minute at a continuous mode (namely, a mode of increasing consumption of a toner without stopping the developing device) while supplying a toner successively. The image concentrations were measured for the print out images obtained to evaluate their endurance based on the criteria indicated below. In addition, the 10,000th image was observed to evaluate image fog based on the criteria indicated below. Additionally, at the same time, the state of each unit constituting the image forming apparatus after endurance testing was observed to evaluate the matching between each unit and each of the aforementioned toners as well. The results obtained are given in Table 23.

(Image Concentration Transition During Endurance)

A given number of normal paper sheets (75 g/m2) for an ordinary printer were printed out to evaluate the degree of image concentration holding of an image at the end of printing with respect to that of the initial image. Additionally, a Macbeth reflectometer (Macbeth Corp.) was used to measure an image concentration relative to a white part of a print out image with a manuscript concentration of 0.00 for evaluation.

A: Excellent (An image concentration at the end of printing is 1.40 or more.)
B: Good (An image concentration at the end of printing is 1.35 or more and less than 1.40.)
C: Pass (An image concentration at the end of printing is 1.00 or more and less than 1.35.)
D: Fail (An image concentration at the end of printing is less than 1.00.)

(Image Fog)

A given number of normal paper sheets (75 g/m2) for an ordinary printer were printed out for evaluation on the basis of solid white shaded images at the end of printing. More specifically, evaluation was conducted in the following manner.

The worst value of the white part reflection concentration after printing and the average reflection concentration of sheets before printing, measured using a reflectometer (Reflectometer Odel TC-6DS, Tokyo Denshoku Co., Ltd.), were denoted as Ds and Dr, respectively. The difference (Ds minus Dr) was taken as the amount of fog and evaluated in the following criteria.

A: Excellent (The amount of fog is 0% or more and less than 1.5%)
B: Good (The amount of fog is 1.5% or more and less than 3.0%)
C: Practicable (The amount of fog is 3.0% or more and less than 5.0%)
D: Impracticable (The amount of fog is 5.0% or more)

(Matching Evaluation for the Image Forming Apparatus)

1. Matching with Developing Sleeve

The state of fixation of a remaining toner on the developing sleeve surface and the effect of the remaining toner on a print out image after print out testing were visually evaluated.

A: Excellent (Not occur)
B: Good (Almost not occur)
C: Practicable (Fixation is present, but the effect on an image is small)
D: Impracticable (A large amount of fixation is present, which causes a nonuniform image)

2. Matching with Photoconductor Drum

Scratches on the photoconductor drum surface and the state of occurrence of remaining toner fixation and their effects on print out images were visually evaluated.

A: Excellent (Not occur)
B: Good (Scratches are slightly generated, but do not affect the image)
C: Practicable (Fixation and scratches are present, but do not affect the image so much)
D: Impracticable (A large amount of fixation is present, which gives rise to vertical line-like image defects)

3. Matching with Fixing Apparatus

The state of the fixation film surface was observed to obtain the results of the surface properties and the states of fixation of remaining toners. The results were averaged to evaluate endurance properties.

(1) Surface Properties

States of scratches and scrapes on the fixed film surface after print out testing were visually observed and evaluated.

A: Excellent (Not occur)
B: Good (Almost not occur)
C: Practicable
D: Impracticable (2) Fixation State of Remaining Toners Fixation states of remaining toners on the fixed film surface after print out testing were visually observed and evaluated.

A: Excellent (Not occur)
B: Good (Almost not occur)
C: Practicable
D: Impracticable

TABLE 23

| | | Print out image evaluation | | | | Matching evaluation for each unit | | | |
|---|---|---|---|---|---|---|---|---|---|
| | | Image concentration transition during endurance | | | | Image fog | | Photo- | Fixing unit |
| | Toner | Initial stage | 1,000 sheets | 10,000 sheets | 30,000 sheets | 10,000 sheets | Developing sleeve | conductor drum | Surface properties | Toner fixation |
| Example 23 | 1 | A | A | A | A | A | A | A | A | A |
| Comparative Example 1 | 2 | A | A | A | B | B | A | B | A | B |

TABLE 23-continued

|  | Toner | Print out image evaluation | | | | | Matching evaluation for each unit | | | |
|---|---|---|---|---|---|---|---|---|---|---|
|  |  | Image concentration transition during endurance | | | | Image fog | Developing sleeve | Photo-conductor drum | Fixing unit | |
|  |  | Initial stage | 1,000 sheets | 10,000 sheets | 30,000 sheets | 10,000 sheets |  |  | Surface properties | Toner fixation |
| Comparative Example 2 | 3 | A | A | A | A | A | A | A | A | A |
| Comparative Example 3 | 4 | A | A | B | C | C | A | B | A | B |

Good results in all criteria were obtained for toners of Example 23 and Comparative Example 2 wherein microencapsulation of pigments were sufficiently conducted. As a result, Example 23 shows that a toner of excellent image forming ability was effectively produced with a small amount of an enzyme.

Example 24

Production and Evaluation of Color Filters

Copper phthalocyanine was dispersed by a sand mill so that its size was about 0.1 µm. To 1 part by mass of this material was added 39 parts by mass of PBS buffer containing 0.1% Tween-20 and the resulting solution was suspended. This suspension (10 mL) was placed in a centrifuge tube made of Teflon and to this was added 4U equivalence of the PHA synthase aa25-Yn2-C1(pht) prepared in Example 16 and then the resulting solution was stirred for 30 minutes at room temperature to cause the PHA synthase to be absorbed on a pigment surface. This was centrifuged (98,000 m/s2 (10,000 G), 4° C., 10 minutes) and the precipitate was suspended in the PBS solution and then the suspension was again centrifuged (98,000 m/s2 (10,000 G), 4° C., 10 minutes) to immobilize the PHA synthase on copper phthalocyanine.

The aforementioned immobilized enzyme was suspended in 48 parts by mass of 0.1 M phosphoric acid buffer (pH 7.0) and to this suspension were added 1 part by mass of (R)-3-hydroxypimelyl CoA (prepared according to the method described in Eur. J. Biochem., 250, 432–439, 1997) and 0.1 part by mass of bovine serum albumin (Sigma Chemical Corp.), and then the resulting solution was gently shook at 30° C. for 2 hours. The formed microencapsulated pigment was recovered by centrifugation (10,000×g, 4° C., 10 minutes). To 4 parts by mass of this microencapsulated pigment were added 10 parts by mass of ethylene glycol, 15 parts by mass of diethylene glycol, 0.6 part by mass of the monoethanol amine salt of styrene/maleic acid resin (mean molecular weight 30,000, acid value 300), and 70.4 parts by mass of ion exchanged water, and then the solution was stirred with a stirring blade (80 rpm) and dispersed to give Colored Composition (1).

In addition, the PHA monomer unit of the previously recovered microencapsulated pigment was identified as in Example 23. The PHA was confirmed to be a PHA comprised of 3-hydroxypimelic acid.

Furthermore, the molecular weight of the PHA was determined as in Example 23 by gel permeation chromatography to give Mn=47,000.

Next, a blue ink dot was formed on a glass plate by an ink jet recording apparatus using colored composition (1). Moreover, the dot was dried at 80° C. for 20 minutes and further at 180° C. for 1 hour to form a colored layer. The thickness of the colored layer thus obtained was 0.4 µm. Next, a thermoset (High Coat LC-2001, Sanyo Chemical Industries Co., Ltd.) as a transparent protecting film was coated on this pigment particulate layer using a spinner so that the thickness of the dried film was 0.5 µm. After pre-baking at 120° C. for 30 minutes, the film was baked at 200° C. for 30 minutes to form a protecting film, resulting in Color Filter (1) of the present invention.

Comparative Example 4

Cyan Toner (2) was obtained in the same method as in Example 24 with the exception that YN2-C1 was used instead of the PHA synthase aa25-YN2-C1(pht). Further, Two-Component Cyan Developing Agent (2) was obtained using this toner as with Example 24. The properties of this toner were evaluated as in the case of Example 24.

Comparative Example 5

Cyan Toner (3) was obtained in the same method as in Example 24 with the exception that 10U equivalence of YN2-C1 was used instead of 4U equivalence of the PHA synthase aa25-YN2-C1(pht). Further, Two-Component Cyan Developing Agent (3) was obtained using this toner as with Example 24. The properties of this toner were evaluated as in the case of Example 24.

Comparative Example 6

Cyan Toner (4) was obtained as a comparison in the same method as in Example 24 with the exception that 4 parts by mass of copper phthalocyanine was used instead of Colored Composition (1). Further, Two-Component Cyan Developing Agent (4) was obtained using this toner as with Example 24. The properties of this toner were evaluated as in the case of Example 24.

<Evaluation 2>

The volume mean particle sizes and the volume mean particle sizes after stored at room temperature for 30 days, of the microencapsulated pigments of colored compositions in Example 24 and Comparative Examples 4 to 6 were determined by a laser Doppler mode particle size distribution measuring apparatus (UPA-150, Nikkiso Co., Ltd.). The results are shown in Table 24.

Here, the particle size of the pigment prior to microencapsulation was 0.102 µm.

TABLE 24

| Colored Composition | Volume mean particle size/$\mu$m (before storage) | Volume mean particle size/$\mu$m (after storage) |
|---|---|---|
| Example 24 | 1 | 0.124 | 0.132 |
| Comparative Example 4 | 2 | 0.108 | 0.359 |
| Comparative Example 5 | 3 | 0.129 | 0.141 |
| Comparative Example 6 | 4 | 0.102 | 0.458 |

The sizes of pigments before and after microencapsulation (prior to storage) show that the microencapsulation of the pigment in Comparative Example 4 is not sufficient as compared with that in Comparative Example 5. This seems to be because the amount of enzyme added to the pigment in Comparative Example 4 was smaller than the case of Comparative Example 5. On the other hand, the amount of enzyme added in Example 24 was the same as that in Comparative Example 4; however, the microencapsulation is almost equivalent to that of Comparative Example 5.

The volume mean particle sizes of microencapsulation pigments in Example 24 and Comparative Example 5 wherein microencapsulation was sufficiently carried out indicate almost equivalent values before and after storage, showing excellent storage stability.

As a consequence, Example 24 can microencapsulate a pigment by means of a small amount of an enzyme, indicating that it can effectively prevent the coagulation of pigments.

Next, Color Filters (1), (2), (3) and (4) were evaluated in the following ways and the results were summarized in Table 25.

(1) Coagulation Nonuniformity

The image of a color filter produced was observed by a phase contract microscope using transmitted light.

(2) Adhesion of the Colored Layer to the Board

A color filter produced was evaluated by the pressure cooker test at 125° C. at 85% for 6 hours.

(3) Transparency

The transparency of a color filter was evaluated by measuring the transmittance. It was measured using a wavelength at which the maximum transmittance is obtained in the range of 400 nm to 700 nm. In addition, measurements were conducted at 10 sites for a picture element and were averaged.

Also, at the same time, sensuous evaluations were performed visually.

(4) Coloring

The coloring of a color filter produced was visually evaluated based on sensuous evaluation.

(5) Contrast (Depolarization Properties)

Two polarizing plates were disposed facing to each other so as to be able to change optic axes thereof and a color filter was placed touched to the polarizing plates between the polarizing plates. In this state, the color filter was irradiated with back light using a backlight for a liquid crystalline panel (Trade Mark: SLC3LC1EX4UA, Toshiba Lighting & Technology Corp.) to change the optic axes of the two polarizing plates. The brightnesses of natural light when the optic axes lie at right angles and when they are parallel were measured by a brightness meter ("Topcon" BM-5A). The ratio of these brightnesses were calculated as depolarization properties.

Additionally, simultaneously, sensuous evaluations were performed visually.

TABLE 25

| | Color filter | Coagulation non-uniformity | Adhesion | Transparency | Coloring | Contrast |
|---|---|---|---|---|---|---|
| Example 24 | 1 | None | No problem | 84 Good | Good | 1014 Good |
| Comparative Example 4 | 2 | Slightly present | No problem | 76 Slightly inferior | Slightly inferior | 943 Slightly inferior |
| Comparative Example 5 | 3 | None | No problem | 85 Good | Good | 1017 Good |
| Comparative Example 6 | 4 | Slightly present | No problem | 71 Slightly inferior | Slightly inferior | 904 Slightly inferior |

Color filters in Example 24 and Comparative Example 5 wherein microencapsulation of pigments was sufficiently carried out do not exhibit coagulation nonuniformity and have excellent properties such as in adhesion, transparency, coloring and contrast.

As a result, Example 24 shows that a color filter of excellent properties can be effectively produced by means of a small amount of an enzyme.

Example 25

Production and Evaluation of Electrophoretic Particles

To 20 mM phosphoric acid buffer (pH 7.0) containing 1% by mass of a surfactant of Tween-20 was suspended a pigment of Carbon Black at a concentration of 25% by mass. This solution was mixed by a ball mill to prepare a dispersion of Carbon Black. The dispersion was found to be a single dispersed state with a particle size of 1.2 $\mu$m using the laser scattering method.

Then, to the dispersion was added the PHA synthase aa39-YN2-C1(cb) prepared in Example 20 so that the concentration of the enzyme was 40U/mL, and the resulting mixture was allowed to stand at 20° C. for 30 minutes. Thereafter, to the resultant was added (R)-3-hydroxyoctanoyl CoA prepared in Reference Example 2 so that the final concentration of the coenzyme was 5 mM. The synthesis reaction was conducted by incubation at 37° C. for 30 minutes.

The reaction system was centrifuged (10,000×g, 4° C., 10 minutes) to yield a water-containing cake of electrophoretic particles wherein Carbon Black was microencapsulated. The water-containing cake was re-suspended in ethanol and then electrophoretic particles were recovered by another centrifugation operation. This operation was repeated three times to perform dehydration. Then, the electrophoretic particle was suspended using kerosene and the dispersing medium was replaced with the kerosene by repeating centrifugation and washing to give Electrophoresis Display Dispersion System (1).

The aforementioned electrophoretic particle was vacuum dried and the resulting substance was suspended in 20 mL of chloroform and then the suspension was stirred at 60° C. for 20 hours to extract a PHA comprised in an outer shell. The extract was subjected to filtration using a membrane filter with a pore diameter of 0.45 $\mu$m, vacuum concentration by a rotary evaporator, methanolysis by a normal method, analysis by a gas chromatography/mass analysis apparatus (GC-MS, Shimadzu QP-5050, EI mode) and subsequent identification of a methylesterified compound of a PHA monomer unit. As a result, the PHA was confirmed to be a PHA having 3-hydroxyoctanoic acid as the monomer unit, as indicated in FIGS. 3A and 3B. Further, the molecular weight of the PHA was determined by gel permeation chromatography (GPC: Toso HLC-8020, column: Polymer Laboratory PL gel MIXED-C(5 $\mu$m), solvent: chloroform, column temperature: 40° C., in terms of polystyrene) to give Mn=22,000, Mw=42,000.

Comparative Example 7

Electrophoretic Particle (2) was obtained in the same method as in Example 25 with the exception that YN2-C1 was used instead of the PHA synthase aa39-YN2-C1(cb). Further, Electrophoresis Display Dispersion System (2) was obtained using this particle as with Example 25.

Comparative Example 8

Electrophoretic Particle (3) was obtained in the same method as in Example 25 with the exception that 100U equivalent of YN2-C1 was used instead of 40U equivalent of the PHA synthase aa39-YN2-C1(cb). Further, Electrophoresis Display Dispersion System (3) was obtained using this particle as with Example 25.

Comparative Example 9

Carbon Black (25 g) was added to 75 g of heat-fused polyethylene resin and then uniformly dispersed using a roll mill. The mixture was then hardened by cooling and was finely comminuted to yield Electrophoretic Particle (4). Electrophoresis Display Dispersion System (4) was obtained using this particle as with Example 25.

<Evaluation 3>

The dispersability of an electrophoretic particle for an insulating medium was evaluated.

To 3 g of a specimen of an electrophoretic particle placed in a test tube were added 50 mL of a dispersing medium (kerosene) and, as required, 0.6 g of a surfactant (polycarboxylic acid derivative) and the resulting mixture was stirred with a magnetic stirrer for 2 hours. The supernatant (1.0 mL) was immediately taken out and weighed after complete removal of the dispersing medium by heating it an oven. Here, the weight was denoted by Wo (g). In addition, the aforementioned mixture was allowed to stand for a predetermined time, and then 1.0 mL of the supernatant was similarly taken out of the test tube and thereafter the weight was measured after complete removal of the dispersing medium by heating it an oven. The weight was denoted by Wi (g). Then, dispersion stability S was calculated based on the following equation.

$$\text{Dispersion stability } S \ (\%) = Wi \ (g)/Wo \ (g) \times 100 \quad \text{(Equation 1)}$$

The results of dispersion stabilities S and particle sizes by the laser scattering method, of electrophoretic particles, are given in Table 26.

TABLE 26

| | Electrophoretic particle | Particle size ($\mu$m) | Dispersion stability (20 minutes later) |
|---|---|---|---|
| Example 25 | 1 | 1.6 | 97% |
| Comparative Example 7 | 2 | 1.3 | 24% |
| Comparative Example 8 | 3 | 1.7 | 97% |
| Comparative Example 9 | 4 | 1.2 | 2% |

The sizes of pigments before and after microencapsulation show that the microencapsulation of the pigment in Comparative Example 7 is not sufficient as compared with that in Comparative Example 8. This seems to be because the amount of enzyme added to the pigment in Comparative Example 7 was smaller than the case of Comparative Example 8. On the other hand, the amount of enzyme added in Example 25 was the same as that in Comparative Example 7; however, the microencapsulation is almost equivalent to that of Comparative Example 8.

Dispersion stability of electrophoretic particles in a dispersing medium in Example 25 and Comparative Example 8 wherein microencapsulation was sufficiently carried out is excellent.

As a consequence, Example 25 can microencapsulate a pigment by means of a small amount of an enzyme, indicating that it can effectively improve the dispersion stability when the pigment is made to be an electrophoretic particle.

Next, the movement of each electrophoretic particle was confirmed.

An ITO electrode was film-formed on a first light-transmittable board made of the PES film of 150 $\mu$m in thickness and patterning was conducted for the board in a line-like form by photolithography and wet etching. A resin layer containing a titanium oxide fine particle whitened by irregular reflection of light was made to form on this board as an insulating layer. Further, titanium carbide was film-formed on it as a second electrode and it was made in a line-like form by photolithography and wet etching. Furthermore, the first electrode alone was etched and holed in a circular form. A highly transparent polyimide layer was also formed on the second electrode. Then, a heat sealing adhesion layer was formed in a pattern at the junction of the second board.

The second light-transmittable board made of the PES film was formed in a concave form by thermal press molding, and at the adhesion portion to the first board was formed a heat sealing adhesion layer as with the first board.

In the concave of this second board, a transparent insulation liquid and Electrophoretic Particles (1), (2), (3) and (4) prepared in Example 25 and Comparative Examples 7 to 9 each were separately loaded. Diiodine methane with a refractive index larger than that of the PES film of the second board material was used as an insulating medium.

After loading, the positions of the adhesion layers of the first and the second boards were piled up and heat sealed.

This was provided with a voltage application circuit to give a display apparatus.

Thereafter, a display was performed using the display apparatus thus made. The application voltage was set to be ±50 V.

When a voltage was applied such that the first electrode became an anode and the second electrode a cathode, Electrophoretic Particles (1) and (3), wherein microencapsulation of the pigments was sufficiently carried out, moved onto the second electrode located on the periphery of the bottom surface of the second board of a concave structure. When this was observed from the second board side, because the concave structure of the second board acted as a lens, and so light was collected at the central part of the first board and then entered into the exposed, whitened insulating layer to make the whole lens look white. In addition, when a voltage was applied so that the polarity was inverted and thus the first electrode was a cathode and the second an anode, the electrophoretic particle was collected at the central part, which caused the whole lens to appear black of the electrophoretic particle. At this time, the response rate was 20 msec or less, and thus yielded a display apparatus capable of displaying two colors.

On the other hand, for Electrophoretic Particles (2) and (4), wherein the microencapsulation of the pigments was not sufficiently carried out, the movement by voltage application was nonuniform, and thus did not cause the whole lens to look white or black.

Example 26

Production and Evaluation of Pigment Ink

To 20 mM phosphoric acid buffer (pH 7.0) containing 1% by mass of a surfactant of Tween-20 was suspended a pigment of Carbon Black at a concentration of 25% by mass. This solution was mixed by a ball mill to prepare a dispersion of Carbon Black. The dispersion was found to be a single dispersed state with a particle size of 102 nm using the laser scattering method.

Then, to the dispersion was added the PHA synthase aa40-YN2-C1(cb) prepared in Example 20 so that the concentration of the enzyme was 40U/mL, and the resulting mixture was allowed to stand at 20° C. for 30 minutes. Thereafter, to the resultant was added (R)-3-hydroxyoctanoyl CoA prepared in Reference Example 2 so that the final concentration of the coenzyme was 5 mM. The synthesis reaction was conducted by incubation at 37° C. for 30 minutes.

The reaction system was centrifuged (10,000×g, 4° C., 10 minutes) to yield a water-containing cake of a microencapsulated pigment having Carbon Black as the core. The water-containing cake was re-suspended in water and then Microencapsulated Pigment (1) were recovered by another centrifugation operation. This operation was repeated three times for cleaning.

A part of the water-containing cake of the prepared microencapsulated pigment was vacuum dried and the resulting substance was suspended in 20 mL of chloroform and then the suspension was stirred at 60° C. for 20 hours to extract a PHA comprised in an outer shell. The extract was subjected to filtration using a membrane filter with a pore diameter of 0.45 μm, vacuum concentration by a rotary evaporator, methanolysis by a normal method, analysis by a gas chromatography/mass analysis apparatus (GC-MS, Shimadzu QP-5050, EI mode) and subsequent identification of a methylesterified compound of a PHA monomer unit. As a result, the PHA was confirmed to be a PHA having 3-hydroxyoctanoic acid as the monomer unit. Further, the molecular weight of the PHA was determined by gel permeation chromatography (GPC: Toso HLC-8020, column: Polymer Laboratory PL gel MIXED-C (5 μm), solvent: chloroform, column temperature: 40° C., in terms of polystyrene) to give Mn=18,000, Mw=37,000.

Aqueous black ink was prepared using the aforementioned Microencapsulated Pigment (1). The composition of the black ink is shown below. The amount of each component is represented as parts by mass. A dispersion stirrer (TK Homodyspa 20 type Tokushu Kika Kogyo Co., Ltd.) was used and the dispersion time was 3 hours.

| | |
|---|---|
| Microencapsulated pigment | 50 parts |
| Glycerin | 6 parts |
| Diethylene glycol | 7 parts |
| Polyoxyethylene dodecyl ether | 0.2 parts |
| Proxel XL-2: preservative (ZENECA Corp.) | 0.3 parts |
| Benzotriazole: corrosion inhibitor (Kanto Kagaku Co., Ltd.) | 0.005 parts |
| Water | the balance |

Comparative Example 10

Microencapsulated Pigment (2) was obtained in the same method as in Example 26 with the exception that YN2-C1 was used instead of the PHA synthase aa40-YN2-C1(cb). Further, Aqueous Pigment Ink (2) was obtained using this particle as with Example 26.

Comparative Example 11

Microencapsulated Pigment (3) was obtained in the same method as in Example 26 with the exception that 100U equivalent of YN2-C1 was used instead of 40U equivalent of the PHA synthase aa39-YN2-C1(cb). Further, Aqueous Pigment Ink (3) was obtained using this pigment as with Example 26.

Comparative Example 12

Aqueous Pigment Ink (4) was prepared as in the same method as in Example 26 except that a finely pulverized Carbon Black was used instead of a microencapsulated pigment.

<Evaluation 4>

Dispersion stability and mean particle sizes were evaluated for Aqueous Pigment Ink (1), (2), (3) and (4) prepared as discussed earlier. Dispersion stability was expressed as the ratio of the translucent upper layer generated by precipitation of the pigment component to the height of the total dispersion liquid based on the extent of phase separation as a measure after storage at 70° C. for 3 days. The mean particle size was defined as the median diameter measured with a laser Doppler type particle size distribution analyzer, Microtrak (UPA 150 type, Lease & Nothropp). The results are given in Table 27.

TABLE 27

| | | Mean particle size (nm) | | |
|---|---|---|---|---|
| Aqueous pigment ink | | Immediately after preparation | 70° C.; 3 days later | Phase separation |
| Example 26 | 1 | 181 | 192 | 0 |
| Comparative Example 10 | 2 | 163 | 752 | 11 |
| Comparative Example 11 | 3 | 183 | 194 | 0 |
| Comparative Example 12 | 4 | 151 | 2358 | 28 |

The sizes of pigments before and after microencapsulation show that the microencapsulation of the pigment in Comparative Example 10 is not sufficient as compared with that in Comparative Example 11. This seems to be because the amount of enzyme added to the pigment in Comparative Example 10 was smaller than the case of Comparative Example 11. On the other hand, the amount of enzyme added in Example 26 was the same as that in Comparative Example 10; however, the microencapsulation is almost equivalent to that of Comparative Example 11.

Dispersion stability of aqueous pigment ink in Example 26 and Comparative Example 11 wherein microencapsulation was sufficiently carried out is excellent.

As a consequence, Example 26 can microencapsulate a pigment by means of a small amount of an enzyme, indicating that it can effectively improve the dispersion stability when the pigment is made to be aqueous pigment ink.

Next, the ink was evaluated as ink for an ink jet printer.

Printing was conducted using the Aqueous Pigment Ink (1), (2), (3) and (4) described above by means of an ink jet printer provided with a recording head with a 360 dpi resolution at a discharge frequency of 7.2 kHz at an interval of 720 dpi in the main scanning direction. The amount of discharge per droplet of ink out of the recording head was taken as about 25 picolitters and a record was performed by injecting a drop of ink into one picture element formed by a resolution of 360 dpi×720 dpi. Then, the OD, peripheral shape of dot, solid shade uniformity, strike through, smoothing, and roundness of images were evaluated by printing solid shaded images and character patterns, etc. In addition, a PB sheet made by Canon Inc. was used as a print medium. In this case, OD refers to the value obtained by measuring the part of a solid shaded pattern of 5 mm×5 mm.

A dot peripheral shape was checked by visually observing the sharpness of the edge part of a line image using a loupe.

A: The line edge is clearly connected in a straight line form.
B: The linearity of the line edge is slightly lost, but it practically presents no problems.
D: The linearity of the line edge is lost.

The solid shade uniformity was inspected by visually observing the uniformity of the concentration on a solid shade pattern of 5 mm×5 mm.

A: Whitely spotted parts are not observed.
B: Whitely spotted parts are observed, but inconspicuous and practically no problems.
D: Whitely spotted parts are conspicuous and affect the quality of the image.

Strike through was checked by observing whether or not a pattern of the part on which a solid shade pattern had been printed can be seen through the sheet by the observation from the back. Also, the optical concentration of the corresponding part of the back was measured with a Macbeth reflectometer.

A: Cannot almost see through, and the optical concentration by the Macbeth reflectometer is less than 0.2.
B: Can slightly see through, but not be recognizable. The optical concentration by the Macbeth reflectometer is 0.2 or more and less than 0.25.

Roundness was determined by observing with a loupe the shape of an ink dot formed on the print medium by a drop of ink.

A: Almost all the dots are near round from the viewpoint of statistics.
B: Dots are not round from the viewpoint of statistics, but it does not cause problems for image formation.
C: A relatively large number of dots are not round from the viewpoint of statistics, and distorted dots are formed.

The results are shown in Table 28 below.

TABLE 28

|  | Aqueous pigment ink | OD | Dot size ($\mu$m) | Shape around dot | Solid shade uniformity | Strike through | Roundness |
|---|---|---|---|---|---|---|---|
| Example 26 | 1 | 1.46 | 69 | A | A | A | A |
| Comparative Example 10 | 2 | 1.32 | 51 | B | B | B | B |
| Comparative Example 11 | 3 | 1.48 | 70 | A | A | A | A |
| Comparative Example 12 | 4 | 1.08 | 45 | D | D | B | C |

For ink prepared in Example 24 and Comparative Example 5 wherein microencapsulation of pigments is sufficiently conducted, when used in ink for an ink jet printer, coagulations of the pigment on a recording medium (paper) become finely granular to uniformly disperse in ink dots, and have a dot size of an appropriate spread, and also the image concentration distribution within dots is uniform and the ink dots are excellent in peripheral and outer shapes almost without feathering, or the like.

As a result, Example 26 is shown to be able to effectively produce aqueous pigment ink having excellent properties by means of a small amount of an enzyme.

Example 27

Acquisition of an Amino Acid Sequence Capable of Binding to Titanium Oxide (1) Titanium oxide (Wako Pure Chemical Industries Co., Ltd., titanium oxide (IV), rutile type) was suspended in a TBS buffer (50 mM tris-HCl pH 7.5, 150 mM NaCl) containing 0.1% Tween-20 so that the concentration was 5 mg/mL. This solution (10 $\mu$L) was put in an Eppeldorf tube and was diluted with 990 $\mu$L of a TBST buffer (TBS buffer+0.1% Tween-20).

(2) In a tube was put $4 \times 10^{10}$ pfu equivalent of Ph.D.-12 phage display peptide library (New England BioLabs) and allowed to stand at 25° C. for 10 minutes.

(3) After centrifugation of the tube (20,630×g, 5 minutes), the supernatant was decanted and the pigment was recovered as a precipitate. The recovered pigment was again suspended in a TBST buffer and the suspension was centrifuged. This operation was repeated 10 times to clean the pigment with the TBST buffer.

(4) To the resulting pigment was added 100 $\mu$L of elution buffer (0.2 M Glycine-HCl (pH 2.2), 1 mg/mL BSA) and the solution was allowed to stand for 1 minute, centrifuged (20,630×g, 5 minutes), and then the supernatant was transferred to another Eppendorf tube. To this liquid was added 15 μL of 1M Tris-HCl (pH 9.1) for neutralization and an eluted phage was obtained.

(5) The eluted phage was incorporated into *Escherichia coli* ER2537 (New England BioLabs) at the early stage of logarithmic growth and amplified. It was cultured at 37° C. for 4.5 hours. Then, the phage was separated from the cell by centrifugation and was purified by polyethylene glycol precipitation. The purified, amplified phage was suspended in a TBS buffer and the titer was determined by making an appropriate dilute line infect *Escherichia coli*.

(6) The aforementioned operations from (1) to (5) were repeated another 4 times using the amplified phage. Note that the conditions of cleaning was made severe by increasing to 0.5% the concentration of Tween-20 in a TBST buffer used. From the second time on, similar operations were conducted for the Eppendorf tube sample to give the control. The titers of phages eluted at each cycle are indicated in Table 29.

TABLE 29

Titers of phages eluted in each cycle

| | Stock solution (A) | Control bond (B) | Titanium oxide binding (C) | C/A | C/B |
|---|---|---|---|---|---|
| First time | $4.0 \times 10^{11}$ | | $8.9 \times 10^{6}$ | $2.2 \times 10^{-5}$ | |
| Second time | $1.6 \times 10^{11}$ | $1.1 \times 10^{5}$ | $3.8 \times 10^{6}$ | $2.4 \times 10^{-5}$ | 35 |
| Third time | $2.0 \times 10^{11}$ | $1.6 \times 10^{5}$ | $6.0 \times 10^{6}$ | $3.0 \times 10^{-5}$ | 40 |
| Fourth time | $1.7 \times 10^{11}$ | $1.1 \times 10^{6}$ | $1.5 \times 10^{8}$ | $8.8 \times 10^{-4}$ | 140 |
| Fifth time | $1.9 \times 10^{11}$ | $2.0 \times 10^{6}$ | $2.7 \times 10^{9}$ | $1.4 \times 10^{-2}$ | 1400 |

(Unit of A, B, and C is represented by pfu/ml)

The finally eluted phage was cloned by making it infect a large excess amount of *Escherichia coli*. After *Escherichia coli* was infected with each clone for amplification, ssDNA was prepared. An amino acid sequence capable of binding to titanium oxide was obtained by decoding the base sequence of a random domain. Amino acid sequences and frequencies thus obtained are shown in Table 30.

Example 28

A PHA synthase capable of binding to titanium oxide was prepared as follows. An *Escherichia coli* expression vector expressing each amino acid sequence (SEQ ID NO:150 to SEQ ID NO:157) through the spacer sequence GS by fusing to the N terminal of a PHA synthase was prepared in the following. A set of synthesized oligonucleotides as given in Table 31 was arranged for production of the DNA coding these amino acid sequences as a double-stranded DNA.

TABLE 30

Determined amino acid sequence and frequency

| Determined amino acid sequence | | Number (A) | Frequency (A/29) |
|---|---|---|---|
| His-Ala-Thr-Gly-Thr-His-Gly-Leu-Ser-Leu-Ser-His | (SEQ ID NO:150) | 13 | 0.45 |
| Thr-Leu-Pro-Ser-Pro-Leu-Ala-Leu-Leu-Thr-Val-His | (SEQ ID NO:151) | 7 | 0.24 |
| Leu-Ser-Thr-His-Tyr-Val-Asn-Arg-Ser-His-Ile-Thr | (SEQ ID NO:152) | 4 | 0.14 |
| Ala-Tyr-His-Ile-Asn-Gln-Leu-Gly-Ala-Pro-Pro-Ala | (SEQ ID NO:153) | 1 | 0.03 |
| Leu-His-Leu-Thr-Pro-His-Pro-Gly-Asp-Thr-Leu-Thr | (SEQ ID NO:154) | 1 | 0.03 |
| Gln-Asp-Val-His-Leu-Thr-Gln-Gln-Ser-Arg-Tyr-Thr | (SEQ ID NO:155) | 1 | 0.03 |
| Leu-Glu-Ile-Pro-Ser-Asn-Gly-Leu-Asn-His-Lys-Ile | (SEQ ID NO:156) | 1 | 0.03 |
| Leu-Glu-Ile-Pro-Ser-Asn-Gly-Leu-Asn-His-Asn-Ile | (SEQ ID NO:157) | 1 | 0.03 |

TABLE 31

Synthesized DNA set for expressing each amino acid sequence

| SEQ ID NO: amino acid sequence | SEQ ID NO: Base sequence of synthesized DNA | |
|---|---|---|
| SEQ ID NO:150 | 5'-GATCCCATGCGACCGGCACCCATGGCCTGAGCCTGAGCCATGAGCT-3' | SEQ ID NO:158 |
| HATGTHGLSLSH | 5'-CATGGCTCAGGCTCAGGCCATGGGTGCCGGTCGCATGG-3' | SEQ ID NO:159 |
| SEQ ID NO:151 | 5'-GATCCACCCTGCCGAGCCCGCTGGCGCTGCTGACCGTGCATGAGCT-3' | SEQ ID NO:160 |
| TLPSPLALLTVH | 5'-CATGCACGGTCAGCAGCGCCAGCGGGCTCGGCAGGGTG-3' | SEQ ID NO:161 |
| SEQ ID NO:152 | 5'-GATCCCTGAGCACCCATTATGTGAACCGTAGCCATATTACCGAGCT-3' | SEQ ID NO:162 |
| LSTHYVNRSHIT | 5'-CGGTAATATGGCTACGGTTCACATAATGGGTGCTCAGG-3' | SEQ ID NO:163 |
| SEQ ID NO:153 | 5'-GATCCGCGTATCATATTAACCAGCTGGGCGCGCCGCCGGCGGAGCT-3' | SEQ ID NO:164 |
| AYHINQLGAPPA | 5'-CCGCCGGCGGCGCGCCCAGCTGGTTAATATGATACGCG-3' | SEQ ID NO:165 |
| SEQ ID NO:154 | 5'-GATCCCTGCATCTGACCCCGCATCCGGGCGATACCCTGACCGAGCT-3' | SEQ ID NO:166 |
| LHLTPHPGDTLT | 5'-CGGTCAGGGTATCGCCCGGATGCGGGGTCAGATGCAGG-3' | SEQ ID NO:167 |
| SEQ ID NO:155 | 5'-GATCCCAGGATGTGCATCTGACCCAGCAGAGCCGTTATACCGAGCT-3' | SEQ ID NO:168 |
| QDVHLTQQSRYT | 5'-CGGTATAACGGCTCTGCTGGGTCAGATGCACATCCTGG-3' | SEQ ID NO:169 |
| SEQ ID NO:156 | 5'-GATCCCTGGAAATTCCGAGCAACGGCCTGAACCATAAAATTGAGCT-3' | SEQ ID NO:170 |
| LEIPSNGLNHKI | 5'-CAATTTTATGGTTCAGGCCGTTGCTCGGAATTTCCAGG-3' | SEQ ID NO:171 |
| SEQ ID NO:157 | 5'-GATCCCTGGAAATTCCGAGCAACGGCCTGAACCATAACATTGAGCT-3' | SEQ ID NO:172 |
| LEIPSNGLNHNI | 5'-CAATGTTATGGTTCAGGCCGTTGCTCGGAATTTCCAGG-3' | SEQ ID NO:173 |

Two kinds of synthesized DNAs for each amino acid sequence given in Table 31 were phosphorylated using T4 polynucleotide kinase (Gibco) according to the manufacturer's explanations. Then, equi-molar amounts of two kinds of the synthetic DNA were mixed and the mixture was heated at 95° C. for 5 minutes, and then it was slowly cooled to room temperature to thereby form a double-stranded DNA fragment. The formed double-stranded DNA fragment was then directly used for cloning.

The plasmid pGEX-C1 was digested by BamHI and SacI, and then the aforementioned double-stranded DNA fragment was inserted. An *Escherichia coli* (JM109) was transformed using this vector to yield a strain for expression. Confirmation of the strain was performed by determining the inserted base sequence by sequencing using pGEX5' Sequencing Primer (Amasham Pharmasia Biotech Corp.) with a plasmid DNA prepared using Miniprep (Wizard Minipreps DNA Purification Systems, PROMEGA Corp.) as a template. After the obtained strain was pre-cultured in 10 mL of an LB-Amp culture medium, 0.1 mL of the resultant containing the strain was added to 10 mL of an LB-Amp culture medium and the mixture was cultured with an agitation of 170 rpm at 37° C. for 3 hours. Thereafter, IPTG was added to it (final concentration 1 mM) and the culture was continued at 37° C. for 4 to 12 hours.

IPTG-induced *Escherichia coli* was collected (8000×g, 2 minutes, 4° C.), and it was re-suspended in 4° C. PBS of ¹⁄₁₀ of the amount of the microbe. The strain was destroyed by freezing and thawing and sonication, and the cell debris were removed by centrifugation (8000×g, 10 minutes, 4° C.). After the target expression protein was confirmed to be in the supernatant by SDS-PAGE, the derived, expressed GST-fused protein was purified with Glutathion Sepharose 4B beads (Amasham Pharmasia Biotech Corp.).

The glutathion sepharose used was subjected to pre-treatment of suppressing non-specific adsorption. In other words, after the glutathion sepharose was cleaned 3 times with an equivalent amount of PBS (8000×g, 1 minute, 4° C.), to this was added an equivalent amount of 4% BSA-containing PBS and the material was treated at 4° C. for 1 hour. After the treatment, it was cleaned 2 times with an equivalent amount of PBS, and then was re-suspended in PBS of ½ of the amount. To 1 mL of a cell free extract was added 40 μL of the pre-treated glutathion sepharose and the solution was gently stirred at 4° C. In this manner, the fused proteins GST-aa150-YN2-C1 to GST-aa157-YN2-C1 were adsorbed on the glutathion sepharose. [In the fused protein GST-aa##-YN2-C1, aa## refers to expression expressed by fusing the polypeptide composed of the amino acid sequence of the SEQ ID NO:## between a PHA synthase and GST.]

After the adsorption, the glutathion sepharose was retrieved by centrifugation (8000×g, 1 minute, 4° C.) and the resultant material was cleaned 3 times with 400 μL of PBS. Thereafter, to this was added 40 μL of 10 mM reduced glutathion and the solution was agitated at 4° C. for 1 hour to elute the adsorbed fused protein. The resulting solution was centrifuged (8000×g, 2 minutes, 4° C.) and then the supernatant was recovered. Dialysis was conducted with respect to PBS to purify the GST fused protein. The protein was confirmed to show a single band by SDS-PAGE.

Each GST fused protein (500 μg) was digested by a PreScission protease (Amasham Pharmasia Biotech Corp., 5U), and then the protease and GST were removed by passing them through glutathion sepharose. The flow-through fraction was further passed through a sephadex G200 column equilibrated with PBS to give the final purified product of each expressed protein aa150-YN2-C1(ti) to aa157-YN2-C1(ti). [In the expressed protein aa##-YN2-C1 (ti), aa## refers to expression expressed by fusing the polypeptide composed of the amino acid sequence of the SEQ ID NO:## in the N terminal of a PHA synthase.]

The activity of each purified enzyme was measured by the aforementioned method. In addition, the protein concentration in the sample was determined by a micro BCA protein determining reagent kit (Pierce Chemical Corp.). The enzyme concentration was 1.9 U/mL and the relative activity was 4.0 U/mg protein. The purified enzyme was concentrated using a bio-solution sample concentrating agent (Mizubutori Kun AB-1100, Ato Co., Ltd.) to yield a purified enzyme solution of 10 U/mL.

Example 29

Evaluation of the Capability of Binding to Titanium Oxide

Titanium oxide was suspended in a TBS buffer containing 0.1% Tween-20 so that the concentration was 0.5% (w/v). To 10 mL of this solution put in a Teflon centrifugation tube, the PHA synthases aa150-YN2-C1(ti) to aa157-YN2-C1(ti) prepared in Example 28 and 0.5U equivalent of YN2-C1 prepared in Reference Example 1 were added, and the resulting solution was agitated at room temperature for 30 minutes. The titanium oxide particle was retrieved as a precipitate by a centrifugation operation (10,000×g, 4° C., 10 minutes) to be separated from the supernatant containing the enzyme having not binding to the titanium oxide. The titanium oxide was again suspended in a TBS buffer containing 0.1% Tween-20 and was washed by repeating centrifugation. The enzyme activity of the suspension of the cleaned titanium oxide was measured. The results are given in Table 32.

Table 32
Evaluation of Binding Affinity of Enzymes to Titanium Oxide

TABLE 32

Evaluation of binding affinity of enzymes to titanium oxide

| Enzyme | Fusion amino acid sequence | Enzyme activity U |
| --- | --- | --- |
| aa150-YN2-C1 (ti) | SEQ ID NO:150 HATGTHGLSLSH | 0.06 |
| aa151-YN2-C1 (ti) | SEQ ID NO:151 TLPSPLALLTVH | 0.06 |
| aa152-YN2-C1 (ti) | SEQ ID NO:152 LSTHYVNRSHIT | 0.05 |
| aa153-YN2-C1 (ti) | SEQ ID NO:153 AYHINQLGAPPA | 0.05 |
| aa154-YN2-C1 (ti) | SEQ ID NO:154 LHLTPHPGDTLT | 0.05 |
| aa155-YN2-C1 (ti) | SEQ ID NO:155 QDVHLTQQSRYT | 0.05 |
| aa156-YN2-C1 (ti) | SEQ ID NO:156 LEIPSNGLNHKI | 0.05 |
| aa157-YN2-C1 (ti) | SEQ ID NO:157 LEIPSNGLNHNI | 0.05 |
| YN2-C1 | — | 0.01 |

It was confirmed that the enzyme aa150-YN2-C1(ti) to aa157-YN2-C1(ti) fused with a titanium oxide affinity sequence had a higher enzyme activity compared with the enzyme YN2-C1 of control, and thus could be effectively immobilized on a base material surface.

Example 30

Two kinds of amino acid sequences capable of binding to titanium oxide, His-Ala-Thr-Gly-Thr-His-Gly-Leu-Ser-Leu-Ser-His (SEQ ID NO:150) and Thr-Leu-Pro-Ser-Pro-Leu-Ala-Leu-Leu-Thr-Val-His (SEQ ID NO:151), were all connected in the indicated order in series through the spacer sequence Gly-Gly-Gly-Ser-Gly-Gly-Gly-Ser (SEQ ID NO:181) to give His-Ala-Thr-Gly-Thr-His-Gly-Leu-Ser-Leu-Ser-His-Gly-Gly-Gly-Ser-Gly-Gly-Gly-Ser-Thr-Leu-Pro-Ser-Pro-Leu-Ala-Leu-Leu-Thr-Val-His (SEQ ID NO:174), which was further fused to the N terminal of a PHA synthase through the use of the spacer sequence GS to prepare an *Escherichia coli* expression vector in the following. The DNA encoding this amino acid sequence was formed as a double-stranded DNA fragment by, after phosphorylating

```
Seq.1:
5'-GATCCCATGCGACCGGCACCCATGGCCTGAGCCTGAGCCATGGCGGCGGCAGCGG  (SEQ ID NO:175)
CGGCGCCAGCACCCTGCCGAGCCCGCTGGCGCTGCTGACCGTGCATGAGCT-3' and Seq. 2:
5'-CATGCACGGTCAGCAGCGCCAGCGGGCTCGGCAGGGTGCTGCCGCCGCCGCTGCC  (SEQ ID NO:176)
GCCGCCATGGCTCAGGCTCAGGCCATGGGTGCCGGTCGCATGG-3'
``` each using T4 polynucleotide kinase (Gibco), mixing the equimoles thereof, heating at 95° C. for 5 minutes, and then slowly cooling to room temperature. The double-stranded DNA fragment thus formed was inserted into the BamHI/SacI site of the plasmid pGEX-C1 as with Example 28, and an *Escherichia coli* (JM109) was transformed using this vector to yield a strain for expression. As with Example 28, the expressed protein aa174-YN2-C1(ti), the amino acid sequence of SEQ ID NO:174 being fused at the N terminal thereof, was purified to give 10 U/mL of a purified enzyme solution. The capability of the purified enzyme binding to titanium oxide was evaluated as in Example 29. The results are shown in Table 33.

TABLE 33

Evaluation of binding affinity enzyme to titanium oxide

| Enzyme | Fusion amino acid sequence | Enzyme activity U |
|---|---|---|
| aa174-YN2-C1 (ti) | SEQ ID NO: 174 HATGTHGLSLSHGGGSGGGSTLPSPLALLTVH | 0.15 |
| YN2-C1 | — | 0.01 |

The enzymes aa174-YN2-C1(ti), in which the titanium oxide affinity sequence was fused, have been confirmed to be higher in enzyme activity and to more effectively immobilize the enzyme on the base material surface than the enzyme YN2-C1, the control.

According to a method for manufacturing polyhydroxyalkanoate-containing structure of the present invention, polyhydroxyalkanoate-synthesizing enzyme containing an amino acid sequence capable of binding to a base material can be effectively immobilized on the base material by selecting amino acid sequences capable of various base materials. Further, the surface of the base material can be effectively coated with a desirable polyhydroxyalkanoate-containing structure by the addition of 3-hydroxyacyl coenzyme A to become the substrate of the enzyme. Polyhydroxyalkanoate-containing structure of the present invention can find a wide variety of applications as a functional structure in that the surface thereof is coated with polyhydroxyalkanoate of diverse properties.

What is claimed is:

1. A method for manufacturing polyhydroxyalkanoate-containing structure, at least a part of a base material surface of the structure being coated with polyhydroxyalkanoate, the method comprising the steps of:

immobilizing a polyhydroxyalkanoate synthase on said base material surface, synthesizing, on said base material surface, polyhydroxyalkanoate using a 3-hydroxyacyl coenzyme A to become the substrate of said synthase and said synthase and coating at least a part of said base material surface with the synthesized polyhydroxyalkanoate, wherein said synthase contains an amino acid sequence capable of binding to said base material.

2. The manufacturing method according to claim 1, wherein the polyhydroxyalkanoate is comprised of at least one selected from the group consisting of monomer units expressed by Formulas [1] to [10], and each corresponding 3-hydroxyacyl coenzyme A is selected from the group consisting of 3-hydroxyacyl coenzymes A expressed by Formulas [12] to [21]:

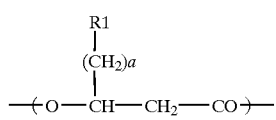
[1]

(wherein symbol "a" represents an integer, and the combination of R1 and "a" is selected from the group consisting of a combination of a hydrogen atom and any one integer selected from the group consisting of 0 to 10;

a combination of a halogen atom and any one integer selected from the group consisting of 1 to 10;

a combination of a chromophoric group and any one integer selected from the group consisting of 1 to 10;

a combination of a carboxyl group or a salt thereof and any one integer selected from the group consisting of 1 to 10; and a combination of

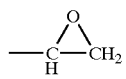

and any one integer selected from the group consisting of 1 to 7),

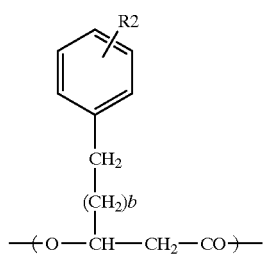
[2]

(wherein b represents any one integer selected from the group consisting of 0 to 7, and R2 is selected from the group consisting of a hydrogen atom (H), a halogen atom, —CN, —NO$_2$, —CF$_3$, —C$_2$F$_5$ and —C$_3$F$_7$),

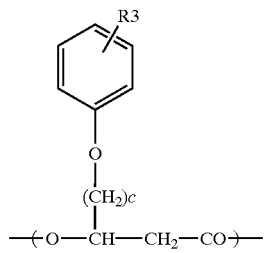
[3]

(wherein c represents any one integer selected from the group consisting of 1 to 8, and R3 is selected from the group consisting of a hydrogen atom (H), a halogen atom, —CN, —NO$_2$, —CF$_3$, —C$_2$F$_5$ and —C$_3$F$_7$),

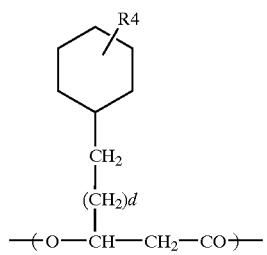
[4]

(wherein d represents any one integer selected from the group consisting of 0 to 7, and R4 is selected from the group consisting of a hydrogen atom (H), a halogen atom, —CN, —NO$_2$, —CF$_3$, —C$_2$F$_5$ and —C$_3$F$_7$),

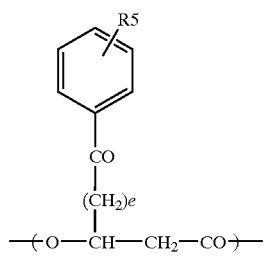
[5]

(wherein e represents any one integer selected from the group consisting of 1 to 8, and R5 is selected from the group consisting of a hydrogen atom (H), a halogen atom, —CN, —NO$_2$, —CF$_3$, —C$_2$F$_5$, C$_3$F$_7$, —CH$_3$, —C$_2$H$_5$ and —C$_3$H$_7$),

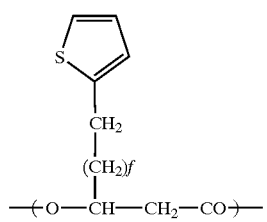
[6]

(wherein f represents any one integer selected from the group consisting of 0 to 7),

[7]

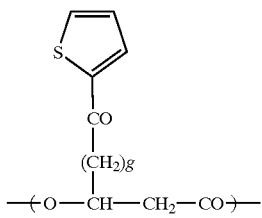

(wherein g represents any one integer selected from the group consisting of 1 to 8),

[8]

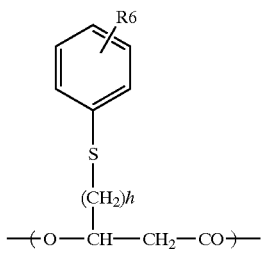

(wherein h represents any one integer selected from the group consisting of 1 to 7, and R6 is selected from the group consisting of a hydrogen atom (H), a halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$, wherein R' is selected from the group consisting of a hydrogen atom (H), Na, K, —CH$_3$ and —C$_2$H$_5$, and R" is selected from the group consisting of —OH, ONa, —OK, a halogen atom, —OCH$_3$ and —OC$_2$H$_5$),

[9]

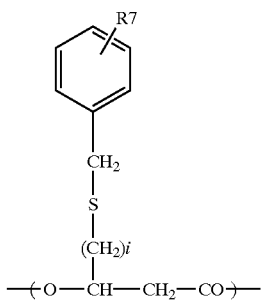

(wherein i represents any one integer selected from the group consisting of 1 to 7, and R7 is selected from the group consisting of a hydrogen atom (H), a halogen atom, —CN, —NO$_2$, —COOR' and —SO$_2$R", wherein R' is selected from the group consisting of a hydrogen atom (H), Na, K, —CH$_3$ and —C$_2$H$_5$, and R" is selected from the group consisting of —OH, —ONa, —OK, a halogen atom, —OCH$_3$ and —OC$_2$H$_5$), and

[10]

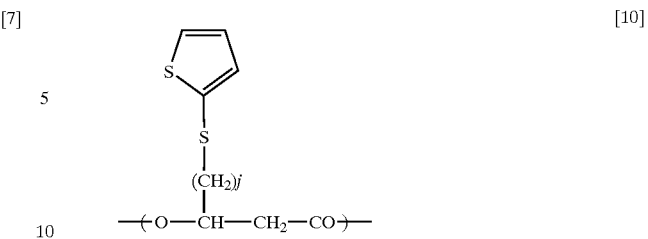

(wherein j represents any one integer selected from the group consisting of 1 to 9),

[12]

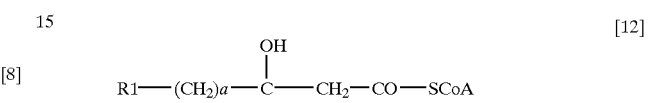

(wherein —SCoA represents a CoA bound to alkanoic acid, symbol "a" represents an integer, and the combination of R1 and a is defined as the same as the combination of R1 and a in the monomer unit expressed by the above described Formula [1]),

[13]

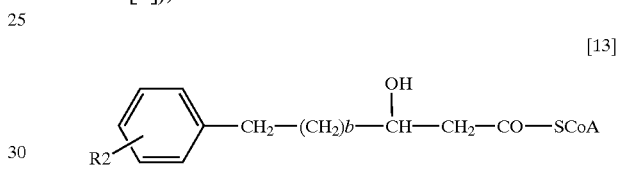

(wherein —SCoA represents a CoA bound to alkanoic acid, and b and R2 are respectively defined as the same as b and R2 in the monomer unit expressed by the above described Formula [2]),

[14]

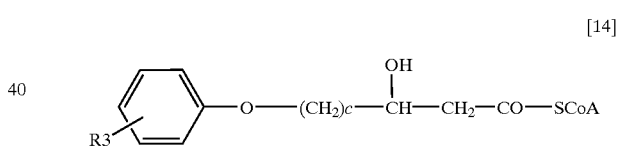

(wherein —SCoA represents a CoA bound to alkanoic acid, and c and R3 are respectively defined as the same as c and R3 in the monomer unit expressed by the above described Formula [3]),

[15]

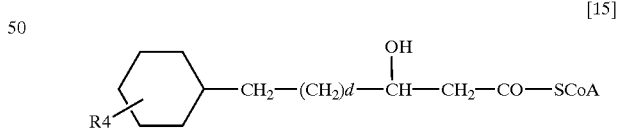

(wherein —SCoA represents a CoA bound to alkanoic acid, and d and R4 are respectively defined as the same as d and R4 in the monomer unit expressed by the above described Formula [4]),

[16]

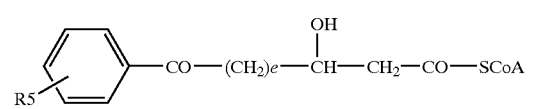

(wherein —SCoA represents a CoA bound to alkanoic acid, and e and R5 are respectively defined as the same as e and R5 in the monomer unit expressed by the above described Formula [5]),

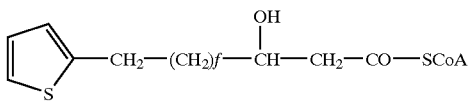  [17]

(wherein —SCoA represents a CoA bound to alkanoic acid, and f is defined as the same as f in the monomer unit expressed by the above described Formula [6]),

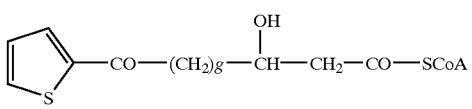  [18]

(wherein —SCoA represents a CoA bound to alkanoic acid, and g is defined as the same as g in the monomer unit expressed by the above described Formula [7]),

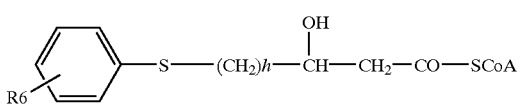  [19]

(wherein —SCoA represents a CoA bound to alkanoic acid, and h and R6 are respectively defined as the same as h and R6 in the monomer unit expressed by the above described Formula [8]),

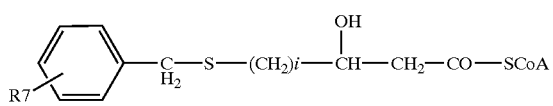  [20]

(wherein —SCoA represents a CoA bound to alkanoic acid, and i and R7 are respectively defined as the same as i and R7 in the monomer unit expressed by the above described Formula [9]), and

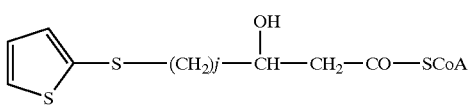  [21]

(wherein —SCoA represents a CoA bound to alkanoic acid, and j is defined as the same as j in the monomer unit expressed by the above described Formula [10]).

3. The manufacturing method according to claim 2, wherein said polyhydroxyalkanoate has a carboxyl group and is comprised of at least one selected from the group consisting of monomer units expressed by Formula [11], and each corresponding 3-hydroxyacyl coenzyme A is selected from the group consisting of 3-hydroxyacyl coenzymes A expressed by Formula [22], said Formulas being:

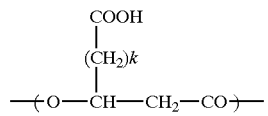  [11]

wherein k represents an integer of 1 to 10, and

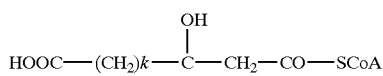  [22]

wherein —SCoA in the formula represents coenzyme A binding to alkanoic acid, and k in the formula is defined as in Formula [11].

4. The manufacturing method according to claim 1, wherein the 3-hydroxyalkanoic acid unit composition of said polyhydroxyalkanoate is made to change in a lamination direction of said polyhydroxyalkanoate-containing structure by varying the composition of said 3-hydroxyacyl coenzyme A with time.

5. The manufacturing method according to claim 1, the method further comprising a step of conducting chemical modification on at least a part of polyhydroxyalkanoate, said base material being coated with the polyhydroxyalkanoate.

6. The manufacturing method according to claim 5, wherein said step of conducting chemical modification is a step of adding a graft chain to at least a part of said polyhydroxyalkanoate.

7. The manufacturing method according to claim 6, wherein said step of adding a graft chain is a step of reacting at least a part of said polyhydroxyalkanoate with a compound having a reactive functional group at an end thereof.

8. The manufacturing method according to claim 6, wherein said polyhydroxyalkanoate is comprised of at least a monomer unit having an epoxy group.

9. The manufacturing method according to claim 7, wherein said compound having a reactive functional group at an end thereof is a compound having an amino group.

10. The manufacturing method according to claim 9, wherein said compound having an amino group is a terminal amino-modified compound.

11. The manufacturing method according to claim 10, wherein said terminal amino-modified compound is at least one selected from the group consisting of polyvinylamine, polyethyleneimine and terminal amino-modified polysiloxane.

12. The manufacturing method according to claim 5, wherein said step of conducting chemical modification is a step of crosslinking at least a part of polyhydroxyalkanoate.

13. The manufacturing method according to claim 12, wherein said step of crosslinking is a step of reacting at least a part of said polyhydroxyalkanoate with a crosslinking agent.

14. The manufacturing method according to claim 12, wherein
said polyhydroxyalkanoate is comprised of at least a monomer unit having an epoxy group.

15. The manufacturing method according to claim 13, wherein
said crosslinking agent is at least one selected from the group consisting of a diamine compound, succinic anhydride and 2-methyl-4-methylimidazole.

16. The manufacturing method according to claim 15, wherein
said diamine compound is hexamethylenediamine.

17. The manufacturing method according to claim 12, wherein
said step of crosslinking is a step of irradiating said polyhydroxyalkanoate with electron rays.

18. The manufacturing method according to claim 1, wherein
said amino acid sequence capable of binding to the base material is an amino acid sequence determined by screening of a random peptide library.

19. The manufacturing method according to claim 1, wherein
the base material is copper phthalocyanine and the amino acid sequence capable of binding to said base material is all or a part of at least one amino acid sequence selected from the group consisting of followings:
Lys-Tyr-Asp-Ser-Arg-His-Leu-His-Thr-His-Ser-His (SEQ ID NO:24)
Pro-Asn-Arg-Leu-Gly-Arg-Arg-Pro-Val-Arg-Trp-Glu (SEQ ID NO:25)
Lys-Cys-Cys-Tyr-Tyr-Asp-His-Ser-His-Ala-Leu-Ser (SEQ ID NO:26)
Glu-Tyr-Leu-Ser-Ala-Ile-Val-Ala-Gly-Pro-Trp-Pro (SEQ ID NO:27)
Lys-Leu-Trp-Ile-Leu-Glu-Pro-Thr-Val-Thr-Pro-Thr (SEQ ID NO:28)
Gln-Ser-Asn-Leu-Lys-Val-Ile-Pro-Ser-Trp-Trp-Phe (SEQ ID NO:29)
Trp-Ile-Pro-Pro-Gln-Trp-Ser-Arg-Leu-Ile-Glu-Pro (SEQ ID NO:30)
Asp-His-Pro-Gln-Ala-Lys-Pro-Asn-Trp-Tyr-Gly-Val (SEQ ID NO:31)
Gly-Leu-Pro-Pro-Tyr-Ser-Pro-His-Arg-Leu-Ala-Gln (SEQ ID NO:32)
Lys-Leu-Thr-Thr-Gln-Tyr-Met-Ala-Arg-Ser-Ser-Ser (SEQ ID NO:33)
Lys-Val-Trp-Met-Leu-Pro-Pro-Leu-Pro-Gln-Ala-Thr (SEQ ID NO:34)
Asn-Val-Thr-Ser-Thr-Ala-Phe-Ile-Asp-Thr-Pro-Trp (SEQ ID NO:35)
Arg-Leu-Asn-Leu-Asp-Ile-Ile-Ala-Val-Thr-Ser-Val (SEQ ID NO:36)
Thr-Leu-Pro-Ser-Pro-Leu-Ala-Leu-Leu-Thr-Val-His (SEQ ID NO:37)
Thr-Asn-Arg-His-Asn-Pro-His-His-Leu-His-His-Val (SEQ ID NO:38).

20. The manufacturing method according to claim 19, wherein
the base material is copper phthalocyanine and the amino acid sequence capable of binding to said base material is all or a part of Lys-Tyr-Asp-Ser-Arg-His-Leu-His-Thr-His-Ser-His (SEQ ID NO:24).

21. The manufacturing method according to claim 19, wherein
the base material is copper phthalocyanine and the amino acid sequence capable of binding to said base material is all or a part of Pro-Asn-Arg-Leu-Gly-Arg-Arg-Pro-Val-Arg-Trp-Glu (SEQ ID NO:25).

22. The manufacturing method according to claim 1, wherein
the base material is Carbon Black and the amino acid sequence capable of binding to said base material is all or a part of at least one amino acid sequence selected from the group consisting of followings:
Trp-Pro-His-Ala-Trp-Lys-Val-Trp-Trp-Pro-Ala-Ser (SEQ ID NO:39)
Asn-Trp-Trp-Trp-Pro-Pro-Tyr-Ile-Arg-His-Gln-Pro (SEQ ID NO:40)
Trp-His-Trp-Ser-Trp-Thr-Pro-Trp-Pro-Ser-His-His (SEQ ID NO:41)
Trp-Pro-Trp-Ala-Trp-His-Pro-Ser-Arg-Asp-Val-Tyr (SEQ ID NO:42)
Trp-His-Gly-Tyr-Trp-Tyr-Ser-Asn-Leu-Asn-Thr-Thr (SEQ ID NO:43)
Trp-Trp-Thr-Pro-Trp-Met-Ser-His-Ala-Tyr-Pro-Val (SEQ ID NO:44)
Trp-Pro-Asn-Pro-Tyr-Trp-Gly-Trp-Phe-Ala-Ala-Val (SEQ ID NO:45)
Thr-Ser-Trp-His-Thr-Trp-Trp-Arg-Gln-Pro-Pro (SEQ ID NO:46)
Asn-Ala-Trp-His-Lys-Tyr-Trp-Trp-Pro-Ile-Thr-Lys (SEQ ID NO:47)
His-Pro-Asn-Asn-Asp-Trp-Ser-Lys-Ala-Pro-Gln-Phe (SEQ ID NO:48)
Trp-Trp-Thr-Pro-Gln-Pro-Trp-Trp-Ser-Phe-Pro-Ile (SEQ ID NO:49)
Trp-Pro-His-Thr-Ser-Trp-Trp-Gln-Thr-Pro-Leu-Thr (SEQ ID NO:50)
Trp-His-Val-Asn-Trp-Asp-Pro-Met-Ala-Trp-Tyr-Arg (SEQ ID NO:51)
Ser-Trp-Pro-Trp-Trp-Thr-Ala-Tyr-Arg-Val-His-Ser (SEQ ID NO:52)
Trp-His-Ser-Asn-Trp-Tyr-Gln-Ser-Ile-Pro-Gln-Val (SEQ ID NO:53)
Gly-Tyr-Trp-Pro-Trp-Lys-Phe-Glu-His-Ala-Thr-Val (SEQ ID NO:54)
Ala-Trp-Trp-Pro-Thr-Thr-Phe-Pro-Pro-Tyr-Tyr-Tyr (SEQ ID NO:55)
Asn-Pro-Trp-Trp-Ser-His-Tyr-Tyr-Pro-Arg-Ser-Val (SEQ ID NO:56)
Trp-Pro-His-Asn-Tyr-Pro-Leu-Asn-His-Ser-Asn-Pro (SEQ ID NO:57)
Thr-Trp-Ala-His-Pro-Leu-Glu-Ser-Asp-Tyr-Leu-Arg (SEQ ID NO:58)
His-Thr-Tyr-Tyr-His-Asp-Gly-Trp-Arg-Leu-Ala-Pro (SEQ ID NO:59)
Thr-Phe-Val-Gln-Thr-Pro-Leu-Ser-His-Leu-Ile-Ala (SEQ ID NO:60)
Arg-Val-Pro-Pro-Ser-Lys-Leu-Thr-Arg-Pro-Pro-Phe (SEQ ID NO:61)
His-Ser-Ile-Tyr-Ser-Val-Thr-Pro-Ser-Thr-Ala-Ser (SEQ ID NO:62)
Leu-Asn-Thr-Gln-Asn-His-Ala-Pro-Leu-Pro-Ser-Ile (SEQ ID NO:63).

23. The manufacturing method according to claim 22, wherein
the base material is Carbon Black and the amino acid sequence capable of binding to said base material is all or a part of Trp-Pro-His-Ala-Trp-Lys-Val-Trp-Trp-Pro-Ala-Ser (SEQ ID NO:39).

24. The manufacturing method according to claim 22, wherein
the base material is Carbon Black and the amino acid sequence capable of binding to said base material is all or a part of Asn-Trp-Trp-Trp-Pro-Pro-Tyr-Ile-Arg-His-Gln-Pro (SEQ ID NO:40).

25. The manufacturing method according to claim 1, wherein the base material is titanium oxide and the amino acid sequence capable of binding to said base material is all or a part of at least one amino acid sequence selected from the group consisting of followings:

His-Ala-Thr-Gly-Thr-His-Gly-Leu-Ser-Leu-Ser-His (SEQ ID NO:150)

Thr-Leu-Pro-Ser-Pro-Leu-Ala-Leu-Leu-Thr-Val-His (SEQ ID NO:151)

Leu-Ser-Thr-His-Tyr-Val-Asn-Arg-Ser-His-Tle-Thr (SEQ ID NO:152)

Ala-Tyr-His-Ile-Asn-Gln-Leu-Gly-Ala-Pro-Pro-Ala (SEQ ID NO:153)

Leu-His-Leu-Thr-Pro-His-Pro-Gly-Asp-Thr-Leu-Thr (SEQ ID NO:154)

Gln-Asp-Val-His-Leu-Thr-Gln-Gln-Ser-Arg-Tyr-Thr (SEQ ID NO:155)

Leu-Glu-Ile-Pro-Ser-Asn-Gly-Leu-Asn-His-Lys-Ile (SEQ ID NO:156)

Leu-Glu-Ile-Pro-Ser-Asn-Gly-Leu-Asn-His-Asn-Ile (SEQ ID NO:157).

26. The manufacturing method according to claim 25, wherein the base material is titanium oxide and the amino acid sequence capable of binding to said base material is all or a part of His-Ala-Thr-Gly-Thr-His-Gly-Leu-Ser-Leu-Ser-His (SEQ ID NO:150).

27. The manufacturing method according to claim 25, wherein the base material is titanium oxide and the amino acid sequence capable of binding to said base material is all or a part of Thr-Leu-Pro-Ser-Pro-Leu-Ala-Leu-Leu-Thr-Val-His (SEQ ID NO:151).

28. The manufacturing method according to claim 1, wherein the base material is a silicon board and the amino acid sequence capable of binding to said base material is Asp-Ser-His-Phe-Thr-Ile-Asn (SEQ ID NO:21).

29. The manufacturing method according to claim 1, wherein the polyhydroxyalkanoate synthase is a polyhydroxyalkanoate synthase produced by a microbe having a capacity of production of said synthase or a transformer made by incorporating a gene associated with said capacity of production into a host.

30. The manufacturing method according to claim 29, wherein the microbe having a capacity of production of polyhydroxyalkanoate synthase is a microbe belonging to *Pseudomonas* sp.

31. The manufacturing method according to claim 30, wherein the microbe having a capacity of production of polyhydroxyalkanoate synthase is at least one microbe selected from the group consisting of *Pseudomonas putida* p91, FERM BP-7373; *Pseudomonas cichorii* H45, FERM BP-7374; *Pseudomonas cichorii* YN2, FERM BP-7375; and *Pseudomonas jessenii* P161, FERM BP-7376.

32. The manufacturing method according to claim 29, wherein the microbe having a capacity of production of polyhydroxyalkanoate synthase is a microbe belonging to *Burkholderia* sp.

33. The manufacturing method according to claim 32, wherein the microbe having a capacity of production of polyhydroxyalkanoate synthase is at least one microbe selected from the group consisting of *Burkholderia cepacia* KK01, FERM BP-4235; *Burkholderia* sp. OK3, FERM P-17370; and *Burkholderia* sp. OK4, FERM P-17371.

34. The manufacturing method according to claim 29, wherein the microbe having a capacity of production of polyhydroxyalkanoate synthase is a microbe belonging to *Alcaligenes* sp.

35. The manufacturing method according to claim 34, wherein the microbe having a capacity of production of polyhydroxyalkanoate synthase is *Alcaligenes* sp. TL2, FERM BP-6913.

36. The manufacturing method according to claim 29, wherein the microbe having a capacity of production of polyhydroxyalkanoate synthase is a microbe belonging to *Ralstonia* sp.

37. The manufacturing method according to claim 36, wherein the microbe having a capacity of production of polyhydroxyalkanoate synthase is *Ralstonia eutropha* TB64, FERM BP-6933.

38. The manufacturing method according to claim 29, wherein said host microbe of the transformer is *Escherichia coli*.

* * * * *

UNITED STATES PATENT AND TRADEMARK OFFICE
CERTIFICATE OF CORRECTION

PATENT NO. : 6,951,745 B2
APPLICATION NO. : 10/191540
DATED : October 4, 2005
INVENTOR(S) : Tsuyoshi Nomoto et al.

It is certified that error appears in the above-identified patent and that said Letters Patent is hereby corrected as shown below:

COLUMN 2
Line 57, "requires" should read --require--; and
Line 65, "nonpetroeum-based" should read --nonpetroleum-based--.

COLUMN 3
Line 45, "inventor" should read --inventors--.

COLUMN 4
Line 22, "a image" should read --an image--;
Line 31, "run; and" should read --run.--; and
Line 58, "dimethylphophate" should read --dimethylphosphate--.

COLUMN 5
Line 3, "benzoete," should read --benzoate,--; and
Line 61, "Off course," should read --Of course,--.

COLUMN 6
Line 8, "(G P., Science" should read --G P. (Science--; and
Line 27, "allowed" should read --allowed to be--.

COLUMN 8
Line 29, "3-hydrozybutyryl" should read --3-hydroxybutyryl--.

COLUMN 13
Line 31, "selected" should read --selected from--; and
Line 64, "Formula [11]." should read --Formula [11]).--.

COLUMN 16
Line 8, "BP-7376," should read --FERM BP-7376,--.

COLUMN 17
Line 24, "$NiCi_2$:0.1 g" should read --$NiCl_2$:0.1 g--.

COLUMN 18
Line 12, "decrasing" should read --decreasing--;
Line 15, "New EnglanBiolab" should read --New EnglandBiolab--;
Line 16, "a expression" should read --an expression--; and
Line 24, "A various" should read --Various--.

UNITED STATES PATENT AND TRADEMARK OFFICE
CERTIFICATE OF CORRECTION

PATENT NO. : 6,951,745 B2
APPLICATION NO. : 10/191540
DATED : October 4, 2005
INVENTOR(S) : Tsuyoshi Nomoto et al.

It is certified that error appears in the above-identified patent and that said Letters Patent is hereby corrected as shown below:

COLUMN 19
Line 43, "allowed" should read --allowed to be--; and
Line 60, "(G P., Science" should read --G P. (Science--.

COLUMN 20
Line 62, "to respect" should read --with respect--.

COLUMN 21
Line 7, "a plural kinds" should read --plural kinds--;
Line 21, "interfere" should read --interfere with--; and
Line 47, "interfering" should read --interfering with--.

COLUMN 22
Line 13, "shook" should read --shaken--.

COLUMN 23
Line 52, "0,2 M." should read --0.2 M.--; and
Line 58, "describe" should read --described--.

COLUMN 24
Line 22, "out shell," should read --outer shell,--.

COLUMN 25
Line 57, "form" should read --from--.

COLUMN 27
Line 1, "was" should read --was used--.

COLUMN 28
Line 20, "fragment" should read --fragments--.

COLUMN 41
Line 12, "single" should read --a single--.

COLUMN 42
Line 66, "resulting," should read --resultant,--.

COLUMN 43
Line 66, "were" should read --was--.

UNITED STATES PATENT AND TRADEMARK OFFICE
CERTIFICATE OF CORRECTION

PATENT NO. : 6,951,745 B2
APPLICATION NO. : 10/191540
DATED : October 4, 2005
INVENTOR(S) : Tsuyoshi Nomoto et al.

Page 3 of 4

It is certified that error appears in the above-identified patent and that said Letters Patent is hereby corrected as shown below:

COLUMN 44
Line 6, "resulting" should read --resultant--;
Line 22, "minutes)," should read --minutes);--;
Line 22, "after" should read --after being--; and
Line 65, "completed." should read --been completed.--.

COLUMN 45
Line 20, "Eppendorf" should read --an Eppendorf--.

COLUMN 49
Line 40, "500 μ g" should read --500 μg--.

COLUMN 62
Line 60, "agent 1:5 parts" should read --agent 1: 5 parts--; and
Line 64, "cooled," should read --cooled, it was--.

COLUMN 63
Line 10, "prepare and" should read -- prepare a--.

COLUMN 67
Line 48, "shook" should read --shaken--.

COLUMN 68
Line 60, "after" should read --after being--.

COLUMN 71
Line 62, "it an" should read --it in an--; and
Line 67, "it an" should read --it in an--.

COLUMN 75
Line 37, "picolitters" should read --picoliters--.

COLUMN 77
Line 15, "was made" should read --were made--.

COLUMN 81
Line 34, "not binding" should read --no binding--.

COLUMN 152
Line 52, "$C_3F_7$," should read -- —$C_3F_7$,--.

UNITED STATES PATENT AND TRADEMARK OFFICE
CERTIFICATE OF CORRECTION

PATENT NO. : 6,951,745 B2
APPLICATION NO. : 10/191540
DATED : October 4, 2005
INVENTOR(S) : Tsuyoshi Nomoto et al.

It is certified that error appears in the above-identified patent and that said Letters Patent is hereby corrected as shown below:

COLUMN 153
Line 39, "ONa," should read -- –ONa,--.

COLUMN 157
Line 26, "followings:" should read --the following:--.

COLUMN 158
Line 8, "followings:" should read --the following:--.

COLUMN 159
Line 8, "followings:" should read --the following:--.

Signed and Sealed this

Twenty-third Day of January, 2007

JON W. DUDAS
*Director of the United States Patent and Trademark Office*

SEQUENCE LISTING

```
<160> NUMBER OF SEQ ID NOS: 186

<210> SEQ ID NO 1
<211> LENGTH: 559
<212> TYPE: PRT
<213> ORGANISM: Pseudomonas cichorii YN2 ; FERM BP-7375

<400> SEQUENCE: 1

Met Ser Asn Lys Ser Asn Asp Glu Leu Lys Tyr Gln Ala Ser Glu Asn
1               5                   10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160
```

```
His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Thr Ala Ile Thr Gly Ser Lys
        275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
            420                 425                 430

Pro Ile Asp Leu Lys Gln Val Thr Ala Asp Ile Phe Ser Leu Ala Gly
        435                 440                 445

Thr Asn Asp His Ile Thr Pro Trp Lys Ser Cys Tyr Lys Ser Ala Gln
    450                 455                 460

Leu Phe Gly Gly Asn Val Glu Phe Val Leu Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
            500                 505                 510

Lys His Thr Asp Ser Trp Trp Leu His Trp Gln Ala Trp Gln Ala Gln
        515                 520                 525

Arg Ser Gly Glu Leu Lys Lys Ser Pro Thr Lys Leu Gly Ser Lys Ala
    530                 535                 540

Tyr Pro Ala Gly Glu Ala Ala Pro Gly Thr Tyr Val His Glu Arg
545                 550                 555

<210> SEQ ID NO 2
<211> LENGTH: 1680
<212> TYPE: DNA
```

-continued

<213> ORGANISM: Pseudomonas cichorii YN2 ; FERM BP-7375

<400> SEQUENCE: 2

```
atgagtaaca agagtaacga tgagttgaag tatcaagcct ctgaaaacac cttggggctt      60
aatcctgtcg ttgggctgcg tggaaaggat ctactggctt ctgctcgaat ggtgcttagg     120
caggccatca agcaaccggt gcacagcgtc aaacatgtcg cgcactttgg tcttgaactc     180
aagaacgtac tgctgggtaa atccggctg caaccgacca gcgatgaccg tcgcttcgcc      240
gatccggcct ggagccagaa cccgctctat aaacgttatt tgcaaaccta cctggcgtgg     300
cgcaaggaac tccacgactg gatcgatgaa agtaacctcg cccccaagga tgtggcgcgt     360
gggcacttcg tgatcaacct catgaccgaa gccatggcgc cgaccaacac cgcggccaac     420
ccggcggcag tcaaacgctt tttcgaaacc ggtggcaaaa gctgctcga cggcctctcg     480
cacctggcca aggatctggt acacaacggc ggcatgccga gccaggtcaa catgggtgca     540
ttcgaggtcg gcaagagcct gggcgtgacc gaaggcgcgg tggtgtttcg caacgatgtg     600
ctggaactga tccagtacaa gccgaccacc gagcaggtat acgaacgccc gctgctggtg     660
gtgccgccgc agatcaacaa gttctacgtt ttcgacctga gccggacaa gagcctggcg      720
cggttctgcc tgcgcaacaa cgtgcaaacg ttcatcgtca gctggcgaaa tcccaccaag     780
gaacagcgag agtggggcct gtcgacctac atcgaagccc tcaaggaagc ggttgatgtc     840
gttaccgcga tcaccggcag caaagacgtg aacatgctcg gcgcctgctc cggcggcatc     900
acttgcaccg cgctgctggg ccattacgcg gcgattggcg aaaacaaggt caacgccctg     960
accttgctgg tgagcgtgct tgataccacc ctcgacagcg atgttgccct gttcgtcaat    1020
gaacagaccc ttgaagccgc caagcgccac tcgtaccagg ccggcgtact ggaaggccgc    1080
gacatggcga aggtcttcgc ctggatgcgc cccaacgatc tgatctggaa ctactgggtc    1140
aacaattacc tgctaggcaa cgaaccgccg gtgttcgaca tcctgttctg gaacaacgac    1200
accacacggt tgcccgcggc gttccacggc gacctgatcg aactgttcaa aaataaccca    1260
ctgattcgcc cgaatgcact ggaagtgtgc ggcacccca tcgacctcaa gcaggtgacg     1320
gccgacatct tttccctggc cggcaccaac gaccacatca ccccgtggaa gtcctgctac    1380
aagtcggcgc aactgtttgg cggcaacgtt gaattcgtgc tgtcgagcag cgggcatatc    1440
cagagcatcc tgaacccgcc gggcaatccg aaatcgcgct acatgaccag caccgaagtg    1500
gcggaaaatg ccgatgaatg caagcgaat gccaccaagc ataccgattc ctggtggctg     1560
cactggcagc cctggcaggc ccaacgctcg ggcgagctga aaagtcccc gacaaaactg      1620
ggcagcaagg cgtatccggc aggtgaagcg gcgccaggca cgtacgtgca cgaacggtaa    1680
```

<210> SEQ ID NO 3
<211> LENGTH: 560
<212> TYPE: PRT
<213> ORGANISM: Pseudomonas cichorii YN2 ; FERM BP-7375

<400> SEQUENCE: 3

```
Met Arg Asp Lys Pro Ala Arg Glu Ser Leu Pro Thr Pro Ala Lys Phe
  1               5                  10                  15

Ile Asn Ala Gln Ser Ala Ile Thr Gly Leu Arg Gly Arg Asp Leu Val
             20                  25                  30

Ser Thr Leu Arg Ser Val Ala Ala His Gly Leu Arg His Pro Val His
         35                  40                  45

Thr Ala Arg His Ala Leu Lys Leu Gly Gly Gln Leu Gly Arg Val Leu
     50                  55                  60
```

```
Leu Gly Asp Thr Leu His Pro Thr Asn Pro Gln Asp Arg Arg Phe Asp
 65                  70                  75                  80

Asp Pro Ala Trp Ser Leu Asn Pro Phe Tyr Arg Arg Ser Leu Gln Ala
             85                  90                  95

Tyr Leu Ser Trp Gln Lys Gln Val Lys Ser Trp Ile Asp Glu Ser Asn
            100                 105                 110

Met Ser Pro Asp Asp Arg Ala Arg Ala His Phe Ala Phe Ala Leu Leu
            115                 120                 125

Asn Asp Ala Val Ser Pro Ser Asn Ser Leu Leu Asn Pro Leu Ala Ile
        130                 135                 140

Lys Glu Ile Phe Asn Ser Gly Gly Asn Ser Leu Val Arg Gly Ile Gly
145                 150                 155                 160

His Leu Val Asp Asp Leu Leu His Asn Asp Gly Leu Pro Arg Gln Val
                165                 170                 175

Thr Arg His Ala Phe Glu Val Gly Lys Thr Val Ala Thr Thr Thr Gly
            180                 185                 190

Ala Val Val Phe Arg Asn Glu Leu Leu Glu Leu Ile Gln Tyr Lys Pro
        195                 200                 205

Met Ser Glu Lys Gln Tyr Ser Lys Pro Leu Leu Val Val Pro Pro Gln
210                 215                 220

Ile Asn Lys Tyr Tyr Ile Phe Asp Leu Ser Pro His Asn Ser Phe Val
225                 230                 235                 240

Gln Phe Ala Leu Lys Asn Gly Leu Gln Thr Phe Val Ile Ser Trp Arg
                245                 250                 255

Asn Pro Asp Val Arg His Arg Glu Trp Gly Leu Ser Thr Tyr Val Glu
            260                 265                 270

Ala Val Glu Glu Ala Met Asn Val Cys Arg Ala Ile Thr Gly Ala Arg
        275                 280                 285

Glu Val Asn Leu Met Gly Ala Cys Ala Gly Leu Thr Ile Ala Ala
        290                 295                 300

Leu Gln Gly His Leu Gln Ala Lys Arg Gln Leu Arg Arg Val Ser Ser
305                 310                 315                 320

Ala Thr Tyr Leu Val Ser Leu Leu Asp Ser Gln Leu Asp Ser Pro Ala
                325                 330                 335

Thr Leu Phe Ala Asp Glu Gln Thr Leu Glu Ala Ala Lys Arg Arg Ser
            340                 345                 350

Tyr Gln Lys Gly Val Leu Glu Gly Arg Asp Met Ala Lys Val Phe Ala
        355                 360                 365

Trp Met Arg Pro Asn Asp Leu Ile Trp Ser Tyr Phe Val Asn Asn Tyr
370                 375                 380

Leu Met Gly Lys Glu Pro Pro Ala Phe Asp Ile Leu Tyr Trp Asn Asn
385                 390                 395                 400

Asp Asn Thr Arg Leu Pro Ala Ala Leu His Gly Asp Leu Leu Asp Phe
                405                 410                 415

Phe Lys His Asn Pro Leu Ser His Pro Gly Gly Leu Glu Val Cys Gly
            420                 425                 430

Thr Pro Ile Asp Leu Gln Lys Val Thr Val Asp Ser Phe Ser Val Ala
        435                 440                 445

Gly Ile Asn Asp His Ile Thr Pro Trp Asp Ala Val Tyr Arg Ser Thr
        450                 455                 460

Leu Leu Leu Gly Gly Glu Arg Arg Phe Val Leu Ala Asn Ser Gly His
465                 470                 475                 480
```

-continued

```
Val Gln Ser Ile Leu Asn Pro Pro Asn Asn Pro Lys Ala Asn Tyr Leu
            485                 490                 495

Glu Gly Ala Lys Leu Ser Ser Asp Pro Arg Ala Trp Tyr Tyr Asp Ala
        500                 505                 510

Lys Pro Val Asp Gly Ser Trp Trp Thr Gln Trp Leu Gly Trp Ile Gln
    515                 520                 525

Glu Arg Ser Gly Ala Gln Lys Glu Thr His Met Ala Leu Gly Asn Gln
530                 535                 540

Asn Tyr Pro Pro Met Glu Ala Ala Pro Gly Thr Tyr Val Arg Val Arg
545                 550                 555                 560
```

<210> SEQ ID NO 4
<211> LENGTH: 1683
<212> TYPE: DNA
<213> ORGANISM: Pseudomonas cichorii YN2 ; FERM BP-7375

<400> SEQUENCE: 4

| | | | | | |
|---|---|---|---|---|---|
| atgcgcgata | aacctgcgag | ggagtcacta | cccacccccg | ccaagttcat | caacgcacaa | 60 |
| agtgcgatta | ccggcctgcg | tggccgggat | ctggtttcga | ctttgcgcag | tgtcgccgcc | 120 |
| catggcctgc | gccaccccgt | gcacaccgcg | cgacacgcct | tgaaactggg | tggtcaactg | 180 |
| ggacgcgtgt | tgctgggcga | caccctgcat | cccaccaacc | cgcaagaccg | tcgcttcgac | 240 |
| gatccggcgt | ggagtctcaa | tccctttttat | cgtcgcagcc | tgcaggcgta | cctgagctgg | 300 |
| cagaagcagg | tcaagagctg | gatcgacgaa | agcaacatga | ccccggatga | ccgcgcccgt | 360 |
| gcgcacttcg | cgttcgccct | gctcaacgat | gccgtgtcgc | cgtccaacag | cctgctcaat | 420 |
| ccgctggcga | tcaaggaaat | cttcaactcc | ggcggcaaca | gcctggtgcg | cgggatcggc | 480 |
| catctggtcg | atgacctctt | gcacaacgat | ggcttgcccc | ggcaagtcac | caggcatgca | 540 |
| ttcgaggttg | gcaagaccgt | cgccaccacc | accggcgccg | tggtgtttcg | caacgagctg | 600 |
| ctggagctga | tccaatacaa | gccgatgagc | gaaaagcagt | attccaaacc | gctgctggtg | 660 |
| gtgccgccac | agatcaacaa | gtactacatt | tttgacctca | gcccccataa | cagcttcgtc | 720 |
| cagttcgcgc | tcaagaacgg | cctgcaaacc | ttcgtcatca | gctggcgcaa | tccggatgta | 780 |
| cgtcaccgcg | aatgggcct | gtcgacctac | gtcgaagcgg | tggaagaagc | catgaatgtc | 840 |
| tgccgggcaa | tcaccggcgc | gcgcgaggtc | aacctgatgg | gcgcctgcgc | tggcgggctg | 900 |
| accattgctg | ccctgcaggg | ccacttgcaa | gccaagcgac | agctgcgccg | cgtctccagc | 960 |
| gcgacgtacc | tggtgagcct | gctcgacagc | caactggaca | gcccggccac | actcttcgcc | 1020 |
| gacgaacaga | ccctggaggc | ggccaagcgc | cgctcctacc | agaaaggtgt | gctggaaggc | 1080 |
| cgcgacatgg | ccaaggtttt | cgcctggatg | cgccccaacg | atttgatctg | gagctacttc | 1140 |
| gtcaacaatt | acctgatggg | caaggagccg | ccggcgttcg | acattctcta | ctggaacaat | 1200 |
| gacaacacac | gcctgccggc | cgccctgcat | ggtgacttgc | tggacttctt | caagcacaac | 1260 |
| ccgctgagcc | atccgggtgg | cctggaagtg | tgcggcaccc | cgatcgactt | gcaaaaggtc | 1320 |
| accgtcgaca | gtttcagcgt | ggccggcatc | aacgatcaca | tcacgccgtg | ggacgcggtg | 1380 |
| tatcgctcaa | ccctgttgct | cggtggcgag | cgtcgctttg | tcctggccaa | cagcggtcat | 1440 |
| gtgcagagca | ttctcaaccc | gccgaacaat | ccgaaagcca | actacctcga | aggtgcaaaa | 1500 |
| ctaagcagcg | accccagggc | ctggtactac | gacgccaagc | ccgtcgacgg | tagctggtgg | 1560 |
| acgcaatggc | tgggctggat | tcaggagcgc | tcgggcgcgc | aaaaagaaac | ccacatggcc | 1620 |
| ctcggcaatc | agaattatcc | accgatggag | gcggcgcccg | gacttacgt | gcgcgtgcgc | 1680 |

```
tga                                                          1683
```

<210> SEQ ID NO 5
<211> LENGTH: 20
<212> TYPE: DNA
<213> ORGANISM: Artificial Sequence
<220> FEATURE:
<223> OTHER INFORMATION: Primer for PCR multiplication

<400> SEQUENCE: 5

```
tgctggaact gatccagtac                                          20
```

<210> SEQ ID NO 6
<211> LENGTH: 23
<212> TYPE: DNA
<213> ORGANISM: Artificial Sequence
<220> FEATURE:
<223> OTHER INFORMATION: Primer for PCR multiplication

<400> SEQUENCE: 6

```
gggttgagga tgctctggat gtg                                      23
```

<210> SEQ ID NO 7
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 7

```
ggaccaagct tctcgtctca gggcaatgg                                29
```

<210> SEQ ID NO 8
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 8

```
cgagcaagct tgctcctaca ggtgaaggc                                29
```

<210> SEQ ID NO 9
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 9

```
gtattaagct tgaagacgaa ggagtgttg                                29
```

<210> SEQ ID NO 10
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 10

```
catccaagct tcttatgatc gggtcatgcc                               30
```

<210> SEQ ID NO 11
<211> LENGTH: 45
<212> TYPE: DNA
<213> ORGANISM: Artificial Sequence

```
<220> FEATURE:
<223> OTHER INFORMATION: Primer for PCR multiplication

<400> SEQUENCE: 11
agtggatcct ccgagctcag taacaagagt aacgatgagt tgaag         45

<210> SEQ ID NO 12
<211> LENGTH: 45
<212> TYPE: DNA
<213> ORGANISM: Artificial Sequence
<220> FEATURE:
<223> OTHER INFORMATION: Primer for PCR multiplication

<400> SEQUENCE: 12
atactcgaga ctactagtcc gttcgtgcac gtacgtgcct ggcgc         45

<210> SEQ ID NO 13
<211> LENGTH: 45
<212> TYPE: DNA
<213> ORGANISM: Artificial Sequence
<220> FEATURE:
<223> OTHER INFORMATION: Primer for PCR multiplication

<400> SEQUENCE: 13
agtggatcct ccgagctccg cgataaacct gcgagggagt cacta         45

<210> SEQ ID NO 14
<211> LENGTH: 45
<212> TYPE: DNA
<213> ORGANISM: Artificial Sequence
<220> FEATURE:
<223> OTHER INFORMATION: Primer for PCR multiplication

<400> SEQUENCE: 14
atactcgaga ctactagtgc gcacgcgcac gtaagtcccg ggcgc         45

<210> SEQ ID NO 15
<211> LENGTH: 7
<212> TYPE: PRT
<213> ORGANISM: Artificial Sequence
<220> FEATURE:
<223> OTHER INFORMATION: Copper phthalocyanine-binding peptide

<400> SEQUENCE: 15

Val Phe His Lys Leu Val Trp
1               5

<210> SEQ ID NO 16
<211> LENGTH: 43
<212> TYPE: DNA
<213> ORGANISM: Artificial Sequence
<220> FEATURE:
<223> OTHER INFORMATION: Primer for PCR multiplication

<400> SEQUENCE: 16
gatccgtgtt ccacaaatta gtgtggggtg gaggttcgga gct         43

<210> SEQ ID NO 17
<211> LENGTH: 35
<212> TYPE: DNA
<213> ORGANISM: Artificial Sequence
<220> FEATURE:
<223> OTHER INFORMATION: Primer for PCR multiplication

<400> SEQUENCE: 17
ccgaacctcc accccacact aatttgtgga acacg         35
```

<210> SEQ ID NO 18
<211> LENGTH: 7
<212> TYPE: PRT
<213> ORGANISM: Artificial Sequence
<220> FEATURE:
<223> OTHER INFORMATION: Carbon Black-binding peptide

<400> SEQUENCE: 18

Trp Phe Trp Ile Leu Val Asn
1               5

<210> SEQ ID NO 19
<211> LENGTH: 39
<212> TYPE: DNA
<213> ORGANISM: Artificial Sequence
<220> FEATURE:
<223> OTHER INFORMATION: Primer for PCR multiplication

<400> SEQUENCE: 19
ctagttggtt ctggatttta gtgaacggtg gaggttcgc                      39

<210> SEQ ID NO 20
<211> LENGTH: 39
<212> TYPE: DNA
<213> ORGANISM: Artificial Sequence
<220> FEATURE:
<223> OTHER INFORMATION: Primer for PCR multiplication

<400> SEQUENCE: 20
tcgagcgaac ctccaccgtt cactaaaatc cagaaccaa                      39

<210> SEQ ID NO 21
<211> LENGTH: 7
<212> TYPE: PRT
<213> ORGANISM: Artificial Sequence
<220> FEATURE:
<223> OTHER INFORMATION: SiO2-binding peptide

<400> SEQUENCE: 21

Asp Ser His Phe Thr Ile Asn
1               5

<210> SEQ ID NO 22
<211> LENGTH: 43
<212> TYPE: DNA
<213> ORGANISM: Artificial Sequence
<220> FEATURE:
<223> OTHER INFORMATION: Primer for PCR multiplication

<400> SEQUENCE: 22
gatccgattc acattttact attaatggtg gaggttcgga gct                 43

<210> SEQ ID NO 23
<211> LENGTH: 35
<212> TYPE: DNA
<213> ORGANISM: Artificial Sequence
<220> FEATURE:
<223> OTHER INFORMATION: Primer for PCR multiplication

<400> SEQUENCE: 23
ccgaacctcc accattaata gtaaaatgtg aatcg                          35

<210> SEQ ID NO 24
<211> LENGTH: 12
<212> TYPE: PRT

```
<213> ORGANISM: Artificial Sequence
<220> FEATURE:
<223> OTHER INFORMATION: Copper phthalocyanine-binding peptide

<400> SEQUENCE: 24

Lys Tyr Asp Ser Arg His Leu His Thr His Ser His
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 25

Pro Asn Arg Leu Gly Arg Arg Pro Val Arg Trp Glu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 26

Lys Cys Cys Tyr Tyr Asp His Ser His Ala Leu Ser
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 27

Glu Tyr Leu Ser Ala Ile Val Ala Gly Pro Trp Pro
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 28

Lys Leu Trp Ile Leu Glu Pro Thr Val Thr Pro Thr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 29

Gln Ser Asn Leu Lys Val Ile Pro Ser Trp Trp Phe
1               5                   10

<210> SEQ ID NO 30
<211> LENGTH: 12
<212> TYPE: PRT
<213> ORGANISM: Artificial Sequence
```

```
<220> FEATURE:
<223> OTHER INFORMATION: Copper phthalocyanine-binding peptide

<400> SEQUENCE: 30

Trp Ile Pro Pro Gln Trp Ser Arg Leu Ile Glu Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 31

Asp His Pro Gln Ala Lys Pro Asn Trp Tyr Gly Val
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 32

Gly Leu Pro Pro Tyr Ser Pro His Arg Leu Ala Gln
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 33

Lys Leu Thr Thr Gln Tyr Met Ala Arg Ser Ser Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 34

Lys Val Trp Met Leu Pro Pro Leu Pro Gln Ala Thr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 35

Asn Val Thr Ser Thr Ala Phe Ile Asp Thr Pro Trp
1               5                   10

<210> SEQ ID NO 36
<211> LENGTH: 12
<212> TYPE: PRT
<213> ORGANISM: Artificial Sequence
<220> FEATURE:
```

```
<223> OTHER INFORMATION: Copper phthalocyanine-binding peptide

<400> SEQUENCE: 36

Arg Leu Asn Leu Asp Ile Ile Ala Val Thr Ser Val
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 37

Thr Leu Pro Ser Pro Leu Ala Leu Leu Thr Val His
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Copper phthalocyanine-binding peptide

<400> SEQUENCE: 38

Thr Asn Arg His Asn Pro His His Leu His His Val
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 39

Trp Pro His Ala Trp Lys Val Trp Trp Pro Ala Ser
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 40

Asn Trp Trp Trp Pro Pro Tyr Ile Arg His Gln Pro
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 41

Trp His Trp Ser Trp Thr Pro Trp Pro Ser His His
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Carbon Black-binding peptide
```

```
<400> SEQUENCE: 42

Trp Pro Trp Ala Trp His Pro Ser Arg Asp Val Tyr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 43

Trp His Gly Tyr Trp Tyr Ser Asn Leu Asn Thr Thr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 44

Trp Trp Thr Pro Trp Met Ser His Ala Tyr Pro Val
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 45

Trp Pro Asn Pro Tyr Trp Gly Trp Phe Ala Ala Val
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 46

Thr Ser Trp His Thr Trp Trp Trp Arg Gln Pro Pro
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 47

Asn Ala Trp His Lys Tyr Trp Trp Pro Ile Thr Lys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Carbon Black-binding peptide
```

```
<400> SEQUENCE: 48

His Pro Asn Asn Asp Trp Ser Lys Ala Pro Gln Phe
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 49

Trp Trp Thr Pro Gln Pro Trp Trp Ser Phe Pro Ile
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 50

Trp Pro His Thr Ser Trp Trp Gln Thr Pro Leu Thr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 51

Trp His Val Asn Trp Asp Pro Met Ala Trp Tyr Arg
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 52

Ser Trp Pro Trp Trp Thr Ala Tyr Arg Val His Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 53

Trp His Ser Asn Trp Tyr Gln Ser Ile Pro Gln Val
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 54
```

```
Gly Tyr Trp Pro Trp Lys Phe Glu His Ala Thr Val
1               5                   10
```

<210> SEQ ID NO 55
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 55

```
Ala Trp Trp Pro Thr Thr Phe Pro Pro Tyr Tyr Tyr
1               5                   10
```

<210> SEQ ID NO 56
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 56

```
Asn Pro Trp Trp Ser His Tyr Tyr Pro Arg Ser Val
1               5                   10
```

<210> SEQ ID NO 57
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 57

```
Trp Pro His Asn Tyr Pro Leu Asn His Ser Asn Pro
1               5                   10
```

<210> SEQ ID NO 58
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 58

```
Thr Trp Ala His Pro Leu Glu Ser Asp Tyr Leu Arg
1               5                   10
```

<210> SEQ ID NO 59
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 59

```
His Thr Tyr Tyr His Asp Gly Trp Arg Leu Ala Pro
1               5                   10
```

<210> SEQ ID NO 60
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 60

```
Thr Phe Val Gln Thr Pro Leu Ser His Leu Ile Ala
1               5                   10
```

<210> SEQ ID NO 61
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 61

```
Arg Val Pro Pro Ser Lys Leu Thr Arg Pro Pro Phe
1               5                   10
```

<210> SEQ ID NO 62
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 62

```
His Ser Ile Tyr Ser Val Thr Pro Ser Thr Ala Ser
1               5                   10
```

<210> SEQ ID NO 63
<211> LENGTH: 12
<212> TYPE: PRT
<213> ORGANISM: Artificial Sequence
<220> FEATURE:
<223> OTHER INFORMATION: Carbon Black-binding peptide

<400> SEQUENCE: 63

```
Leu Asn Thr Gln Asn His Ala Pro Leu Pro Ser Ile
1               5                   10
```

<210> SEQ ID NO 64
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 64
gatccaaata tgatagccgt catctgcata cccatagcca tgagct                    46

<210> SEQ ID NO 65
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 65
catggctatg ggtatgcaga tgacggctat catatttg                             38

<210> SEQ ID NO 66
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 66 gatcccccgaa ccgtctgggc cgtcgtccgg tgcgttggga agagct                   46

```
<210> SEQ ID NO 67
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 67
cttcccaacg caccggacga cggcccagac ggttcggg                              38

<210> SEQ ID NO 68
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 68
gatccaaatg ctgctattat gatcatagcc atgcgctgag cgagct                    46

<210> SEQ ID NO 69
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 69
cgctcagcgc atggctatga tcataatagc agcatttg                              38

<210> SEQ ID NO 70
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 70
gatccgaata tctgagcgcg attgtggcgg gcccgtggcc ggagct                    46

<210> SEQ ID NO 71
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 71
ccggccacgg gcccgccaca atcgcgctca gatattcg                              38

<210> SEQ ID NO 72
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 72
gatccaaact gtggattctg gaaccgaccg tgaccccgac cgagct                    46

<210> SEQ ID NO 73
<211> LENGTH: 38
<212> TYPE: DNA
<213> ORGANISM: Artificial Sequence
<220> FEATURE:
<223> OTHER INFORMATION: Primer for PCR multiplication
```

```
<400> SEQUENCE: 73
cggtcggggt cacggtcggt tccagaatcc acagtttg                              38

<210> SEQ ID NO 74
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 74
gatcccagag caacctgaaa gtgattccga gctggtggtt tgagct                    46

<210> SEQ ID NO 75
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 75
caaaccacca gctcggaatc actttcaggt tgctctgg                              38

<210> SEQ ID NO 76
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 76
gatcctggat tccgccgcag tggagccgtc tgattgaacc ggagct                    46

<210> SEQ ID NO 77
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 77
ccggttcaat cagacggctc cactgcggcg gaatccag                              38

<210> SEQ ID NO 78
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 78
gatccgatca tccgcaggcg aaaccgaact ggtatggcgt ggagct                    46

<210> SEQ ID NO 79
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 79
ccacgccata ccagttcggt ttcgcctgcg gatgatcg                              38

<210> SEQ ID NO 80
<211> LENGTH: 46
```

```
<212> TYPE: DNA
<213> ORGANISM: Artificial Sequence
<220> FEATURE:
<223> OTHER INFORMATION: Primer for PCR multiplication

<400> SEQUENCE: 80
gatccggcct gccgccgtat agcccgcatc gtctggcgca ggagct          46

<210> SEQ ID NO 81
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 81
cctgcgccag acgatgcggg ctatacggcg gcaggccg                    38

<210> SEQ ID NO 82
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 82
gatccaaact gaccacccag tatatggcgc gtagcagcag cgagct           46

<210> SEQ ID NO 83
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 83
cgctgctgct acgcgccata tactgggtgg tcagtttg                    38

<210> SEQ ID NO 84
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 84
gatccaaagt gtggatgctg ccgccgctgc cgcaggcgac cgagct           46

<210> SEQ ID NO 85
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 85
cggtcgcctg cggcagcggc ggcagcatcc acactttg                    38

<210> SEQ ID NO 86
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 86
```
gatccaacgt gaccagcacc gcgtttattg atacccgtg ggagct    46

<210> SEQ ID NO 87
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 87
cccacggggt atcaataaac gcggtgctgg tcacgttg    38

<210> SEQ ID NO 88
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 88
gatcccgtct gaacctggat attattgcgg tgaccagcgt ggagct    46

<210> SEQ ID NO 89
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 89
ccacgctggt caccgcaata atatccaggt tcagacgg    38

<210> SEQ ID NO 90
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 90
gatccaccct gccgagcccg ctggcgctgc tgaccgtgca tgagct    46

<210> SEQ ID NO 91
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 91
catgcacggt cagcagcgcc agcgggctcg gcagggtg    38

<210> SEQ ID NO 92
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 92
gatccaccaa ccgtcataac ccgcatcatc tgcatcatgt ggagct    46

<210> SEQ ID NO 93
<211> LENGTH: 38
<212> TYPE: DNA
<213> ORGANISM: Artificial Sequence

```
<220> FEATURE:
<223> OTHER INFORMATION: Primer for PCR multiplication

<400> SEQUENCE: 93
ccacatgatg cagatgatgc gggttatgac ggttggtg                          38

<210> SEQ ID NO 94
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 94
gatcctggcc gcatgcgtgg aaagtgtggt ggccggcgag cgagct                 46

<210> SEQ ID NO 95
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 95
cgctcgccgg ccaccacact ttccacgcat gcggccag                          38

<210> SEQ ID NO 96
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 96
gatccaactg gtggtggccg ccgtatattc gtcatcagcc ggagct                 46

<210> SEQ ID NO 97
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 97
ccggctgatg acgaatatac ggcggccacc accagttg                          38

<210> SEQ ID NO 98
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 98
gatcctggca ttggagctgg accccgtggc cgagccatca tgagct                 46

<210> SEQ ID NO 99
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 99
catgatggct cggccacggg gtccagctcc aatgccag                          38
```

<210> SEQ ID NO 100
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 100
gatcctggcc gtgggcgtgg catccgagcc gtgatgtgta tgagct        46

<210> SEQ ID NO 101
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 101
catacacatc acggctcgga tgccacgccc acggccag              38

<210> SEQ ID NO 102
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 102
gatcctggca tggctattgg tatagcaacc tgaacaccac cgagct        46

<210> SEQ ID NO 103
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 103
cggtggtgtt caggttgcta taccaatagc catgccag              38

<210> SEQ ID NO 104
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 104
gatcctggtg gaccccgtgg atgagccatg cgtatccggt ggagct        46

<210> SEQ ID NO 105
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 105
ccaccggata cgcatggctc atccacgggg tccaccag              38

<210> SEQ ID NO 106
<211> LENGTH: 46
<212> TYPE: DNA
<213> ORGANISM: Artificial Sequence
<220> FEATURE:
<223> OTHER INFORMATION: Primer for PCR multiplication

```
<400> SEQUENCE: 106
gatcctggcc gaacccgtat tggggctggt ttgcggcggt ggagct            46

<210> SEQ ID NO 107
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 107
ccaccgccgc aaaccagccc caatacgggt tcggccag                     38

<210> SEQ ID NO 108
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 108
gatccaccag ctggcatacc tggtggtggc gtcagccgcc ggagct            46

<210> SEQ ID NO 109
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 109
ccggcggctg acgccaccac caggtatgcc agctggtg                     38

<210> SEQ ID NO 110
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 110
gatccaacgc gtggcataaa tattggtggc cgattaccaa agagct            46

<210> SEQ ID NO 111
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 111
ctttggtaat cggccaccaa tatttatgcc acgcgttg                     38

<210> SEQ ID NO 112
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 112
gatcccatcc gaacaacgat tggagcaaag cgccgcagtt tgagct            46

<210> SEQ ID NO 113
```

```
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 113
caaactgcgg cgctttgctc caatcgttgt tcggatgg                              38

<210> SEQ ID NO 114
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 114
gatcctggtg gaccccgcag ccgtggtgga gctttccgat tgagct                    46

<210> SEQ ID NO 115
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 115
caatcggaaa gctccaccac ggctgcgggg tccaccag                              38

<210> SEQ ID NO 116
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 116
gatcctggcc gcataccagc tggtggcaga ccccgctgac cgagct                    46

<210> SEQ ID NO 117
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 117
cggtcagcgg ggtctgccac cagctggtat gcggccag                              38

<210> SEQ ID NO 118
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 118
gatcctggca tgtgaactgg gatccgatgg cgtggtatcg tgagct                    46

<210> SEQ ID NO 119
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 119
```

```
cacgatacca cgccatcgga tcccagttca catgccag                                38
```

<210> SEQ ID NO 120
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 120

```
gatccagctg gccgtggtgg accgcgtatc gtgtgcatag cgagct                      46
```

<210> SEQ ID NO 121
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 121

```
cgctatgcac acgatacgcg gtccaccacg gccagctg                                38
```

<210> SEQ ID NO 122
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 122

```
gatcctggca tagcaactgg tatcagagca ttccgcaggt ggagct                      46
```

<210> SEQ ID NO 123
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 123

```
ccacctgcgg aatgctctga taccagttgc tatgccag                                38
```

<210> SEQ ID NO 124
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 124

```
gatccggcta ttggccgtgg aaatttgaac atgcgaccgt ggagct                      46
```

<210> SEQ ID NO 125
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 125

```
ccacggtcgc atgttcaaat ttccacggcc aatagccg                                38
```

<210> SEQ ID NO 126
<211> LENGTH: 46
<212> TYPE: DNA

```
<213> ORGANISM: Artificial Sequence
<220> FEATURE:
<223> OTHER INFORMATION: Primer for PCR multiplication

<400> SEQUENCE: 126
gatccgcgtg gtggccgacc acctttccgc cgtattatta tgagct        46

<210> SEQ ID NO 127
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 127
cataataata cggcggaaag gtggtcggcc accacgcg                 38

<210> SEQ ID NO 128
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 128
gatccaaccc gtggtggagc cattattatc cgcgtagcgt ggagct        46

<210> SEQ ID NO 129
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 129
ccacgctacg cggataataa tggctccacc acgggttg                 38

<210> SEQ ID NO 130
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 130
gatcctggcc gcataactat ccgctgaacc atagcaaccc ggagct        46

<210> SEQ ID NO 131
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 131
ccgggttgct atggttcagc ggatagttat gcggccag                 38

<210> SEQ ID NO 132
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 132
gatccacctg ggcgcatccg ctggaaagcg attatctgcg tgagct        46
```

```
<210> SEQ ID NO 133
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 133
cacgcagata atcgctttcc agcggatgcg cccaggtg                    38

<210> SEQ ID NO 134
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 134
gatcccatac ctattatcat gatggctggc gtctggcgcc ggagct           46

<210> SEQ ID NO 135
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 135
ccggcgccag acgccagcca tcatgataat aggtatgg                    38

<210> SEQ ID NO 136
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 136 gatccaccttt tgtgcagacc ccgctgagcc atctgattgc ggagct          46

<210> SEQ ID NO 137
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 137
ccgcaatcag atggctcagc ggggtctgca caaaggtg                    38

<210> SEQ ID NO 138
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 138
gatcccgtgt gccgccgagc aaactgaccc gtccgccgtt tgagct           46

<210> SEQ ID NO 139
<211> LENGTH: 38
<212> TYPE: DNA
<213> ORGANISM: Artificial Sequence
<220> FEATURE:
```

-continued

<223> OTHER INFORMATION: Primer for PCR multiplication

<400> SEQUENCE: 139
caaacggcgg acgggtcagt ttgctcggcg gcacacgg                                   38

<210> SEQ ID NO 140
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 140
gatcccatag catttatagc gtgaccccga gcaccgcgag cgagct                          46

<210> SEQ ID NO 141
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 141
cgctcgcggt gctcggggtc acgctataaa tgctatgg                                   38

<210> SEQ ID NO 142
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 142
gatccctgaa cacccagaac catgcgccgc tgccgagcat tgagct                          46

<210> SEQ ID NO 143
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 143
caatgctcgg cagcggcgca tggttctggg tgttcagg                                   38

<210> SEQ ID NO 144
<211> LENGTH: 32
<212> TYPE: PRT
<213> ORGANISM: Artificial Sequence
<220> FEATURE:
<223> OTHER INFORMATION: Copper phthalocyanine-binding peptide

<400> SEQUENCE: 144

Lys Tyr Asp Ser Arg His Leu His Thr His Ser His Gly Gly Gly Ser
1               5                   10                  15

Gly Gly Gly Ser Pro Asn Arg Leu Gly Arg Arg Pro Val Arg Trp Glu
            20                  25                  30

<210> SEQ ID NO 145
<211> LENGTH: 106
<212> TYPE: DNA
<213> ORGANISM: Artificial Sequence
<220> FEATURE:
<223> OTHER INFORMATION: Primer for PCR multiplication

<400> SEQUENCE: 145

```
gatccaaata tgatagccgt catctgcata cccatagcca tggcggcggc agcggcggcg      60
gcagcccgaa ccgtctgggc cgtcgtccgg tgcgttggga agagct                    106
```

<210> SEQ ID NO 146
<211> LENGTH: 98
<212> TYPE: DNA
<213> ORGANISM: Artificial Sequence
<220> FEATURE:
<223> OTHER INFORMATION: Primer for PCR multiplication

<400> SEQUENCE: 146

```
cttcccaacg caccggacga cggcccagac ggttcgggct gccgccgccg ctgccgccgc      60
catggctatg ggtatgcaga tgacggctat catatttg                             98
```

<210> SEQ ID NO 147
<211> LENGTH: 32
<212> TYPE: PRT
<213> ORGANISM: Artificial Sequence
<220> FEATURE:
<223> OTHER INFORMATION: Carbon Black-binding peptide

<400> SEQUENCE: 147

Trp Pro His Ala Trp Lys Val Trp Trp Pro Ala Ser Gly Gly Gly Ser
1               5                   10                  15

Gly Gly Gly Ser Asn Trp Trp Trp Pro Pro Tyr Ile Arg His Gln Pro
            20                  25                  30

<210> SEQ ID NO 148
<211> LENGTH: 106
<212> TYPE: DNA
<213> ORGANISM: Artificial Sequence
<220> FEATURE:
<223> OTHER INFORMATION: Primer for PCR multiplication

<400> SEQUENCE: 148

```
gatcctggcc gcatgcgtgg aaagtgtggt ggccggcgag cggcggcggc agcggcggcg      60
gcagcaactg gtggtggccg ccgtatattc gtcatcagcc ggagct                    106
```

<210> SEQ ID NO 149
<211> LENGTH: 98
<212> TYPE: DNA
<213> ORGANISM: Artificial Sequence
<220> FEATURE:
<223> OTHER INFORMATION: Primer for PCR multiplication

<400> SEQUENCE: 149

```
ccggctgatg acgaatatac ggcggccacc accagttgct gccgccgccg ctgccgccgc      60
cgctcgccgg ccaccacact ttccacgcat gcggccag                             98
```

<210> SEQ ID NO 150
<211> LENGTH: 12
<212> TYPE: PRT
<213> ORGANISM: Artificial Sequence
<220> FEATURE:
<223> OTHER INFORMATION: TiO2-binding peptide

<400> SEQUENCE: 150

His Ala Thr Gly Thr His Gly Leu Ser Leu Ser His
1               5                   10

<210> SEQ ID NO 151
<211> LENGTH: 12

```
<212> TYPE: PRT
<213> ORGANISM: Artificial Sequence
<220> FEATURE:
<223> OTHER INFORMATION: TiO2-binding peptide

<400> SEQUENCE: 151

Thr Leu Pro Ser Pro Leu Ala Leu Leu Thr Val His
1               5                   10

<210> SEQ ID NO 152
<211> LENGTH: 12
<212> TYPE: PRT
<213> ORGANISM: Artificial Sequence
<220> FEATURE:
<223> OTHER INFORMATION: TiO2-binding peptide

<400> SEQUENCE: 152

Leu Ser Thr His Tyr Val Asn Arg Ser His Ile Thr
1               5                   10

<210> SEQ ID NO 153
<211> LENGTH: 12
<212> TYPE: PRT
<213> ORGANISM: Artificial Sequence
<220> FEATURE:
<223> OTHER INFORMATION: TiO2-binding peptide

<400> SEQUENCE: 153

Ala Tyr His Ile Asn Gln Leu Gly Ala Pro Pro Ala
1               5                   10

<210> SEQ ID NO 154
<211> LENGTH: 12
<212> TYPE: PRT
<213> ORGANISM: Artificial Sequence
<220> FEATURE:
<223> OTHER INFORMATION: TiO2-binding peptide

<400> SEQUENCE: 154

Leu His Leu Thr Pro His Pro Gly Asp Thr Leu Thr
1               5                   10

<210> SEQ ID NO 155
<211> LENGTH: 12
<212> TYPE: PRT
<213> ORGANISM: Artificial Sequence
<220> FEATURE:
<223> OTHER INFORMATION: TiO2-binding peptide

<400> SEQUENCE: 155

Gln Asp Val His Leu Thr Gln Gln Ser Arg Tyr Thr
1               5                   10

<210> SEQ ID NO 156
<211> LENGTH: 12
<212> TYPE: PRT
<213> ORGANISM: Artificial Sequence
<220> FEATURE:
<223> OTHER INFORMATION: TiO2-binding peptide

<400> SEQUENCE: 156

Leu Glu Ile Pro Ser Asn Gly Leu Asn His Lys Ile
1               5                   10

<210> SEQ ID NO 157
<211> LENGTH: 12
<212> TYPE: PRT
```

<213> ORGANISM: Artificial Sequence
<220> FEATURE:
<223> OTHER INFORMATION: TiO2-binding peptide

<400> SEQUENCE: 157

Leu Glu Ile Pro Ser Asn Gly Leu Asn His Asn Ile
1               5                   10

<210> SEQ ID NO 158
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 158
gatcccatgc gaccggcacc catggcctga gcctgagcca tgagct         46

<210> SEQ ID NO 159
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 159
catggctcag gctcaggcca tgggtgccgg tcgcatgg                  38

<210> SEQ ID NO 160
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 160
gatccaccct gccgagcccg ctggcgctgc tgaccgtgca tgagct         46

<210> SEQ ID NO 161
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 161
catgcacggt cagcagcgcc agcgggctcg gcagggtg                  38

<210> SEQ ID NO 162
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 162
gatccctgag cacccattat gtgaaccgta gccatattac cgagct         46

<210> SEQ ID NO 163
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 163

```
cggtaatatg gctacggttc acataatggg tgctcagg                        38
```

<210> SEQ ID NO 164
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 164

```
gatccgcgta tcatattaac cagctgggcg cgccgccggc ggagct              46
```

<210> SEQ ID NO 165
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 165

```
ccgccggcgg cgcgcccagc tggttaatat gatacgcg                        38
```

<210> SEQ ID NO 166
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 166

```
gatccctgca tctgaccccg catccgggcg ataccctgac cgagct              46
```

<210> SEQ ID NO 167
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 167

```
cggtcagggt atcgcccgga tgcggggtca gatgcagg                        38
```

<210> SEQ ID NO 168
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 168

```
gatcccagga tgtgcatctg acccagcaga gccgttatac cgagct              46
```

<210> SEQ ID NO 169
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 169

```
cggtataacg gctctgctgg gtcagatgca catcctgg                        38
```

<210> SEQ ID NO 170
<211> LENGTH: 46
<212> TYPE: DNA
<213> ORGANISM: Artificial Sequence

```
<220> FEATURE:
<223> OTHER INFORMATION: Primer for PCR multiplication

<400> SEQUENCE: 170
gatccctgga aattccgagc aacggcctga accataaaat tgagct          46

<210> SEQ ID NO 171
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 171 caatttatg gttcaggccg ttgctcggaa tttccagg                     38

<210> SEQ ID NO 172
<211> LENGTH: 46
<212> TYPE: DNA
<213> ORGANISM: Artificial Sequence
<220> FEATURE:
<223> OTHER INFORMATION: Primer for PCR multiplication

<400> SEQUENCE: 172
gatccctgga aattccgagc aacggcctga accataacat tgagct          46

<210> SEQ ID NO 173
<211> LENGTH: 38
<212> TYPE: DNA
<213> ORGANISM: Artificial Sequence
<220> FEATURE:
<223> OTHER INFORMATION: Primer for PCR multiplication

<400> SEQUENCE: 173
caatgttatg gttcaggccg ttgctcggaa tttccagg                    38

<210> SEQ ID NO 174
<211> LENGTH: 32
<212> TYPE: PRT
<213> ORGANISM: Artificial Sequence
<220> FEATURE:
<223> OTHER INFORMATION: TiO2-binding peptide

<400> SEQUENCE: 174

His Ala Thr Gly Thr His Gly Leu Ser Leu Ser His Gly Gly Gly Ser
1               5                   10                  15

Gly Gly Gly Ser Thr Leu Pro Ser Pro Leu Ala Leu Leu Thr Val His
            20                  25                  30

<210> SEQ ID NO 175
<211> LENGTH: 106
<212> TYPE: DNA
<213> ORGANISM: Artificial Sequence
<220> FEATURE:
<223> OTHER INFORMATION: Primer for PCR multiplication

<400> SEQUENCE: 175
gatcccatgc gaccggcacc catggcctga gcctgagcca tggcggcggc agcggcggcg    60
gcagcaccct gccgagcccg ctggcgctgc tgaccgtgca tgagct                  106

<210> SEQ ID NO 176
<211> LENGTH: 98
<212> TYPE: DNA
<213> ORGANISM: Artificial Sequence
<220> FEATURE:
```

-continued

<223> OTHER INFORMATION: Primer for PCR multiplication

<400> SEQUENCE: 176
catgcacggt cagcagcgcc agcgggctcg gcagggtgct gccgccgccg ctgccgccgc    60
catggctcag gctcaggcca tgggtgccgg tcgcatgg    98

<210> SEQ ID NO 177
<211> LENGTH: 4
<212> TYPE: PRT
<213> ORGANISM: Artificial Sequence
<220> FEATURE:
<223> OTHER INFORMATION: Linker sequence

<400> SEQUENCE: 177

Gly Gly Gly Ser
1

<210> SEQ ID NO 178
<211> LENGTH: 7
<212> TYPE: PRT
<213> ORGANISM: Artificial Sequence
<220> FEATURE:
<223> OTHER INFORMATION: Copper phthalocyanine-binding peptide
<220> FEATURE:
<221> NAME/KEY: MISC_FEATURE
<222> LOCATION: (1)..(7)
<223> OTHER INFORMATION: X stands for any amino acids

<400> SEQUENCE: 178

Val Xaa His Xaa Leu Val Xaa
1               5

<210> SEQ ID NO 179
<211> LENGTH: 7
<212> TYPE: PRT
<213> ORGANISM: Artificial Sequence
<220> FEATURE:
<223> OTHER INFORMATION: Carbon Black-binding peptide
<220> FEATURE:
<221> NAME/KEY: MISC_FEATURE
<222> LOCATION: (1)..(7)
<223> OTHER INFORMATION: X stands for any amino acids

<400> SEQUENCE: 179

Trp Xaa Trp Ile Leu Xaa Asn
1               5

<210> SEQ ID NO 180
<211> LENGTH: 7
<212> TYPE: PRT
<213> ORGANISM: Artificial Sequence
<220> FEATURE:
<223> OTHER INFORMATION: SiO2-binding peptide
<220> FEATURE:
<221> NAME/KEY: MISC_FEATURE
<222> LOCATION: (1)..(7)
<223> OTHER INFORMATION: X stands for any amino acids

<400> SEQUENCE: 180

Asp Ser Xaa Xaa Thr Ile Asn
1               5

<210> SEQ ID NO 181
<211> LENGTH: 8
<212> TYPE: PRT
<213> ORGANISM: Artificial Sequence
<220> FEATURE:
<223> OTHER INFORMATION: Linker sequence -continued

```
<400> SEQUENCE: 181

Gly Gly Gly Ser Gly Gly Gly Ser
1               5

<210> SEQ ID NO 182
<211> LENGTH: 7
<212> TYPE: PRT
<213> ORGANISM: Artificial Sequence
<220> FEATURE:
<223> OTHER INFORMATION: Copper phthalocyanine-binding peptide

<400> SEQUENCE: 182

Val Tyr His Arg Leu Val Asn
1               5

<210> SEQ ID NO 183
<211> LENGTH: 7
<212> TYPE: PRT
<213> ORGANISM: Artificial Sequence
<220> FEATURE:
<223> OTHER INFORMATION: Copper phthalocyanine-binding peptide

<400> SEQUENCE: 183

Val Ile His Arg Leu Val Trp
1               5

<210> SEQ ID NO 184
<211> LENGTH: 7
<212> TYPE: PRT
<213> ORGANISM: Artificial Sequence
<220> FEATURE:
<223> OTHER INFORMATION: Carbon Black-binding peptide

<400> SEQUENCE: 184

Trp Tyr Trp Ile Leu Thr Asn
1               5

<210> SEQ ID NO 185
<211> LENGTH: 7
<212> TYPE: PRT
<213> ORGANISM: Artificial Sequence
<220> FEATURE:
<223> OTHER INFORMATION: SiO2-binding peptide

<400> SEQUENCE: 185

Asp Thr Phe His Thr Ile Asn
1               5

<210> SEQ ID NO 186
<211> LENGTH: 7
<212> TYPE: PRT
<213> ORGANISM: Artificial Sequence
<220> FEATURE:
<223> OTHER INFORMATION: SiO2-binding peptide

<400> SEQUENCE: 186

Glu Ser His Phe Thr Ile Asn
1               5
```